United States Patent [19]
Barnett et al.

[11] Patent Number: 5,231,009
[45] Date of Patent: Jul. 27, 1993

[54] CDNAS CODING FOR MEMBERS OF THE CARCINOEMBRYONIC ANTIGEN FAMILY

[75] Inventors: Thomas R. Barnett, East Haven; James J. Elting, Madison; Michael E. Kamarck, Bethany, all of Conn.; Axel W. Kretschmer, Wulfrath, Fed. Rep. of Germany

[73] Assignee: Molecular Diagnostics, Inc., West Haven, Conn.

[21] Appl. No.: 760,031

[22] Filed: Sep. 13, 1991

Related U.S. Application Data

[60] Division of Ser. No. 274,107, Nov. 2, 1988, Pat. No. 5,122,599, which is a continuation-in-part of Ser. No. 207,678, Jun. 15, 1988, abandoned, which is a continuation-in-part of Ser. No. 60,031, Jun. 19, 1987, abandoned, which is a continuation-in-part of Ser. No. 16,683, Feb. 19, 1987, abandoned, which is a continuation-in-part of Ser. No. 896,361, Aug. 13, 1986, abandoned.

[51] Int. Cl.⁵ .................... C12N 57/10; C12N 1/21
[52] U.S. Cl. ...................... 435/240.2; 435/252.3; 536/23.5
[58] Field of Search ............ 435/5, 6, 91, 69.1, 435/240.1, 240.2, 252.3; 536/27

[56] References Cited

U.S. PATENT DOCUMENTS 4,228,236 10/1980 Jakstys et al. ..................... 435/1
4,489,167 12/1984 Ochi et al. ..................... 436/518

OTHER PUBLICATIONS

Gold et al., J. Exp. Med., 121, 439-462 (1965).

Primary Examiner—Margaret Moskowitz
Assistant Examiner—Mindy B. Fleisher
Attorney, Agent, or Firm—Sprung Horn Kramer & Woods

[57] ABSTRACT

A nucleic acid comprising a base sequence which codes for a CEA family member peptide sequence or nucleic acids having a base sequence hybridizable therewith, replicable recombinant cloning vehicles having an insert comprising such nucleic acid, cells transfected, infected or injected with such cloning vehicles, polypeptides expressed by such cells, synthetic peptides derived from the coding sequence of CEA family member nucleic acids, antibody preparations specific for such polypeptides, immunoassays for detecting CEA family members using such antibody preparations and nucleic acid hybridization methods for detecting CEA family member nucleic acid sequences using a nucleic acid probe comprising the above described nucleic acid.

2 Claims, 1 Drawing Sheet

000
CDNAS CODING FOR MEMBERS OF THE CARCINOEMBRYONIC ANTIGEN FAMILY

CROSS-REFERENCES TO RELATED APPLICATIONS

This is a division of application Ser. No. 07/274,107, filed Nov. 2, 1988, now U.S. Pat. No. 5,122,599, which is a continuation-in-part of application Ser. No. 07/207,678, filed Jun. 15, 1988, now abandoned, which is a continuation-in-part application of Ser. No. 07/060,031, filed Jun. 19, 1987, now abandoned, which is a continuation-in-part application of Ser. No. 07/016,683, filed Feb. 19, 1987, now abandoned, which is a continuation-in-part application of Ser. No. 06/896,361, filed Aug. 13, 1986, now abandoned.

BACKGROUND OF THE INVENTION

1. Field of the Invention

The present invention concerns nucleic acid sequences which code for carcinoembryonic antigen (CEA) antigen family peptide sequences.

2. Background Information

Carcinoembryonic antigen was first described by Gold and Freedman, *J. Exp. Med.*, 121, 439–462, (1965). CEA is characterized as a glycoprotein of approximately 200,000 molecular weight with 50-60% by weight of carbohydrate. CEA is present during normal human fetal development, but only in very low concentration in the normal adult intestinal tract. It is produced and secreted by a number of different tumors.

CEA is a clinically useful tumor marker for the management of colorectal cancer patients. CEA can be measured using sensitive immunoassay methods. When presurgical serum levels of CEA are elevated, a postsurgical drop in serum CEA to the normal range typically indicates successful resection of the tumor. Postsurgical CEA levels that do not return to normal often indicated incomplete resection of the tumor or the presence of additional tumor sites in the patient. After returning to normal levels, subsequent rapid rises in serum CEA levels usually indicate the presence of mestastages. Slower postsurgical rises from the normal level are most often interpreted to indicate the presence of new primary tumors not previously detected. Post surgical management of colon cancer patients is thus facilitated by the measurement of CEA.

CEA is a member of an antigen family. Because of this, the immunoassay of CEA by presently available methods is complicated by the fact that CEA is but one of several potentially reactive antigens. There have been at least sixteen CEA-like antigens described in the literature. Since some of these appear to be the same antigen described by different investigators, the actual number of different antigens is somewhat less than this number. Nonetheless, there is a complex array of cross-reactive antigens which can potentially interfere with an immunoassay of the CEA released by tumors. It is known that serum levels of CEA-like antigens are elevated in many non-cancerous conditions such an inflammatory liver diseases and also in smokers. It is important that immunoassays used for the monitoring of cancer patient status not be interfered with by these other CEA-like antigens. Conversely, it is important to be able to distinguish the antigens by immunoassays because of the possibility that different tumor types may preferentially express different forms of CEA. If so, then the ability of reliably measure the different forms of CEA can provide the means to diagnose or more successfully treat different forms of cancer.

The members of the "CEA family" share some antigenic determinants. These common epitopes are not useful in distinguishing the members of the antigen family and antibodies recognizing them are of little use for measuring tumor-specific CEA levels.

U.S. Pat. No. 3,663,684, entitled "Carcinoembryonic Antigen and Diagnostic Method Using Radioactive Iodine", concerns purification and radioiodination of the CEA for use in a RIA.

U.S. Pat. No. 3,697,638 describes that CEA is a mixture of antigens (components A and B in this case). U.S. Pat. No. 3,697,638 mentions methods for separating and radioiodinating each component and their use in specific RIA's.

U.S. Pat. No. 3,852,415, entitled "Compositions for Use in Radioimmunoassay, as Substitute for Blood Plasma Extract in Determination of Carcinoembryonic Antigen" relates to the use of a buffer containing EDTA and bovine serum albumin as a substitute for plasma as a diluent for CEA RIA's.

U.S. Pat. No. 3,867,363, entitled "Carcinoembryonic Antigens", is directed to the isolation of CEA components A and B, their labeling and use in a RIA.

U.S. Pat. No. 3,927,193, entitled "Localization of Tumors by Radiolabelled Antibodies", concerns the use of radiolabelled anti-CEA antibodies in whole body tumor imaging.

U.S. Pat. No. 3,956,258, entitled "Carcinoembryonic Antigens", relates to the isolation of CEA components A and B.

U.S. Pat. No. 4,086,217, entitled "Carcinoembryonic Antigens", is directed to the isolation of CEA components A and B.

U.S. Pat. No. 4,140,753, entitled "Diagnostic Method and Reagent", concerns the purification of a CEA isomer called CEA-S1 and its use in a RIA.

U.S. Pat. No. 4,145,336, entitled "Carcinoembryonic Antigen Isomer", relates to the antigen CEA-S1.

U.S. Pat. No. 4,180,499, entitled "Carcinoembryonic Antigens", describes a process for producing CEA component B.

U.S. Pat. No. 4,228,236, entitled "Process of Producing Carcinoembryonic Antigen", is directed to the use of the established cell lines LS-174T and LS-180 or clones or derivatives thereof for the production of CEA.

U.S. Pat. No. 4,272,504, entitled "Antibody Adsorbed Support Method for Carcinoembryonic Antigen Assay", concerns two concepts for the radioimmunoassay of CEA. First, U.S. Pat. No. 4,272,504 relates to a sample pretreatment in the form of heating to 65° to 85° C. at pH 5 to precipitate and eliminate extraneous protein. Second, it describes the use of a solid phase antibody (either on beads or tubes) as a means to capture analyte and radiolabelled CEA tracer.

U.S. Pat. No. 4,299,815, entitled "Carcinoembryonic Antigen Determination", concerns diluting a CEA sample with water and pretreating by heating to a temperature below which precipitation of protein will occur. The pretreated sample is then immunoassayed using RIA, EIA, FIA or chemiluminescent immunoassay.

U.S. Pat. No. 4,349,528, entitled "Monoclonal Hybridoma Antibody Specific for High Molecular Weight Carcinoembryonic Antigen", is directed to a monoclonal antibody reacting with 180 kD CEA, but not with other molecular weight forms.

U.S. Pat. No. 4,467,031, entitled "Enzyme-Immunoassay for Carcinoembryonic Antigen", relates to a sandwich enzyme immunoassay for CEA in which the first of two anti-CEA monoclonal antibodies in attached to a solid phase and the second monoclonal is conjugated with peroxidase.

U.S. Pat. No. 4,489,167, entitled "Methods and Compositions for Cancer Detection", describes that CEA shares an antigenic determinant with alpha-acid glycoprotein (AG), which is a normal component of human serum. The method described therein concerns a solid-phase sandwich enzyme immunoassay using as one antibody an antibody recognizing AG and another antibody recognizing CEA, but not AC.

U.S. Pat. No. 4,578,349, entitled "Immunoassay for Carcinoembryonic Antigen (CEA)", is directed to the use of high salt containing buffers as diluents in CEA immunoassays.

EP 113072-A, entitled "Assaying Blood Sample for Carcinoembryonic Antigen—After Removal of Interfering Materials by Incubation with Silica Gel", relates to the removal from a serum of a plasma sample of interfering substances by pretreatment with silica gel. The precleared sample is then subjected to an immunoassay.

EP 102008-A, entitled "Cancer Diagnostics Carcinoembryonic Antigen—Produced from Perchloric Acid Extracts Without Electrophoresis", relates to a procedure for the preparation of CEA from perchloric acid extracts, without the use of an electrophoresis step.

EP 92223-A, entitled "Determination of Carcinoembryonic Antigen in Cytosol or tissue—for Therapy Control and Early Recognition of Regression", concerns an immunoassay of CEA, not in serum or plasma, but in the cytosol fraction of the tumor tissue itself.

EP 83103759.6, entitled "Cytosole-CEA-Measurement as Predictive Test in Carcinoma, Particularly Mammacarcinoma", is similar to EP 92223-A.

EP 83303759, entitled "Monoclonal Antibodies Specific to Carcinoembryonic Antigen", relates to the production of "CEA specific" monoclonal antibodies and their use in immunoassays.

WO 84/02983, entitled "Specific CEA-Family Antigens, Antibodies Specific Thereto and Their Methods of Use", is directed to the use of monoclonal antibodies to CEA-meconium (MA)-, and NCA-specific epitopes in immunoassays designed to selectively measure each of these individual components in a sample.

All of the heretofore CEA assays utilize either monoclonal or polyclonal antibodies which are generated by immunizing animals with the intact antigen of choice. None of them address the idea of making sequence specific antibodies for the detection of a unique primary sequence of the various antigens. They do not cover the use of any primary amino acid sequence for the production of antibodies to synthetic peptides or fragments of the natural product. They do not include the concept of using primary amino acid sequences to distinguish the CEA family members. None of them covers the use of DNA or RNA clones for isolating the genes with which to determine the primary sequence.

| DEFINITIONS | |
|---|---|
| Nucleic Acid Abbreviations | |
| A | adenine |
| G | guanine |
| C | cytosine |
| T | thymidine |
| U | uracil |
| Amino Acid Abbreviations: | |
| Asp | aspartic acid |
| Asn | asparagine |
| Thr | threonine |
| Ser | serine |
| Glu | glutamic acid |
| Gln | glutamine |
| Pro | proline |
| Gly | glycine |
| Ala | alanine |
| Cys | cysteine |
| Val | valine |
| Met | methionine |
| Ile | isoleucine |
| Leu | leucine |
| Tyr | tyrosine |
| Phe | phenylalanine |
| Trp | tryptophan |
| Lys | lysine |
| His | histidine |
| Arg | arginine |

Nucleotide—A monomeric unit of DNA or RNA containing a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses.

Functional equivalents—It is well known in the art that in a DNA sequence some nucleotides can be replaced without having an influence on the sequence of the expression product. With respect to the peptide this term means that one or more amino acids which have no function in a particular use can be deleted or replaced by another one.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during translation of mRNA into amino acid sequences. During translation, the proper reading frame must be maintained. For example, the sequence GCTGGTTGTAAG may be translated in three reading frames or phases, each of which affords a different amino acid sequence

```
GCT GGT TGT AAG —Ala—Gly—Cys—Lys
G CTG GTT GTA AG—Leu—Val—Val
GC TGG TTG TAA G—Trp—Leu—(STOP).
```

Polypeptide—A linear array of amion acids connected one to the other by peptide bonds between the alpha-amino and carboxy groups of adjacent amino acids.

Genome—The entire DNA of a cell or a virus. It includes inter alia the structural genes coding for the polypeptides of the cell or virus, as well as its operator, promoter and ribosome binding and interaction sequences, including sequences such as the Shrine-Dalgarno sequences.

Structural Gene—A DNA sequence which encodes through its template or messenger RNA ("mRNA") a sequence of amino acids characteristic of a specific polypeptide.

Transcription—The process of producing mRNA rom a structural gene.

Translation—The process of producing a polypeptide from mRNA.

Expression—The process undergone by a structural gene to produce a polypeptide. It is a combination of transcription and translation.

Plasmid—A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (Tet $^R$) transforms a cell previously sensitive to tetracycline into one which is resistant to it. A cell transformed by a plasmid is called a "transformant".

Phage or Bacteriophage—Bacterial virus, many of which consist of DNA sequences encapsulated in a protein envelope or coat ("capsid protein").

Cloning Vehicle—A palsmid, phage DNA or other DNA sequence which is capable of replicating in a host cell, which is characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is often called a vector.

Cloning—The process of obtaining a population of organisms of DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

cDNA Expression Vector—A procaroytic cloning vehicle which also contains sequences of nucleotides that facilitate expression of cDNA sequences in eucaroytic cells. These nucleotides include sequences that function as eucaryotic promoter, alternative splice sites and polyadenylation signals.

Transformation/Transfection—DNA or RNA is introduced into cells in such a way as to allow gene expression. "Infected" referred to herein concerns the introduction of RNA or DNA by a viral vector into the host.

"Injected" referred to herein concerns the microinjection (use of a small syringe) of DNA into a cell.

CEA antigen family (CEA gene family)—a set of genes (gene family) and their products (antigen family) that share nucleotide sequences homologous to partial cDNA LV-7 (CEA-(a)) and as a result of theses similarities also share a subset of their antigenic epitopes. Examples of the CEA antigen family include CEA (=CEA-(b)), transmembrane CEA (TMCEA)=CEA-(c) and normal crossreacting antigen NCA (=CEA-(d)).

SUMMARY OF THE INVENTION

The present invention concerns the following DNA sequences designated as TM-2 (CEA-(e)), TM-3 (CEA-(f)), TM-4 (CEA-(g)), KGCEA1 and KGCEA2, which code for CEA antigen family peptide sequences or nucleic acids having a base sequence (DNA or RNA) that are hybridizable therewith:

```
                    10                            30                            50
                     .                             .                             .
        CAGCCGTGCTCGAAGCGTTCCTGGAGCCCAAGCTCTCCTCCACAGGTGAAGACAGGGCCA 70                            90                           110
                     .                             .                             .
        GCAGGAGACACCATGGGGCACCTCTCAGCCCCACTTCACAGAGTGCGTGTACCCTGGCAG
                     Met Gly His Leu Ser Ala Pro Leu His Arg Val Arg Val Pro Trp Gln 130                           150                           170
                     .                             .                             .
        GGGCTTCTGCTCACAGCCTC ACTTCTAACCTTCTGGAACCCGCCCACCACTGCCCAGCTC
        Gly Leu Leu Leu Thr Ala Sei Leu Leu Thr Phe Trp Asn Pro Pro Thr Ala Gln Leu 190                           210                           230
                     .                             .                             .
        ACTACTGAATCCATGCCATTCAATGTTGCAGAGGGGAAGGAGGTTCTTCTCCTTGTCCAC
        Thr Thr Glu Ser Met Pro Phe Asn Val Ala Glu Gly Lys Glu Val Leu Leu Val His 250                           270                           290
                     .                             .                             .
        AATCTGCCCCAGCAACTTTTTTGGCTACAGCTGGTACAAAGGGGAAAGAGTGGATGGCAAC
        Asn Leu Pro Gln Gln Leu Phe Gly Tyr Ser Trp Tyr Lys Gly Glu Arg Val Asp Gly Asn 310                           330                           350
                     .                             .                             .
        CGTCAAATTGTAGGATATGCAATAGGAACTCAACAAGCTACCCCAGGGCCCGCAAACAGC
        Arg Gln Ile Val Gly Tyr Ala Ile Gly Thr Gln Gln Ala Thr Pro Gly Pro Ala Asn Ser
```

-continued

```
          370                        390                        410
GGTCGAGAGACAATATACCCCAATGCATCCCTGCTGATCCAGAACGTCACCCAGAATGAC
Gly Arg Glu Thr Ile Tyr Pro Asn Ala Ser Leu Leu Ile Gln Asn Val Thr Gln Asn Asp 430                        450                        470
ACAGGATTCTACACCCTACAAGTCATAAAGTCAGATCTTGTGAATGAAGAAGCAACTGGA
Thr Gly Phe Tyr Thr Leu Gln Val Ile Lys Ser Asp Leu Val Asn Glu Glu Ala Thr Gly 490                        510                        530
CAGTTCCATGTATACCCGGAGCTGCCCAAGCCCTCCATCTCCAGCAACAACTCCAACCCT
Gln Phe His Val Tyr Pro Glu Leu Pro Lys Pro Ser Ile Ser Ser Asn Asn Ser Asn Pro 550                        570                        590
GTGGAGGACAAGGATGCTGTGGCCTTCACCTGTGAACCTGAGACTCAGGACACAACCTAC
Val Glu Asp Lys Asp Ala Val Ala Phe Thr Cys Glu Pro Glu Thr Gln Asp Thr Thr Tyr 610                        630                        650
CTGTGGTGGATAAACAATCAGAGCCTCCCGGTCAGTCCCAGGCTGCAGCTGTCCAATGGC
Leu Trp Trp Ile Asn Asn Gln Ser Leu Pro Val Ser Pro Arg Leu Gln Leu Ser Asn Gly 670                        690                        710
AACAGGACCCTCACTCTACTCAGTGTCACAAGGAATGACACAGGACCCTATGAGTGTGAA
Asn Arg Thr Leu Thr Leu Leu Ser Val Thr Arg Asn Asp Thr Gly Pro Tyr Glu Cys Glu 730                        750                        770
ATACAGAACCCAGTGAGTGCGAACCGCAGTGACCCAGTCACCTTGAATGTCACCTATGGC
Ile Gln Asn Pro Val Ser Ala Asn Arg Ser Asp Pro Val Thr Leu Asn Val Thr Tyr Gly 790                        810                        830
CCGGACACCCCCACCATTTCCCCTTCAGACACCTATTACCGTCCAGGGGCAAACCTCAGC
Pro Asp Thr Pro Thr Ile Ser Pro Ser Asp Thr Tyr Tyr Arg Pro Gly Ala Asn Leu Ser 850                        870                        890
CTCTCCTGCTATGCAGCCTCTAACCCACCTGCACAGTACTCCTGGCTTATCAATGGAACA
Leu Ser Cys Tyr Ala Ala Ser Asn Pro Pro Ala Gln Tyr Ser Trp Leu Ile Asn Gly Thr 910                        930                        950
TTCCAGCAAAGCACACAAGAGCTCTTTATCCCTAACATCACTGTGAATAATAGTGGATCC
Phe Gln Gln Ser Thr Gln Glu Leu Phe Ile Pro Asn Ile Thr Val Asn Asn Ser Gly Ser 970                        990                        1010
TATACCTGCCACGCCAATAACTCAGTCACTGGCTGCAACAGGACCACAGTCAAGACGATC
Tyr Thr Cys His Ala Asn Asn Ser Val Thr Gly Cys Asn Arg Thr Thr Val Lys Thr Ile 1030                       1050                       1070
ATAGTCACTGATAATGCTCTACCACAAGAAAATGGCCTCTCACCTGGGGCCATTGCTGGC
Ile Val Thr Asp Asn Ala Leu Pro Gln Glu Asn Gly Leu Ser Pro Gly Ala Ile Ala Gly 1090                       1110                       1130
ATTGTGATTGGAGTAGTGGCCCTGGTTGCTCTGATAGCAGTAGCCCTGGCATGTTTTCTG
Ile Val Ile Gly Val Val Ala Leu Val Ala Leu Ile Ala Val Ala Leu Ala Cys Phe Leu 1150                       1170                       1190
CATTTCGGGAAGACCGGCAGGGCAAGCGACCAGCGTGATCTCACAGAGCACAAACCCTCA
His Phe Gly Lys Thr Gly Arg Ala Ser Asp Gln Arg Asp Leu Thr Glu His Lys Pro Ser 1210                       1230                       1250
GTCTCCAACCACACTCAGGACCACTCCAATGACCCACCTAACAAGATGAATGAAGTTACT
Val Ser Asn His Thr Gln Asp His Ser Asn Asp Pro Pro Asn Lys Met Asn Glu Val Thr 1270                       1290                       1310
TATTCTACCCTGAACTTTGAAGCCCAGCAACCCACACAACCAACTTCAGCCTCCCCATCC
Tyr Ser Thr Leu Asn Phe Glu Ala Gln Gln Pro Thr Gln Pro Thr Ser Ala Ser Pro Ser
```

-continued

```
                1330                    1350                    1370
CTAACAGCCACAGAAATAATTTATTCAGAAGTAAAAAAGCAGTAATGAAACCTGTCCTGC
Leu Thr Ala Thr Glu Ile Ile Tyr Ser Glu Val Lys Lys Gln 1390                    1410                    1430
TCACTGCAGTGCTGATGTATTTCAAGTCTCTCACCCTCATCACTAGGAGATTCCTTTCCC 1450                    1470                    1490
CTGTAGGGTAGAGGGGTGGGGACAGAAACAACTTTCTCCTTACTCTTCCTTCCTAATAGGC 1510                    1530                    1550
ATCTCCAGGCTGCCTGGTCACTGCCCCTCTCTCAGTGTCAATAGATGAAAGTACATTGGG 1570                    1590                    1610
AGTCTGTAGGAAACCCAACCTTCTTGTCATTGAAATTTGGCAAAGCTGACTTTGGGAAAG 1630                    1650                    1670
AGGGACCAGAACTTCCCCTCCCTTCCCCTTTTCCCAACCTGGACTTGTTTTAAACTTGCC 1690                    1710                    1730
TGTTCAGAGCACTCATTCCTTCCCACCCCCAGTCCTGTCCTATCACTCTAATTCGGATTT 1750                    1770                    1790
GCCATAGCCTTGAGGTTATGTCCTTTTCCATTAAGTACATGTGCCAGGAAACAGCGAGAG 1810                    1830                    1850
AGAGAAAGTAAACGGCAGTAATGCTTCTCCTATTTCTCCAAAGCCTTGTGTGAACTAGCA 1870                    1890                    1910
AAGAGAAGAAAATCAAATATATAACCAATAGTGAAATGCCACAGGTTTGTCCACTGTCAG 1930                    1950                    1970
GGTTGTCTACCTGTAGGATCAGGGTCTAAGCACCTTGGTGCTTAGCTAGAATACCACCTA 1990                    2010                    2030
ATCCTTCTGGCAAGCCTGTCTTCAGAGAACCCACTAGAAGCAACTAGGAAAAATCACTTG 2050                    2070                    2090
CCAAAATCCAAGGCAATTCCTGATGGAAAATGCAAAAGCACATATATGTTTTAATATCTT 2110                    2130                    2150
TATGGGCTCTGTTCAAGGCAGTGCTGAGAGGGAGGGGTTATAGCTTCAGGAGGGAACCAG 2170                    2190                    2210
CTTCTGATAAACACAATCTGCTAGGAACTTGGGAAAGGAATCAGAGAGCTGCCCTTCAGC 2230                    2250                    2270
GATTATTTAAATTGTTAAAGAATACACAATTTGGGGTATTGGGATTTTTCTCCTTTTCTC 2290                    2310                    2330
TGAGACATTCCACCATTTTAATTTTTGTAACTGCTTATTTATGTGAAAAGGGTTATTTTT 2350                    2370                    2390
ACTTAGCTTAGCTATGTCAGCCAATCCGATTGCCTTAGGTGAAAGAAACCACCGAAATCC 2410                    2430                    2450
CTCAGGTCCCTTGGTCAGGAGCCTCTCAAGATTTTTTTTGTCAGAGGCTCCAAATAGAAA 2470                    2490                    2510
ATAAGAAAAGGTTTTCTTCATTCATGGCTAGAGCTAGATTTAACTCAGTTTCTAGGCACC
```

```
                    2530              2550              2570
TCAGACCAATCATCAACTACCATTCTATTCCATGTTTGCACCTGTGCATTTTCTGTTTGC 2590              2610              2630
CCCCATTCACTTTGTCAGGAAACCTTGGCCTCTGCTAAGGTGTATTTGGTCCTTGAGAAG 2650              2670              2690
TGGGAGCACCCTACAGGGACACTATCACTCATGCTGGTGGCATTGTTTACAGCTAGAAAG 2710              2730              2750
CTGCACTGGTGCTAATGCCCCTTGGGAAATGGGGCTGTGAGGAGGAGGATTATAACTTAG 2770              2790              2810
GCCTAGCCTCTTTTAACAGCCTCTGAAATTTATCTTTTCTTCTATGGGGTCTATAAATGT 2830              2850              2870
ATCTTATAATAAAAAGGAAGGACAGGAGGAAGACAGGCAAATGTACTTCTCACCCAGTCT 2890              2910              2930
TCTACACAGATGGAATCTCTTTGGGGCTAAGAGAAAGGTTTTATTCTATATTGCTTACCT 2950              2970              2990
GATCTCATGTTAGGCCTAAGAGGCTTTCTCCAGGAGGATTAGCTTGGAGTTCTCTATACT 3010              3030              3050
CAGGTACCTCTTTCAGGGTTTTCTAACCCTGACACGGACTGTGCATACTTTCCCTCATCC 3070              3090              3110
ATGCTGTGCTGTGTTATTTAATTTTTCCTGGCTAAGATCATGTCTGAATTATGTATGAAA 3130              3150              3170
ATTATTCTATGTTTTTATAATAAAAATAATATATCAGACATCGAAAAAAAAAA
``` which has been designated SEQ ID No:5 and SEQ ID No:13 for the translated polypeptide.

SEQUENCE AND TRANSLATION OF cDNA OF TM-3

```
          10                  30                  50
CAGCCGTGCTCGAAGCGTTCCTGGAGCCCAAGCTCTCCTCCACAGGTGAAGACAGGGCCA 70                  90                 110
GCAGGAGACACCATGGGGCACCTCTCAGCCCCACTTCACAGAGTGCGTGTACCCTGGCAG
               Met Gly His Leu Ser Ala Pro Leu His Arg Val Arg Val Pro Trp Gln 130                 150                 170
GGGCTTCTGCTCACAGCCTCACTTCTAACCTTCTGGAACCCGCCCACCACTGCCCAGCTC
Gly Leu Leu Leu Thr Ala Ser Leu Leu Thr Phe Trp Asn Pro Pro Thr Thr Ala Gln Leu 190                 210                 230
ACTACTGAATCCATGCCATTCAATGTTGCAGAGGGGAAGGAGGTTCTTCTCCTTGTCCAC
Thr Thr Glu Ser Met Pro Phe Asn Val Ala Glu Gly Lys Glu Val Leu Leu Leu Val His 250                 270                 290
AATCTGCCCCAGCAACTTTTTGGCTACAGCTGGTACAAAGGGGAAGAGTGGATGGCAAC
Asn Leu Pro Gln Gln Leu Phe Gly Tyr Ser Trp Tyr Lys Gly Glu Arg Val Asp Gly Asn 310                 330                 350
CGTCAAATTGTAGGATATGCAATAGGAACTCAACAAGCTACCCCAGGGCCCGCAAACAGC
Arg Gln Ile Val Gly Tyr Ala Ile Gly Thr Gln Gln Ala Thr Pro Gly Pro Ala Asn Ser
```

-continued
SEQUENCE AND TRANSLATION OF cDNA OF TM-3

```
        370                      390                      410
GGTCGAGAGACAATATACCCCAATGCATCCCTGCTGATCCAGAACGTCACCCAGAATGAC
Gly Arg Glu Thr Ile Tyr Pro Asn Ala Ser Leu Leu Ile Gln Asn Val Thr Gln Asn Asp 430                      450                      470
ACAGGATTCTACACCCTACAAGTCATAAAGTCAGATCTTGTGAATGAAGAAGCAACTGGA
Thr Gly Phe Tyr Thr Leu Gln Val Ile Lys Ser Asp Leu Val Asn Glu Glu Ala Thr Gly 490                      510                      530
CAGTTCCATGTATACCCGGAGCTGCCCAAGCCCTCCATCTCCAGCAACAACTCCAACCCT
Gln Phe His Val Tyr Pro Glu Leu Pro Lys Pro Ser Ile Ser Ser Asn Asn Ser Asn Pro 550                      570                      590
GTGGAGGACAAGGATGCTGTGGCCTTCACCTGTGAACCTGAGACTCAGGACACAACCTAC
Val Glu Asp Lys Asp Ala Val Ala Phe Thr Cys Glu Pro Glu Thr Gln Asp Thr Thr Tyr 610                      630                      650
CTGTGGTGGATAAACAATCAGAGCCTCCCGGTCAGTCCCAGGCTGCAGCTGTCCAATGGC
Leu Trp Trp Ile Asn Asn Gln Ser Leu Pro Val Ser Pro Arg Leu Gln Leu Ser Asn Gly 670                      690                      710
AACAGGACCCTCACTCTACTCAGTGTCACAAGGAATGACACAGGACCCTATGAGTGTGAA
Asn Arg Thr Leu Thr Leu Leu Ser Val Thr Arg Asn Asp Thr Gly Pro Tyr Glu Cys Glu 730                      750                      770
ATACAGAACCCAGTGAGTGCGAACCGCAGTGACCCAGTCACCTTGAATGTCACCTATGGC
Ile Gln Asn Pro Val Ser Ala Asn Arg Ser Asp Pro Val Thr Leu Asn Val Thr Tyr Gly 790                      810                      830
CCGGACACCCCCACCATTTCCCCTTCAGACACCTATTACCGTCCAGGGGCAAACCTCAGC
Pro Asp Thr Pro Thr Ile Ser Pro Ser Asp Thr Tyr Tyr Arg Pro Gly Ala Asn Leu Ser 850                      870                      890
CTCTCCTGCTATGCAGCCTCTAACCCACCTGCACAGTACTCCTGGCTTATCAATGGAACA
Ser Ser Cys Tyr Ala Ala Ser Asn Pro Pro Ala Gln Tyr Ser Trp Leu Ile Asn Gly Thr 910                      930                      950
TTCCAGCAAAGCACACAAGAGCTCTTTATCCCTAACATCACTGTGAATAATAGTGGATCC
Phe Gln Gln Ser Thr Gln Glu Leu Phe Ile Pro Asn Ile Thr Val Asn Asn Ser Gly Ser 970                      990                      1010
TATACCTGCCACGCCAATAACTCAGTCACTGGCTGCAACAGGACCACAGTCAAGACGATC
Tyr Thr Cys His Ala Asn Asn Ser Val Thr Gly Cys Asn Arg Thr Thr Val Lys Thr Ile 1030                     1050                     1070
ATAGTCACTGAGCTAAGTCCAGTAGTAGCAAAGCCCCAAATCAAAGCCAGCAAGACCACA
Ile Val Thr Glu Leu Ser Pro Val Val Ala Lys Pro Gln Ile Lys Ala Ser Lys Thr Thr 1090                     1110                     1130
GTCACAGGAGATAAGGACTCTGTGAACCTGACCTGCTCCCAAATGACACTGGAATCTCC
Val Thr Gly Asp Lys Asp Ser Val Asn Leu Thr Cys Ser ThrAsn Asp Thr Gly Ile Ser 1150                     1170                     1190
ATCCGTTGGTTCTTCAAAAACCAGAGTCTCCCGTCCTCGGAGAGGATGAAGCTGTCCCAG
Ile Arg Trp Phe Phe Lys Asn Gln Ser Leu Pro Ser Ser Glu Arg Met Lys Leu Ser Gln 1210                     1230                     1250
GGCAACACCACCCTCAGCATAAACCCTGTCAAGAGGGAGGATGCTGGGACGTATTGGTGT
Gly Asn Thr Thr Leu Ser Ile Asn Pro Val Lys Arg Glu Asp Ala Gly Thr Tyr Trp Cys 1270                     1290
GAGGTCTTCAACCCAATCAGTAAGAACCAAAGCGACCCAATCATGCTGAACGTAAACTAT
Glu Val Phe Asn Pro Ile Ser Lys Asn Gln Ser Asp Pro Ile Met Leu Asn Val Asn Tyr
```

SEQUENCE AND TRANSLATION OF cDNA OF TM-3

```
              1330                         1350                        1370
AATGCTCTACCACAAGAAAATGGCCTCTCACCTGGGGCCATTGCTGGCATTGTGATTGGA
Asn Ala Leu Pro Gln Glu Asn Gly Leu Ser Pro Gly Ala Ile Ala Gly Ile Val Ile Gly 1390                        1410                        1430
GTAGTGGCCCTGGTTGCTCTGATAGCAGTAGCCCTGGCATGTTTTCTGCATTTCGGGAAG
Val Val Ala Leu Val Ala Leu Ile Ala Val Ala Leu Ala Cys Phe Leu His Phe Gly Lys 1450                        1470                        1490
ACCGGCAGCTCAGGACCACTCCAATGACCCACCTAACAAGATGAATGAAGTTACTTATTC
Thr Gly Ser Ser Gly Pro Leu Gln 1510                        1530                        1550
TACCCTGAACTTTGAAGCCCAGCAACCCACACAACCAACTTCAGCCTCCCCATCCCTAAC 1570                        1590                        1610
AGCCACAGAAATAATTTATTCAGAAGTAAAAAAGCAGTAATGAAACCTGAAAAAAAAAAA

1630
AAAAAAAAA
``` which has been designated SEQ ID No:6 and SEQ ID No:14 for the translated polypeptide.

SEQUENCE AND TRANSLATION OF cDNA OF TM-4

```
               10                          30                          50
CAGCCGTGCTCGAAGCGTTCCTGGAGCCCAAGCTCTCCTCCACAGGTGAAGACAGGGCCA 70                          90                         110
GCAGGAGACACCATGGGGCACCTCTCAGCCCCACTTCACAGAGTGCGTGTACCCTGGCAG
                  Met Gly His Leu Ser Ala Pro Leu His Arg Val Arg Val Pro Trp Gln 130                         150                         170
GGGCTTCTGCTCACAGCCTCACTTCTAACCTTCTGGAACCCGCCCACCACTGCCCAGCTC
Gly Leu Leu Leu Thr Ala Ser Leu Leu Thr Phe Trp Asn Pro Pro Thr Thr Ala Gln Leu 190                         210                         230
ACTACTGAATCCATGCCATTCAATGTTGCAGAGGGGAAGGAGGTTCTTCTCCTTGTCCAC
Thr Thr Glu Ser Met Pro Phe Asn Val Ala Glu Gly Lys Glu Val Leu Leu Leu Val His 250                         270                         290
AATCTGCCCCAGCAACTTTTTTGGCTACAGCTGGTACAAAGGGGAAAGAGTGGATGGCAAC
Asn Leu Pro Gln Gln Leu Phe Gly Tyr Ser Trp Tyr Lys Gly Glu Arg Val Asp Gly Asn 310                         330                         350
CGTCAAATTGTAGGATATGCAATAGGAACTCAACAAGCTACCCCAGGGCCCGCAAACAGC
Arg Gln Ile Val Gly Tyr Ala Ile Gly Thr Gln Gln Ala Thr Pro Gly Pro Ala Asn Ser 370                         390                         410
GGTCGAGAGACAATATACCCCAATGCATCCCTGCTGATCCAGAACGTCACCCAGAATGAC
Gly Arg Glu Thr Ile Tyr Pro Asn Ala Ser Leu Leu Ile Gln Asn Val Thr Gln Asn Asp 430                         450                         470
ACAGGATTCTACACCCTACAAGTCATAAAGTCAGATCTTGTGAATGAAGAAGCAACTGGA
Thr Gly Phe Tyr Thr Leu Gln Val Ile Lys Ser Asp Leu Val Asn Glu Glu Ala Thr Gly 490                         510                         530
CAGTTCCATGTATACCCGGAGCTGCCCAAGCCCTCCATCTCCAGCAACAACTCCAACCCT
Gln Phe His Val Tyr Pro Glu Leu Pro Lys Pro Ser Ile Ser Ser Asn Asn Ser Asn Pro
```

SEQUENCE AND TRANSLATION OF cDNA OF TM-4
-continued

```
          550                          570                          590
GTGGAGGACAAGGATGCTGTGGCCTTCACCTGTGAACCTGAGACTCAGGACACAACCTAC
Val Glu Asp Lys Asp Ala Val Ala Phe Thr Cys Glu Pro Glu Thr Gln Asp Thr Thr Tyr 610                          630                          650
CTGTGGTGGATAAACAATCAGAGCCTCCCGGTCAGTCCCAGGCTGCAGCTGTCCAATGGC
Leu Trp Trp Ile Asn Asn Gln Ser Leu Pro Val Ser Pro Arg Leu Gln Leu Ser Asn Gly 670                          690                          710
AACAGGACCCTCACTCTACTCAGTGTCACAAGGAATGACACAGGACCCTATGAGTGTGAA
Asn Arg Thr Leu Thr Leu Leu Ser Val Thr Arg Asn Asp Thr Gly Pro Tyr Glu Cys Glu 730                          750                          770
ATACAGAACCCAGTGAGTGCGAACCGCAGTGACCCAGTCACCTTGAATGTCACCTATGGC
Ile Gln Asn Pro Val Ser Ala Asn Arg Ser Asp Pro Val Thr Leu Asn Val Thr Tyr Gly 790                          810                          830
CCGGACACCCCCACCATTTCCCCTTCAGACACCTATTACCGTCCAGGGGCAAACCTCAGC
Pro Asp Thr Pro Thr Ile Ser Pro Ser Asp Thr Tyr Tyr Arg Pro Gly Ala Asn Leu Ser 850                          870                          890
CTCTCCTGCTATGCAGCCTCTAACCCACCTGCACAGTACTCCTGGCTTATCAATGGAAGC
Leu Ser Cys Tyr Ala Ala Ser Asn Pro Pro Ala Gln Tyr Ser Trp Leu Ile Asn Gly Thr 910                          930                          950
TTCCAGCAAAGCACACAAGAGCTCTTTATCCCTAACATCACTGTGAATAATAGTGGATCC
Phe Gln Gln Ser Thr Gln Glu Leu Phe Ile Pro Asn Ile Thr Val Asn Asn Ser Gly Ser 970                          990                         1010
TATACCTGCCACGCCAATAACTCAGTCACTGGCTGCAACAGGACCACAGTCAAGACGATC
Tyr Thr Cys His Ala Asn Asn Ser Val Thr Gly Cys Asn Arg Thr Thr Val Lys Thr Ile 1030                         1050                         1070
ATAGTCACTGATAATGCTCTACCACAAGAAAATGGCCTCTCACCTGGGGCCATTGCTGGC
Ile Val Thr Asp Asn Ala Leu Pro Gln Glu Asn Gly Leu Ser Pro Gly Ala Ile Ala Gly 1090                         1110                         1130
ATTGTGATTGGAGTAGTGGCCCTGGTTGCTCTGATAGCAGTAGCCCTGGCATGTTTTCTG
Ile Val Ile Gly Val Val Ala Leu Val Ala Leu Ile Ala Val Ala Leu Ala Cys Phe Leu 1150                         1170                         1190
CATTTCGGGAAGACCGGCAGCTCAGGACCACTCCAATGACCCACCTAACAAGATGAATGA
His Phe Gly Lys Thr Gly Ser Ser Gly Pro Leu Gln 1210                         1230                         1250
AGTTACTTATTCTACCCTGAACTTTGAAGCCCAGCAACCCACACAACCAACTTCAGCCTC 1290                         1310
CCCATCCCTAACAGCCACAGAAATAATTTATTCAGAAGTAAAAAAGCAGTAATGAAACCT

1330
GAAAAAAAAAAAAAAAAA
``` which has been designated SEQ ID No:7 and SEQ ID No:15 for the translated polypeptide.

The present invention is also directed to a replicable recombinant cloning vehicle ("vector") having an insert comprising a nucleic acid, e.g., DNA, which comprises a base sequence which codes for a CEA peptide or a base sequence hybridizable therewith.

This invention also relates to a cell that is transformed/transfected, infected or injected with the above described replicable recombinant cloning vehicle or nucleic acid hybridizable with the aforementioned cDNA. Thus the invention also concerns the transfection of cells using free nucleic acid, without the use of a cloning vehicle.

Still further, the present invention concerns a polypeptide expressed by the above described transfected, infected or injected cell, which polypeptide exhibits immunological cross-reactivity with a cEA, as well as labelled forms of the polypeptide. The invention also relates to polypeptides having an amino acid sequence, i.e., synthetic peptides, or the expression product of a cell that is transfected, injected, infected with the above described replicable recombinant cloning vehicles, as well as labelled forms thereof. Stated otherwise, the present invention concerns a synthetic peptide having an amino acid sequence corresponding to the entire amino acid sequence or a portion thereof having no less than five amion acids of the aforesaid expression product.

The invention further relates to an antibody preparation specific for the above described polypeptide.

Another aspect of the invention concerns an immunoassay method for detecting CEA or a functional equivalent thereof in a test sample comprising (a) contacting the sample with the above described antibody preparation, and (b) determining binding thereof to CEA in the sample.

The invention also is directed to a nucleic acid hybridization method for detecting a CEA or a related nucleic acid (DNA or RNA) sample in a test sample comprising (a) contacting the test sample with a nucleic acid probe comprising a nucleic acid, which comprises a base sequence which codes for a CEA peptide sequence or a base sequence that is hybridizable therewith, and (b) determining the formation of the resultant hybridized probe.

The present invention also concerns a method for detecting the presence of carcinoembryonic antigen or a functional equivalent thereof in an animal or human patient in vivo comprising a) introducing into said patient a labeled (e.g., a radioopaque material that can be detected by X-rays, radiolabeled or labeled with paramagnetic materials that can be detected by NMR) antibody preparation according to the present invention and b) detecting the presence of such antibody preparation in the patient by detecting the label.

In another aspect, the present invention relates to the use of an antibody preparation according to the present invention for therapeutic purposes, namely, attaching to an antibody preparation radionuclides, toxins or other biological effectors to form a complex and introducing an effective amount of such complex into an animal or human patient, e.g., by injection or orally. The antibody complex would attach to CEA in a patient and the radionuclide, toxin or other biological effector would serve to destroy the CEA expressing cell.

BRIEF DESCRIPTION OF THE DRAWINGS

FIG. 1 consists of four schematic representations (FIGS. 1A–1D) of the transmembrane CEA's, wherein:

DETAILED DESCRIPTION OF THE INVENTION

Figure 1A:
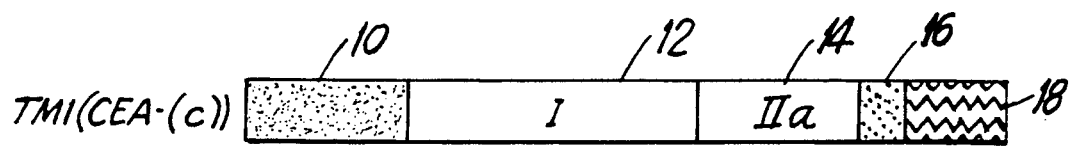
FIG. 1A is a schematic representation of TM1 (CEA-(c))

In parent applications, applicants described the following CEA's:

|         |                         | ATCC No. |
|---------|-------------------------|----------|
| CEA-(a) | partial CEA (pcLV7)     |          |
| CEA-(b) | full coding CEA (pc 15LV7) | 67709 |
| CEA-(c) | TM-1 (FL-CEA; pc 19-22) | 67710    |
| CEA-(d) | NCA (pcBT 20)           | 67711    |

In the present application, applicants described the following CEA's:

|         |              | ATCC No. |
|---------|--------------|----------|
| CEA-(e) | TM-2 (pc E22) | 67712   |
| CEA-(f) | TM-3 (pc HT-6) | 67708  |
| CEA-(g) | TM-4.        |          |

ATCC Nos. 67708, 67709, 67710, 67711 and 67712 were all deposited with the America Type Culture Collection on May 25, 1988.

The sequences for CEA-(a), CEA-(b), CEA-(c) and CEA-(d) are given hereinbelow: CEA-(a):

```
GG GGT TTA CAC AAC CAC CAC CCC ATC AAA CCC TTC ATC ACC AGC AAC AAC TCC AAC CCC GTG
   GAG GAT GAG GAT GCT GTA GCC TTA ACC TGT GAA CCT GAG ATT CAG AAC ACA ACC TAC CTG
   TGG TGG GTA AAT AAT CAG AGC CTC CCG GTC AGT CCC AGG CTG CAG CTG TCC AAT GAC AAC
   AGG ACC CTC ACT CTA CTC AGT GTC ACA AGG AAT GAT GTA GGA CCC TAT GAG TGT GGA ATC
   CAG AAC GAA TTA AGT GTT GAC CAC AGC GAC CCA GTC ACC CAG CGA TTC CTC TAT GGC CCA
   GAC GAC CCC ACC ATT TCC CCC TCA TAC ACC TAT TAC CGT CCA GGG GTG GAA OCT CAG CCT
   CTC TGC CAT GCA GCC TCT AAC CCA CCT GCA CAG TAT TCT TGG CTG ATT GAT GGG ACC GTC
   CAG CAA CAC ACA CAA GAG CTC TTT ATC TCC AAC ATC ACT GAG AAG AAC AGC GGA CTC TAT
   ACC TGC CAG GCC AAT AAC TCA GCC AGT GGC ACA GCA GGA CTA CAG TCA AGA CAA TCA CAG
   TCT CTG CGG ATG CCC AAG CCC TCC ATC TCC AGC AAC AAC TCC AAA CCC GTG GAG GAC AAG
   GAT CGC TGT TGC CTT CAC TGT GAA CCT GAG GCT CAG AAC ACA ACC TAC CTG TGG TGG GTA
   AAT GGT CAG AGC CTC CCA GTC AGT CCC AGG CTG CAG CTG TCC AAT GGC AAC AGG ACC CTC
   ACT CTA TTC AAT GTC ACA AGA AAT GAC GCA AGA GCC TAT GTA TGT GGA ATC CAG AAC TCA
   GTG AGT GCA AAC CGC AGT GAC CCA GTC ACC CTG GAT GTC CTC TAT GGG CCG GAC ACC CCC
   ATC ATT TCC CCC CCC CC
``` which has been designated SEQ ID No:1.

DEA-(b):

```
                    10                              30                          50
CACCATGGAGTCTCCCTCGGCCCCTCCCCACAGATGGTGCATCCCCTGGCAGAGGCTCCTG
Met Glu Ser Pro Ser Ala Pro Pro His Arg Trp Cys Ile Pro Trp Gln Arg Leu Leu
```

-continued

```
           70                     90                     110
CTCACAGCCTCACTTCTAACCTTCTGGAACCCGCCCACCACTGCCAAGCTCACTATTGAA
Leu Thr Ala Ser Leu Leu Thr Phe Trp Asn Pro Pro Thr Thr Ala Lys Leu Thr Ile  Glu 130                    150                    170
TCCACGCCGTTCAATGTCGCAGAGGGGAAGGAGGTGCTTCTACTTGTCCACAATCTGCCC
Ser Thr Pro Phe Asn Val Ala Glu Gly Lys Glu Val Leu Leu Leu Val His Asn Leu Pro 190                    210                    230
CAGCATCTTTTTGGCTACAGCTGGTACAAAGGTGAAAGAGTGGATGGCAACCGTCAAATT
Gln His Leu Phe Gly Tyr Ser Trp Tyr Lys Gly Glu Arg Val Asp Gly Asn Arg Gln Ile 250                    270                    290
ATAGGATATGTAATAGGAACTCAACAAGCTACCCCAGGGCCCGCATACAGTGGTCGAGAG
Ile Gly Tyr Val Ile Gly Thr Gln Gln Ala Thr Pro Gly Pro Ala Tyr Ser Gly Arg Glu 310                    330                    350
ATAATATACCCCAATGCATCCCTGCTGATCCAGAACATCATCCAGAATGACACAGGATTC
Ile Ile Tyr Pro Asn Ala Ser Leu Leu Ile Gln Asn Ile Ile Gln Asn Asp Thr Gly Phe 370                    390                    410
TACACCCTACACGTCATAAAGTCAGATCTTGTGAATGAAGAAGCAACTGGCCAGTTCCGG
Tyr Thr Leu His Val Ile Lys Ser Asp Leu Val Asn Glu Glu Ala Thr Gly Gln Phe Arg 430                    450                    470
GTATACCCGGAGCTGCCCAAGCCCTCCATCTCCAGCAACAACTCCAAACCCGTGGAGGAC
Val Tyr Pro Glu Leu Pro Lys Pro Ser Ile Ser Ser Asn Asn Ser Lys Pro Val Glu Asp 490                    510                    530
AAGGATGCTGTGGCCTTCACCTGTGAACCTGAGACTCAGGACGCAACCTACCTGTGGTGG
Lys Asp Ala Val Ala Phe Thr Cys Glu Pro Glu Thr Gln Asp Ala Thr Tyr Leu Trp Trp 550                    570                    590
GTAAACAATCAGAGCCTCCCGGTCAGTCCCAGGCTGCAGCTGTCCAATGGCAACAGGACC
Val Asn Asn Gln Ser Leu Pro Val Ser Pro Arg Leu Gln Leu Ser Asn Gly Asn Arg Thr 610                    630                    650
CTCACTCTATTCAATGTCACAAGAAATGACACAGCAAGCTACAAATGTGAAACCCAGAAC
Leu Thr Leu Phe Asn Val Thr Arg Asn Asp Thr Ala Ser Tyr Lys Cys Glu Thr Gln Asn 670                    690                    710
CCAGTGAGTGCCAGGCGCAGTGATTCAGTCATCCTGAATGTCCTCTATGGCCCGGATGCC
Pro Val Ser Ala Arg Arg Ser Asp Ser Val Ile Leu Asn Val Leu Tyr Gly Pro Asp Ala 730                    750                    770
CCCACCATTTCCCCTCTAAACACATCTTACAGATCAGGGGAAAATCTGAACCTCTCCTGC
Pro Thr Ile Ser Pro Leu Asn Thr Ser Tyr Arg Ser Gly Glu Asn Leu Asn Leu Ser Cys 790                    810                    830
CACGCAGCCTCTAACCCACCTGCACAGTACTCTTGGTTTGTCAATGGGACTTTCCAGCAA
His Ala Ala Ser Asn Pro Pro Ala Gln Tyr Ser Trp Phe Val Asn Gly Thr Phe Gln Gln 850                    870                    890
TCCACCCAAGAGCTCTTTATCCCCAACATCACTGTGAATAATAGTGGATCCTATACGTGC
Ser Thr Gln Glu Leu Phe Ile Pro Asn Ile Thr Val Asn Asn Ser Gly Ser Tyr Thr Cys

910                  · 930                    950
CAAGCCCATAACTCAGACACTGGCCTCAATAGGACCACAGTCACGACGATCACAGTCTAT
Gln Ala His Asn Ser Asp Thr Gly Leu Asn Arg Thr Thr Val Thr Thr Ile Thr Val Tyr 970                    990                   1010
GCAGAGCCACCCAAACCCTTCATCACCAGCAACAACTCCAACCCCGTGGAGGATGAGGAT
Ala Glu Pro Pro Lys Pro Phe Ile Thr Ser Asn Asn Ser Asn Pro Val Glu Asp Glu Asp
```

```
                1030                          1050                         1070
GCTGTAGCCTTAACCTGTGAACCTGAGATTCAGAACACAACCTACCTGTGGTGGGTAAAT
Ala Val Ala Leu Thr Cys Glu Pro Glu Ile Gln Asn Thr Thr Tyr Leu Trp Trp Val Asn 1090                          1110                         1130
AATCAGAGCCTCCCGGTCAGTCCCAGGCTGCAGCTGTCCAATGACAACAGGACCCTCACT
Asn Gln Ser Leu Pro Val Ser Pro Arg Leu Gln Leu Ser Asn Asp Asn Arg Thr Leu Thr 1150                          1170                         1190
CTACTCAGTGTCACAAGGAATGATGTAGGACCCTATGAGTGTGGAATCCAGAACGAATTA
Leu Leu Ser Val Thr Arg Asn Asp Val Gly Pro Tyr Glu Cys Gly Ile Gln Asn Glu Leu 1210                          1230                         1250
AGTGTTGACCACAGCGACCCAGTCATCCTGAATGTCCTCTATGGCCCAGACGACCCCACC
Ser Val Asp His Ser Asp Pro Val Ile Leu Asn Val Leu Tyr Gly Pro Asp Asp Pro Thr 1270                          1290                         1310
ATTTCCCCCTCATACACCTATTACCGTCCAGGGGTGAACCTCAGCCTCTCCTGCCATGCA
Ile Ser Pro Ser Tyr Thr Tyr Tyr Arg Pro Gly Val Asn Leu Ser Leu Ser Cys His Ala 1330                          1350                         1370
GCCTCTAACCCACCTGCACAGTATTCTTGGCTGATTGATGGGAACATCCAGCAACACACA
Ala Ser Asn Pro Pro Ala Gln Tyr Ser Trp Leu Ile Asp Gly Asn Ile Gln Gln His Thr 1390                          1410                         1430
CAAGAGCTCTTTATCTCCAACATCACTGAGAAGAACAGCGGACTCTATACCTGCCAGGCC
Gln Glu Leu Phe Ile Ser Asn Ile Thr Glu Lys Asn Ser Gly Leu Tyr Thr Cys Gln Ala 1450                          1470                         1490
AATAACTCAGCCAGTGGCCACAGCAGGACTACAGTCAAGACAATCACAGTCTCTGCGGAG
Asn Asn Ser Ala Ser Gly His Ser Arg Thr Thr Val Lys Thr Ile Thr Val Ser Ala Glu 1510                          1530                         1550
CTGCCCAAGCCCTCCATCTCCAGCAACAACTCCAAACCCGTGGAGGACAAGGATGCTGTG
Leu Pro Lys Pro Ser Ile Ser Ser Asn Asn Ser Lys Pro Val Glu Asp Lys Asp Ala Val 1570                          1590                         1610
GCCTTCACCTGTGAACCTGAGGCTCAGAACACAACCTACCTGTGGTGGGTAAATGGTCAG
Ala Phe Thr Cys Glu Pro Glu Ala Gln Asn Thr Thr Tyr Leu Trp Trp Val Asn Gly Gln 1630                          1650                         1670
AGCCTCCCAGTCAGTCCCAGGCTGCAGCTGTCCAATGGCAACAGGACCCTCACTCTATTC
Ser Leu Pro Val Ser Pro Arg Leu Gln Leu Ser Asn Gly Asn Arg Thr Leu Thr Leu Phe 1690                          1710                         1730
AATGTCACAAGAAATGACGCAAGAGCCTATGTATGTGGAATCCAGAACTCAGTGAGTGCA
Asn Val Thr Arg Asn Asp Ala Arg Ala Tyr Val Cys Gly Ile Gln Asn Ser Val Ser Ala 1750                          1770                         1790
AACCGCAGTGACCCAGTCACCCTGGATGTCCTCTATGGGCCGGACACCCCCATCATTTCC
Asn Arg Ser Asp Pro Val Thr Leu Asp Val Leu Tyr Gly Pro Asp Thr Pro Ile Ile Ser 1810                          1830                         1850
CCCCCAGACTCGTCTTACCTTTCGGGAGCGAACCTCAACCTCTCCTGCCACTCGGCCTCT
Pro Pro Asp Ser Ser Tyr Leu Ser Gly Ala Asn Leu Asn Leu Ser Cys His Ser Ala Ser 1870                          1890                         1910
AACCCATCCCCGCAGTATTCTTGGCGTATCAATGGGATACCGCAGCAACACACACAAGTT
Asn Pro Ser Pro Gln Tyr Ser Trp Arg Ile Asn Gly Ile Pro Gln Gln His Thr Gln Val 1930                          1950                         1970
CTCTTTATCGCCAAAATCACGCCAAATAATAACGGGACCTATGCCTGTTTTGTCTCTAAC
Leu Phe Ile Ala Lys Ile Thr Pro Asn Asn Asn Gly Thr Tyr Ala Cys Phe Val Ser Asn
```

-continued

```
                1990                          2010                        2030
TTGGCTACTGGCCGCAATAATTCCATAGTCAAGAGCATCACAGTCTCTGCATCTGGAACT
Leu Ala Thr Gly Arg Asn Asn Ser Ile  Val Lys Ser Ile  Thr Val Ser Ala Ser Gly Thr 2050                          2070                        2090
TCTCCTGGTCTCTCAGCTGGGGCCACTGTCGGCATCATGATTGGAGTGCTGGTTGGGGTT
Ser Pro Gly Leu Ser Ala Gly  Ala Thr Val Gly Ile  Met Ile  Gly Val Leu Val Gly Val 2110                          2130                        2150
GCTCTGATATAGCAGCCCTGGTGTAGTTTCTTCATTTCAGGAAGACTGACAGTTGTTTTG
Ala Leu Ile End 2170                          2190                        2210
CTTCTTCCTTAAAGCATTTGCAACAGCTACAGTCTAAAATTGCTTCTTTACCAAGGATAT 2230                          2250                        2270
TTACAGAAAAGACTCTGACCAGAGATCGAGACCATCCTAGCCAACATCGTGAAACCCCAT 2290                          2310                        2330
CTCTACTAAAAATACAAAAATGAGCTGGGCTTGGTGGCGCGCACCTGTAGTCCCAGTTAC 2350                          2370                        2390
TCGGGAGGCTGAGGCAGGAGAATCGCTTGAACCCGGGAGGTGGAGATTGCAGTGAGCCCA 2410                          2430                        2450
GATCGCACCACTGCACTCCAGTCTGGCAACAGAGCAAGACTCCATCTCAAA
``` which has been designated SEQ ID No.2 and SEQ ID
No:10 for the translated polypeptide.

CEA-(c):

```
           10                           30                          50
CAGCCGTGCTCGAAGCGTTCCTGGAGCCCAAGCTCTCCTCCACAGGTGAAACAGGCCA 70                           90                          110
GCAGGAGACACCATGGGGCACCTCTCAGCCCCACTTCACAGAGTGCGTGTACCCTGGCAG
              Met Gly His Leu Ser Ala Pro Leu His Arg Val Arg Val Pro Trp Gln 130                          150                         170
GGGCTTCTGCTCACAGCCTCACTTCTAACCTTCTGGAACCCGCCCACCACTGCCCAGCTC
Gly Leu Leu Leu Thr Ala Ser Leu Leu Thr Phe Trp Asn Pro Pro Thr Thr Ala Gln Leu 190                          210                         230
ACTACTGAATCCATGCCATTCAATGTTGCAGAGGGGAAGGAGGTTCTTCTCCTTGTCCAC
Thr Thr Glu Ser Met Pro Phe Asn Val Ala Glu Gly Lys Glu Val Leu Leu Leu Val His 250                          270                         290
AATCTGCCCCAGCAACTTTTTGGCTACAGCTGGTACAAAGGGGAAAGAGTGGATGGCAAC
Asn Leu Pro Gln Gln Leu Phe Gly Tyr Ser Trp Tyr Lys Gly Glu Arg Val Asp Gly Asn 310                          330                         350
CGTCAAATTGTAGGATATGCAATAGGAACTCAACAAGCTACCCCAGGGCCCGCAAACAGC
Arg Gln Ile  Val Gly Tyr Ala Ile  Gly Thr Gln Gln A! Thr Pro Gly Pro Ala Asn Ser 370                          390                         410
GGTCGAGAGACAATATACCCCAATGCATCCCTGCTGATCCAGAACGTCACCCAGAATGAC
Gly Arg Glu Thr Ile  Tyr Pro Asn Ala Ser Leu Leu Ile  Gln Asn Val Thr Gln Asn Asp 430                          450                         470
ACAGGATTCTACACCCTACAAGTCATAAAGTCAGATCTTGTGAATGAAGAAGCAACTGGA
Thr Gly Phe Tyr Thr Leu Gln Val Ile  Lys Ser Asp Leu Val Asn Glu Glu Ala Thr Gly 490                          510                         530
CAGTTCCATGTATACCCGGAGCTGCCCAAGCCCTCCATCTCCAGCAACAACTCCAACCCT
Gln Phe His Val Tyr Pro Glu Leu Pro Lys Pro Ser Ile  Ser Ser Asn Asn Ser Asn Pro
```

```
       550                          570                           590
GTGGAGGACAAGGATGCTGTGGCCTTCACCTGTGAACCTGAGACTCAGGACACAACCTAC
Val Glu Asp Lys Asp Ala Val Ala Phe Thr Cys Glu Pro Glu Thr Gln Asp Thr Thr Tyr 610                          630                           650
CTGTGGTGGATAAACAATCAGAGCCTCCCGGTCAGTCCCAGGCTGCAGCTGTCCAATGGC
Leu Trp Trp Ile Asn Asn Gln Ser Leu Pro Val Ser Pro Arg Leu Gln Leu Ser Asn Gly 670                          690                           710
AACAGGACCCTCACTCTACTCAGTGTCACAAGGAATGACACAGGACCCTATGAGTGTGAA
Asn Arg Thr Leu Thr Leu Leu Ser Val Thr Arg Asn Asp Thr Gly Pro Tyr Glu Cys Glu 730                          750                           770
ATACAGAACCCAGTGAGTGCGAACCGCAGTGACCCAGTCACCTTGAATGTCACCTATGGC
Ile Gln Asn Pro Val Ser Ala Asn Arg Ser Asp Pro Val Thr Leu Asn Val Thr Tyr Gly 790                          810                           830
CCGGACACCCCCACCATTTCCCCTTCAGACACCTATTACCGTCCAGGGGCAAACCTCAGC
Pro Asp Thr Pro Thr Ile Ser Pro Ser Asp Thr Tyr Tyr Arg Pro Gly Ala Asn Leu Ser 850                          870                           890
CTCTCCTGCTATGCAGCCTCTAACCCACCTGCACAGTACTCCTGGCTTATCAATGGAACA
Leu Ser Cys Tyr Ala Ala Ser Asn Pro Pro Ala Gln Tyr Ser Trp Leu Ile Asn Gly Thr 910                          930                           950
TTCCAGCAAAGCACACAAGAGCTCTTTATCCCTAACATCACTGTGAATAATAGTGGATCC
Phe Gln Gln Ser Thr Gln Glu Leu Phe Ile Pro Asn Ile Thr Val Asn Asn Ser Gly Ser 970                          990                          1010
TATACCTGCCACGCCAATAACTCAGTCACTGGCTGCAACAGGACCACAGTCAAGACGATC
Tyr Thr Cys His Ala Asn Asn Ser Val Thr Gly Cys Asn Arg Thr Thr Val Lys Thr Ile 1030                         1050                          1070
ATAGTCACTGAGCTAAGTCCAGTAGTAGCAAAGCCCCAAATCAAAGCCAGCAAGACCACA
Ile Val Thr Glu Leu Ser Pro Val Val Ala Lys Pro Gln Ile Lys Ala Ser Lys Thr Thr 1090                         1110                          1130
GTCACAGGAGATAAGGACTCTGTGAACCTGACCTGCTCCACAAATGACACTGGAATCTCC
Val Thr Gly Asp Lys Asp Ser Val Asn Leu Thr Cys Ser Thr Asn Asp Thr Gly Ile Ser 1150                         1170                          1190
ATCCGTTGGTTCTTCAAAAACCAGAGTCTCCCGTCCTCGGAGAGGATGAAGCTGTCCCAG
Ile Arg Trp Phe Phe Lys Asn Gln Ser Leu Pro Ser Ser Glu Arg Met Lys Leu Ser Gln 1210                         1230                          1250
GGCAACACCACCCTCAGCATAAACCCTGTCAAGAGGGAGGATGCTGGGACGTATTGGTGT
Gly Asn Thr Thr Leu Ser Ile Asn Pro Val Lys Arg Glu Asp Ala Gly Thr Tyr Trp Cys 1270                         1290                          1310
GAGGTCTTCAACCCAATCAGTAAGAACCAAAGCGACCCCATCATGCTGAACGTAAACTAT
Glu Val Phe Asn Pro Ile Ser Lys Asn Gln Ser Asp Pro Ile Met Leu Asn Val Asn Tyr 1330                         1350                          1370
AATGCTCTACCACAAGAAAATGGCCTCTCACCTGGGGCCATTGCTGGCATTGTGATTGGA
Asn Ala Leu Pro Gln Glu Asn Gly Leu Ser Pro Gly Ala Ile Ala Gly Ile Val Ile Gly 1390                         1410                          1430
GTAGTGGCCCTGGTTGCTCTGATAGCAGTAGCCCTGGCATGTTTTCTGCATTTCGGGAAG
Val Val Ala Leu Val Ala Leu Ile Ala Val Ala Leu Ala Cys Phe Leu His Phe Gly Lys 1450                         1470                          1490
ACCGGCAGGGCAAGCGACCAGCGTGATCTCACAGAGCACAAACCCTCAGTCTCCAACCAC
Thr Gly Arg Ala Ser Asp Gln Arg Asp Leu Thr Glu His Lys Pro Ser Val Ser Asn His 1510                         1530                          1550
```

-continued

```
ACTCAGGACCACTCCAATGACCCACCTAACAAGATGAATGAAGTTACTTATTCTACCCTG
Thr Gln Asp His Ser Asn Asp Pro Pro Asn Lys Met Asn Glu Val Thr Tyr Ser Thr Leu
         1570                    1590                    1610

AACTTTGAAGCCCAGCAACCCACACAACCAACTTCAGCCTCCCCATCCCTAACAGCCACA
Asn Phe Glu Ala Gln Gln Pro Thr Gln Pro Thr Ser Ala Ser Pro Ser Leu Thr Ala Thr
         1630                    1650                    1670

GAAATAATTTATTCAGAAGTAAAAAAGCAGTAATGAAACCTGTCCTGCTCACTGCAGTGC
Glu Ile Ile Tyr Ser Glu Val Lys Lys Gln
         1690                    1710                    1730

TGATGTATTTCAAGTCTCTCACCCTCATCACTAGGAGATTCCTTTCCCCTGTAGGGTAGA
         1750                    1770                    1790

GGGGTGGGGACAGAAACAACTTTCTCCTACTCTTCCTTCCTAATAGGCATCTCCAGGCTG
         1810                    1830                    1850

CCTGGTCACTGCCCCTCTCTCAGTGTCAATAGATGAAAGTACATTGGGAGTCTGTAGGAA
         1870                    1890                    1910

ACCCAACCTTCTTGTCATTGAAATTTGGCAAAGCTGACTTTGGGAAAGAGGGACCAGAAC
         1930                    1950                    1970

TTCCCCTCCCTTCCCCTTTTCCCAACCTGGACTTGTTTTAAACTTGCCTGTTCAGAGCAC
         1990                    2010                    2030

TCATTCCTTCCCACCCCCAGTCCTGTCCTATCACTCTAATTCGGATTTGCCATAGCCTTG
         2050                    2070                    2090

AGGTTATGTCCTTTTCCATTAAGTACATGTGCCAGGAAACAGCGAGAGAGAGAAAGTAAA
         2110                    2130                    2150

CGGCAGTAATGCTTCTCCTATTTCTCCAAAGCCTTGTGTGAACTAGCAAAGAGAAGAAAA
         2170                    2190                    2210

TCAAATATATAACCAATAGTGAAATGCCACAGGTTTGTCCACTGTCAGGGTTGTCTACCT
         2230                    2250                    2270

GTAGGATCAGGGTCTAAGCACCTTGGTGCTTAGCTAGAATACCACCTAATCCTTCTGGCA
         2290                    2310                    2330

AGCCTGTCTTCAGAGAACCCACTAGAAGCAACTAGGAAAAATCACTTGCCAAAATCCAAG
         2350                    2370                    2390

GCAATTCCTGATGGAAAATGCAAAAGCACATATATGTTTTAATATCTTTATGGGCTCTGT
         2410                    2430                    2450

TCAAGGCAGTGCTGAGAGGGAGGGGTTATAGCTTCAGGAGGGAACCAGCTTCTGATAAAC
         2470                    2490                    2510

ACAATCTGCTAGGAACTTGGGAAAGGAATCAGAGAGCTGCCCTTCAGCGATTATTTAA.T
         2530                    2550                    2570

TGTTAAAGAATACACAATTTGGGGTATTGGGATTTTTCTCCTTTTCTCTGAGACATTCCA
         2590                    2610                    2630

CCATTTTAATTTTTGTAACTGCTTATTTATGTGAAAAGGGTTATTTTTACTTAGCTTAGC
         2650                    2670                    2690

TATGTCAGCCAATCCGATTGCCTTAGGTGAAAGAAACCACCGAAATCCCTCAGGTCCCTT
         2710                    2730                    2750
```

-continued

```
GGTCAGGAGCCTCTCAAGATTTTTTTTGTCAGAGGCTCCAAATAGAAAATAAGAAAAGGT
         2770                2790                2810
TTTCTTCATTCATGGCTAGAGCTAGATTTAACTCAGTTTCTAGGCACCTCAGACCAATCA
         2830                2850                2870
TCAACTACCATTCTATTCCATGTTTGCACCTGTGCATTTTCTGTTTGCCCCCATTCACTT
         2890                2910                2930
TGTCAGGAAACCTTGGCCTCTGCTAAGGTGTATTTGGTCCTTGAGAAGTGGGAGCACCCT
         2950                2970                2990
ACAGGGACACTATCACTCATGCTGGTGGCATTGTTTACAGCTAGAAAGCTGCACTGGTGC
         3010                3030                3050
TAATGCCCCTTGGGAAATGGGGCTGTGAGGAGGAGGATTATAACTTAGGCCTAGCCTCTT
         3070                3090                3110
TTAACAGCCTCTGAAATTTATCTTTTCTTCTATGGGGTCTATAAATGTATCTTATAATAA
         3130                3150                3170
AAAGGAAGGACAGGAGGAAGACAGGCAAATGTACTTCTCACCCAGTCTTCTACACAGATG
         3190                3210                3230
GAATCTCTTTGGGGCTAAGAGAAAGGTTTTATTCTATATTGCTTACCTGATCTCATGTTA
         3250                3270                3290
GGCCTAAGAGGCTTTCTCCAGGAGGATTAGCTTGGAGTTCTCTATACTCAGGTACCTCTT
         3310                3330                3350
TCAGGGTTTTCTAACCCTGACACGGACTGTGCATACTTTCCCTCATCCATGCTGTGCTGT
         3370                3390                3410
GTTATTTAATTTTTCGTGGCTAAGATCATGTCTGAATTATGTATGAAAATTATTCTATGT
         3430                3450
TTTTATAATAAAAATAATATATCAGACATCGAAAAAAAAAA
``` which has been designated SEQ ID No.3 and SEQ ID
No:11 for the translated polypeptide.

A-(d):

```
           10                 30                 50
CCGGGGGACACGCAGGGCCAACAGTCACAGCAGCCCTGACCAGAGCATTCCTGGAGCTCAAG
           70                 90                110
CTCTCTACAAAGAGGTGGACAGAGAAGACAGCAGAGACCATGGGACCCCCCTCAGCCCCT
                                              Met Gly Pro Pro Ser Ala Pro
          130                150                170
CCCTGCAGATTGCATGTCCCCTGGAAGGAGGTCCTGCTCACAGCCTCACTTCTAACCTTC
Pro Cys Arg Leu His Val Pro Trp Lys Glu Val Leu Leu Thr Ala Ser Leu Leu Thr Phe
          190                210                230
TGGAACCCACCCACCACTGCCAAGCTCACTATTGAATCCACGCCATTCAATGTCGCAGAG
Trp Asn Pro Pro Thr Thr Ala Lys Leu Thr Ile Glu Ser Thr Pro Phe Asn Val Ala Glu
          250                270                290
GGGAAGGAGGTTCTTCTACTCGCCCACAACCTGCCCCAGAATCGTATTGGTTACAGCTGG
Gly Lys Glu Val Leu Leu Leu Ala His Asn Leu Pro Gln Asn Arg Ile Gly Tyr Ser Trp
          310                330                350
TACAAAGGCGAAAGAGTGGATGGCAACAGTCTAATTGTAGGATATGTAATAGGAACTCAA
Tyr Lys Gly Glu Arg Val Asp Gly Asn Ser Leu Ile Val Gly Tyr Val Ile Gly Thr Gln
          370                390                410
CAAGCTACCCCAGGGCCCGCATACAGTGGTTGAGAGACAATATACCCCAATGCATCCCTG
Gln Ala Thr Pro Gly Pro Ala Tyr Ser Gly Arg Glu Thr Ile Tyr Pro Asn Ala Ser Leu
```

A-(d):

```
          430                   450                   470
CTGATCCAGAACGTCACCCAGAATGACACAGGATTCTACACCCTACAAGTCATAAAGTCA
Leu Ile Gln Asn Val Thr Gln Asn Asp Thr Gly Phe Tyr Thr Leu Gln Val Ile Lys Ser 490                   510                   530
GATCTTGTGAATGAAGAAGCAACCGGACAGTTCCATGTATACCCGGAGCTGCCCAAGCCC
Asp Leu Val Asn Glu Glu Ala Thr Gly Gln Phe His Val Tyr Pro Glu Leu Pro Lys Pro 550                   570                   590
TCCATCTCCAGCAACAACTCCAACCCCGTGGAGGACAAGGATGCTGTGGCCTTCACCTGT
Ser Ile Ser Ser Asn Asn Ser Asn Pro Val Glu Asp Lys Asp Ala Val Ala Phe Thr Cys 610                   630                   650
GAACCTGAGGTTCAGAACACAACCTACCTGTGGTGGGTAAATGGTCAGAGCCTCCCGGTC
Glu Pro Glu Val Gln Asn Thr Thr Tyr Leu Trp Trp Val Asn Gly Gln Ser Leu Pro Val 670                   690                   710
AGTCCCAGGCTGCAGCTGTCCAATGGCAACAGGACCCTCACTCTACTCAGCGTCAAAAGG
Ser Pro Arg Leu Gln Leu Ser Asn Gly Asn Arg Thr Leu Thr Leu Leu Ser Val Lys Arg 730                   750                   770
ACCGATGCAGGATCGTATGAATGTGAAATACAGAACCCAGCGAGTGCCAACCGCAGTGAC
Asn Asp Ala Gly Ser Tyr Glu Cys Glu Ile Gln Asn Pro Ala Ser Ala Asn Arg Ser Asp 790                   810                   830
CCAGTCACCCTGAATGTCCTCTATGGCCCAGATGGCCCCACCATTTCCCCCTCAAAGGCC
Pro Val Thr Leu Asn Val Leu Tyr Gly Pro Asp Gly Pro Thr Ile Ser Pro Ser Lys Ala 850                   870                   890
AATTACCGTCCAGGGGAAAATCTGAACCTCTCCTGCCACGCAGCCTCTAACCCACCTGCA
Asn Tyr Arg Pro Gly Glu Asn Leu Asn Leu Ser Cys His Ala Ala Ser Asn Pro Pro Ala 910                   930                   950
CAGTACTCTTGGTTTATCAATGGGACGTTCCAGCAATCCACACAAGAGCTCTTTATCCCC
Gln Tyr Ser Trp Phe Ile Asn Gly Thr Phe Gln Gln Ser Thr Gln Glu Leu Phe Ile Pro 970                   990                  1010
AACATCACTGTGAATAATAGCGGATCCTATATGTGCCAAGCCCATAACTCAGCCACTGGC
Asn Ile Thr Val Asn Asn Ser Gly Ser Tyr Met Cys Gln Ala His Asn Ser Ala Thr Gly 1030                  1050                  1070
CTCAATAGGACCACAGTCACGATGATCACAGTCTCTGGAAGTGCTCCTGTCCTCTCAGCT
Leu Asn Arg Thr Thr Val Thr Met Ile Thr Val Ser Gly Ser Ala Pro Val Leu Ser Ala 1090                  1110                  1130
GTGGCCACCGTCGGCATCACGATTGGAGTGCTGGCCAGGGTGGCTCTGATATAGCAGCCC
Val Ala Thr Val Gly Ile Thr Ile Gly Val Leu Ala Arg Val Ala Leu Ile END
```

```
       1150         1160         1170         1180         1190
TGG TGT ATT TTC GAT ATT TCA GGA AGA CTG GCA GAT TGG ACC AGA CCC TGA ATT CTT 1200        1210         1220         1230         1240         1250
  CTA GCT CCT CCA ATC CCA TTT TAT CCC ATG GAA CCA CTA AAA ACA AGG TCT GCT CTG 1260         1270         1280         1290         1300         1310
CTC CTG AAG CCC TAT ATG CTG GAG ATG GAC AAC TCA ATG AAA ATT TAA AGG AAA AAC 1320         1330         1340         1350         1360         1370
CCT CAG GCC TGA GGT GTG TGC CAC TCA GAG ACT TCA CCT AAC TAG AGA CAG GCA AAC 1380         1390         1400         1410         1420
TGC AAA CCA n n C CTC TTT CGC TTG GCA GGA TGA TGG TGT CAT TAG TAT TTC ACA AGA 1430         1440         1450         1460         1470         1480
AGT AGC TTC AGA GGG TAA CTT AAC AGA GTA TCA GAT CTA TCT TGT CAA TCC CAA CGT 1490         1500         1510         1520         1530         1540
TTT ACA TAA AAT AAG CGA TCC TTT AGT GCA CCC AGT GAC TGA CAT TAG CAG CAT CTT 1550         1560         1570         1580         1590
TAA CAC AGC CGT GTG TTC AAG TGT ACA GTG GTC CTT TTC AGA GTT GGN n n T ACT CCA 1600         1610         1620                   1640         1650
ACT GAA A TG TTA AGG AAG AAG ATA GAT CCA ATAAA AAA AAT TAA AAC CAA TTT AAA 1660         1670         1680         1690         1700         1710
AAA AAA AAA GAA CAC AGG AGA TTC CAG TCT ACT TGA GTT AGC ATA ATA CAG AAG TCC 1720         1730         1740         1750         1760
CCT CTA CTT TAA CTT TTA CAA AAA AGT AAC CTG AAC TAA TCT GAT GTT AAC CAA TGT
```

A-(d):
```
      1770         1780         1790         1800         1810         1820
ATT  TAT  TTG  TCT  GGT  TCT  GTT  TCC  TTG  TTC  CAA  TTT  GAC  AAA  ACC  CAC  TGT  TCT  TGT 1830         1840         1850         1860         1870         1880
ATT  GTA  TTG  CCC  AGG  GGG  AGC  TAT  CAC  TGT  ACT  TGT  AGA  GTG  GTG  CTG  CTT  TAA  GTT 1890         1900         1910         1920         1930         1940
CAT  AAA  TCA  CAA  ATA  AAA  GCC  AAT  TAG  CTC  TAT  AAC  TAA  AAA  AAA  AAA  AAA  AAA  AAA 1950         1960
AAA  AAA  AAA  AAA  AAA  AAA  AAA  AAA
``` which has been designated SEQ ID No.4 and SEQ ID No:12 for the translated polypeptide.

Figure 1B:
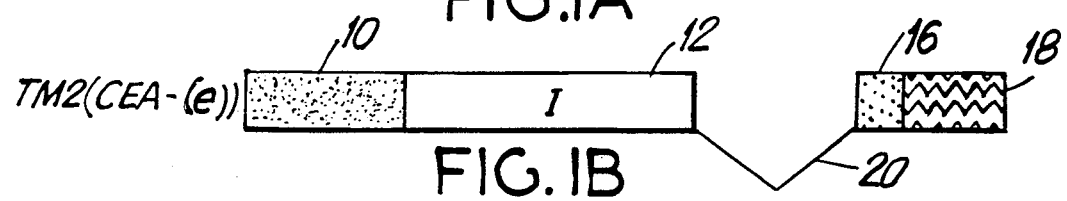
FIG. 1B is a schematic representation of TM2 (CEA-(e))
Figure 1C:
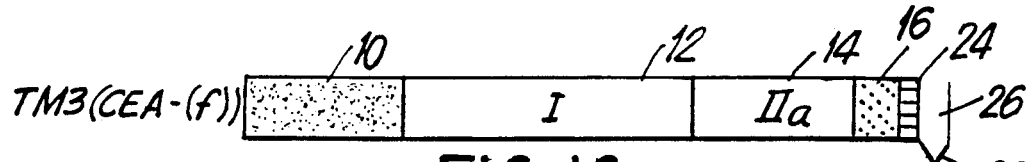
FIG. 1C is a schematic representation of TM3 (CEA-(f))
Figure 1D:
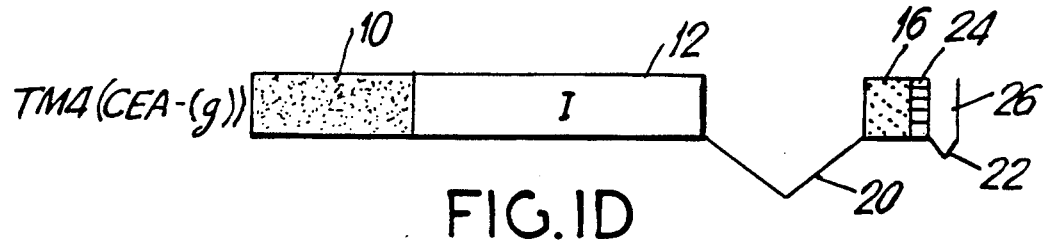
FIG. 1D is a schematic representation of TM4 (CEA-(g)).

A schematic relationship of th transmembrane CEA's, namely TM-1 (CEA-(c)), TM-2 (CEA-(e)), TM-3 (CEA-(f)) and TM-4 (CEA-(g)) is depicted in FIG. 1:

Assuming TM-1 is composed of five sections as depicted in FIG. 1, namely 10, 12, 14, 16 and 18, TM-2 differs from TM-1 in that the 100 amino acid (100 AA) section 14 is deleted and at splice point 20 between sections 12 and 16, surprisingly an extra amino acid, namely Asp occurs.

TM-3 is the same as TM-1 except that section 18 is truncated at splice point 22, i.e., a section of 70 amino acids is deleted and results in a new section made up of subsections 24+26. Surprisingly, however, six new amino acids (section 26) occur. Another example of formation of a novel amino acid sequence resulting from a deletion of nucleic acid sequence is for platelet derived growth factor-A.

TM-4 is the same as TM-2 up until the end of subsection 24.

Subsection 24 is contained in section 18 of TM-1 and TM-2, but is not depicted in FIG. 1 for TM-1 and TM-2.

Some CEA epitopes are unique. These are the epitopes which have been useful for distinguishing the various CEA-like antigens immunologically. Peptide epitopes are defined by the linear amino acid sequence of the antigen and/or features resulting from protein folding. The information required for protein folding is encoded in the primary amino acid sequence. Therefore, antigenic differences ultimately result from differences in the primary structure of the different CEA molecules. The differences residing in the CEA protein in the CEA species can thus be determined by determining the primary amino acid sequences. This can be most readily accomplished by cloning and sequencing each of the genes for CEA. To determine which gene products will be most useful for cancer diagnosis, unique probes can be selected from each gene and expression of each gene can be determined in different tumor types by nucleic acid hybridization techniques. The present invention provides a tool with which to identify potential genes coding for different members of the CEA family and to determine the theoretical primary amino acid sequences for them. Using the method of automated peptide synthesis, peptides can then be synthesized corresponding to unique sequences in these antigens. With these peptides, antibodies to these sequences can be produced which, in the intact CEA molecule, might not be recognized by the animal being immunized. Having accomplished this, advantage can then be taken of the differences in these antigens to generate specific immunoassays for the measurement of each antigen.

A wide variety of host/cloning vehicle combinations may be employed in cloning the double-stranded nucleic acid prepared in accordance with this invention. For example, useful cloning vehicles may consist of segments of chromosomal, non-chromosomal and synthetic DNA sequences, such as various known derivatives of SV40 and known bacterial plasmids, e.g., plasmids from E. coli including col E1, pCR1, pBR322, pMB89 and their derivatives, wider host range plasmids, e.g., RP4, and phage DNAs, e.g., the numerous derivatives of phage, e.g., NM989, and other DNA phages, e.g., M13 and Filamenteous single-stranded DNA phages and vectors derived from combinations of plasmids and phage DNAs such as plasmids which have been modified to employ phage DNA or other expression control sequences or yeast plasmids such as the 2 μplasmid or derivatives thereof. Useful hosts may include bacterial hosts such as strains of E. coli, such as E. coli HB 101, E. coli X1776, E. coli X2282, E. coli MRC1 and strains of Pseudomonas, Bacillus subtilis, Bacillus stearothermophilus and other E. coli, bacilli, yeasts and other fungi, animal or plant hosts such as animal (including human) or plant cells in culture or other hosts. Of course, not all host/vector combinations may be equally efficient. The particular selection of host/cloning vehicle combination may be made by those of skill in the art after due consideration of the principles set forth without departing from the scope of this invention.

Furthermore, within each specific cloning vehicle, various sites may be selected for insertion of the nucleic acid according to the present invention. These sites are usually designated by the restriction endonuclease which cuts them. For example, in pBR322 the Pstl site is located in the gene for beta-lactamase, between the nucleotide triplets that code for amino acids 181 and 182 of that protein. One of the two HindII endonuclease recognition sites is between the triplets coding for amino acids 101 and 102 and one of the several Taq sites at the triplet coding for amino acid 45 of beta-lactamase in pBR322. In similar fashion, the EcoRI site and the PVUII site in this plasmid lie outside of any coding region, the EcoRI site being located between the genes coding for resistance to tetracycline and ampicillin, respectively. These sites are well recognized by those of skill in the art. It is, of course, to be understood that a cloning vehicle useful in this invention need not have a restriction endonuclease site for insertion of the chosen DNA fragment. Instead, the vehicle could be cut and joined to the fragment by alternative means.

The vector or cloning vehicle and in particular the site chosen therein for attachment of a selected nucleic acid fragment to form a recombinant nucleic acid molecule is determined by a variety of factors, e.g., the number of sites susceptible to a particular restriction enzyme, the size of the protein to be expressed, the susceptibility of the desired protein to proteolytic degradation by host cell enzymes, the contamination of the protein to be expressed by host cell proteins difficult to remove during purification, the expression characteristics, such as the location of start and stop codons relative to the vector sequences, and other factors recognized by those of skill in the art. The choice of a vector and an insertion site for a particular gene is determined by a balance of these factors, not all sections being equally effective for a given case.

Methods of inserting nucleic acid sequences into cloning vehicles to form recombinant nucleic acid molecules include, for example; da-dT tailing, direct ligation, synthetic linkers, exonuclease and polymerase-linked repair reactions followed by ligation, or extension of the nucleic acid strand with an appropriate polymerase and an appropriate single-stranded template followed by ligation.

It should also be understood that the nucleotide sequences or nucleic acid fragments inserted at the selected site of the cloning vehicle may include nucleotides which are not part of the actual structural gene for the desired polypeptide or mature protein or may include only a fragment of the complete structural gene for the desired protein or mature protein.

The cloning vehicle or vector containing the foreign gene is employed to transform an appropriate host so as to permit that host to replicate the foreign gene and to express the protein coded by the foreign gene or portion thereof. The selection of an appropriate host is also controlled by a number of factors recognized by the art. These include, for example, the compatibility with the chosen vector, the toxicity of proteins encoded by the hybrid plasmid, the ease of recovery of the desired protein, the expression characteristics, biosafety and costs. A balance of these factors must be struck with the understanding that not all hosts may be equally effective for expression of a particular recombinant DNA molecule.

The level of production of a protein is governed by two major factors: the number of copies of its gene within the cell and the efficiency with which these gene copies are transcribed and translated. Efficiency of transcription and translation (which together comprise expression) is in turn dependent upon nucleotide sequences, normally situated ahead of the desired coding sequence. These nucleotide sequences or expression control sequences define inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to other known expression control sequences so as to favor higher levels of expression. This having been achieved, the newly engineered nucleic acid, e.g., DNA, fragment may be inserted into a multicopy plasmid or a bacteriophage derivative in order to increase the number of gene copies within the cell and thereby further improve the yield of expressed protein.

Several expression control sequences may be employed as described above. These include the operator, promoter and ribosome binding and interaction sequences (including sequences such as the Shine-Dalgarno sequences) of the lactose operon of *E. coli* ("the lac system"), the corresponding sequences of the tryptophan synthetase system of *E. coli* ("the trp system"), the major operator and promoter regions of phase $\lambda(O_L P_L$ and $O_R P'_R)$, the control region of Filamenteous singlestranded DNA phages, or other sequences which control the expression of genes of prokaryotic or eukaryotic cells and their viruses. Therefore, to improve the production of a particular polypeptide in an appropriate host, the gene coding for that polypeptide may be selected and remove from a recombinant nucleic acid molecule containing it and reinserted into a recombinant nucleic acid molecule closer or in a more appropriate relationship to its former expression control sequence or under the control of one of the above described expression control sequences. Such methods are known in the art.

As used herein "relationship" may encompass many factors, e.g., the distance separating the expression enhancing and promoting regions of the recombinant nucleic acid molecule and the inserted nucleic acid sequence, the transcription and translation characteristics of the inserted nucleic acid sequence or other sequences in the vector itself, the particular nucleotide sequence of the inserted nucleic acid sequence and other sequences of the vector and the particular characteristics of the expression enhancing and promoting regions of the vector.

Further increases in the cellular yield of the desired products depend upon an increase in the number of genes that can be utilized in the cell. This is achieved, for illustration purposes, by insertion of recombinant nucleic acid molecules engineered into the temperature bacteriophage λ(NM989), most simply by digestion of the plasmid with a restrictive enzyme, to give a linear molecule which is then mixed with a restricted phage λ cloning vehicle (e.g., of the type described by N. E. Murray et al, "Lambdoid Phages That Simplify the Recovery of In Vitro Recombinants", *Molec. Gen. Genet.*, 150, pp. 53-61 (1977) and N. E. Murray et al. "Molecular Cloning of the DNA Ligase Gene From Bacteriophage T4", *J. Mol. Biol.*, 132, pp. 493-505 (1979)) and the recombinant DNA molecule recircularized by incubation with DNA ligase. The desired recombinant phage is then selected as before and used to lysogenize a host strain of *E. coli*.

Particularly useful λ cloning vehicles contain a temperature-sensitive mutation in the repression gene cl and suppressible mutations in gene S, the product of which is necessary for lysis of the host cell, and gene E, the product of which is major capsid protein of the virus. With this system, the lysogenic cells are grown at 32° C. and then heated to 45° C. to induce excision of the prophage. Prolonged growth at 37° C. leads to high levels of production of the protein, which is retained within the cells, since these are not lysed by phage gene products in the normal way, and since the phage gene insert is not encapsulated it remains available for further transcription. Artificial lysis of the cells then releases the desired product in high yield.

In addition, it should be understood that the yield of polypeptides prepared in accordance with this invention may also be improved by substituting different codons for some or all of the codons of the present DNA sequences, these substituted codons coding for amino acids identical to those coded for the codons replaced.

Finally, the activity of the polypeptides produced by the recombinant nucleic acid molecules of this invention may be improved by fragmenting, modifying or derivatizing the nucleic acid sequences or polypeptides of this invention by well-known means, without departing from the scope of this invention.

The polypeptides of the present invention include the following:

(1) the polypeptides expressed by the above described cells, (2) polypeptides prepared by synthetic means, (3) fragments of polypeptides (1) or (2) above, such fragments produced by synthesis of amino acids or by digestion or cleavage.

Regarding the synthetic peptides according to the invention, chemical synthesis of peptides is described in the following publications: S. B. H. Kent, *Biomedical Polymers*, eds. Goldberg, E. P. and Nakajima, A. (Academic Press, New York), 213-242, (1980); A. R. Mitchell, S. B. H. Kent, M. Engelhard and R. B. Merrifield, *J. Org. Chem.*, 43, 2845-2852, (1978); J. P. Tam, T. -W. Wong, M. Riemen, F. -S. Tjoeng and R. B. Merrifield, *Tet. Letters*, 4033-4036, (1979); S. Mojsov, A. R. Mitchell and R. B. Merrifield, J. Org. Chem., 45, 555-560, (1980); J. P. Tam, R. D. DiMarchi and R. B. Merrifield, *Tet. Letters*, 2851-2854, (1981); and S. B. H. Kent, M. Riemen, M. Le Doux and R. B. Merrifield, *Proceedings of the IV International Symposium on Methods of Protein Sequence Analysis*, (Brookhaven Press, Brookhave, N.Y.), in press, 1981.

In the Merrifield phase procedure, the appropriate sequence of L-amino acids ia guilt up from the carboxyl terminal amino acid to the amino terminal amino acid. Starting with the appropriate carboxyl terminal amino acid attached to a polystyrene (or other appropriate) resin via chemical linkage to a chloromethyl group, benzhydrylamine group, or other reactive group of the resin, amino acids are added by one using the following procedure. The peptide-resin is:

(a) washed with methylene chloride;
(b) neutralized by making for 10 minutes at room temperature with 5% (v/v) diisopropylethylamine (or other hindered base) in methylene chloride;
(c) washed with methylene chloride;
(d) an amount of amino acid equal to six times the molar amount of the growing peptide chain is activated by combining it with one-half as many moles of a carbodiimide (e.g., dicyclohexylcarbodiimide, or diisopropylcarbodiimide) for ten minutes at 0° C., to form the symmetric anhydride of the amino acid. The amino acid used should be provided originally as the N-alpha-tert.-butyloxycarbonyl derivative, with side chains protected with benzyl esters (e.g., aspartic or glutamic acids), benzyl ethers (e.g., serine, threonine, cysteine or tyrosine), benzyloxycarbonyl groups (e.g., lysine) or other protecting groups commonly used in peptide synthesis;
(e) the activated amino acid is reacted with the peptide-resin for two hours at room temperature, resulting in addition of the new amino acid to the end of the growing peptide chain;
(f) the peptide-resin is washed with methylene chloride;
(g) the N-alpha-(tert.-butyloxycarbonyl) group is removed from the most recently added amino acid by reacting with 30 to 65%, preferably 50% (v/v) trifluoroacetic acid in methylene chloride for 10 to 30 minutes at room temperature;
(h) the peptide-resin is washed with methylene chloride;
(i) steps (a) through (h) are separated until the required peptide sequence has been constructed.

The peptide is then removed from the resin and simultaneously the side-chain protecting groups are removed, by reaction with anhydrous hydrofluoric acid containing 10% v/v of anisole or other suitable (aromatic) scavenger. Subsequently, the peptide can be purified by gel filtration, ion exchange, high pressure liquid chromatography, or other suitable means.

In some cases, chemical synthesis can be carried out without the solid phase resin, in which case the synthetic reactions are performed entirely in solution. The reactions are similar and well known in the art, and the final product is essentially identical.

Digestion of the polypeptide can be accomplished by using proteolytic enzymes, especially those enzymes whose substrate specificity results in cleavage of the polypeptide at sites immediately adjacent to the desired sequence of amino acids.

Cleavage of the polypeptide can be accomplished by chemical means. Particular bonds between amino acids can be cleaved by reaction with specific reagents. Examples include the following: bonds involving methionine are cleaved by cyanogen bromide; asparaginyl-glycine bonds are cleaved by hydroxylamine.

The present invention has the following advantages:

(1) The nucleic acids coding for TM-1, Tm-2 and TM-3 can be used as probes to isolate other members of the CEA gene family.

(2) The nucleic acids coding for TM-1, TM-2 and TM-3 can be used to derive oligonucleotide probes to determine the expresssion of TM-1, TM-2, TM-3 and other CEA genes in various tumor types.

(3) TM-1, TM-2, TM-3 and TM-4 nucleotide sequences can be used to predict the primary amino acid sequence of the protein for production of synthetic peptides.

(4) Synthetic peptides derived from the above sequences can be used to produce a sequence-specific antibodies.

(5) Immunoassays for each member of the CEA antigen family can be produced with these sequence-specific antibodies and synthetic peptides.

(6) The aforementioned immunoassays can be used as diagnostics for different types of cancer if it is determined that different members of the CEA family are clinically useful markers for different types of cancer.

Peptides according to the present invention can be labelled by conventional means using radioactive moieties (e.g., $^{125}I$), enzymes, dyes and fluorescent compounds, just to name a few.

Several possible configurations for immunoassays according to the present invention can be used. The readout systems capable of being employed in these assays are numerous and non-limiting examples of such systems include fluorescent and colorimetric enzyme systems, radioisotopic labelling and detection and chemiluminescent systems. Two examples of immunoassay methods are as follows:

(1) An enzyme linked immunoassay (ELISA) using an antibody preparation according to the present invention (including Fab or F(ab)' fragments derived therefrom) to a solid phase (such as a microtiter plate or latex beads) is attached a purified antibody of a specificity other than that which is conjugated to the enzyme. This solid phase antibody is contacted with the sample containing CEA antigen family members. After washing, the solid phase antibody-antigen complex is contacted with the conjugated anti-peptide antibody (or conjugated fragment). After washing away unbound conjugate, color or fluorescence is developed by adding a chromogenic or fluorogenic substrate for the enzyme. The amount of color or fluorescence developed is proportional to the amount of antigen in the sample.

(2) A competitive fluorometric immunoassay using fluorescently labelled peptide or synthetic peptides of the sequences for TM-2, TM-2, TM-3 and TM-4. In this example, the purified peptide expressed by cells or synthetic peptides thereof are fluorescently labelled. To a solid phase is attached a purified antibody. This solid phase is then contacted with sample containing CEA antigen family members to which has been added fluorescent peptide probe. After binding, excess probe is washed away the amount of bound probe is quantitated. The amount of bound fluorescent probe will be inversely proportional to the amount of antigen in the sample.

In the nucleic acid hybridization method according to the present invention, the nucleic acid probe is conjugated with a label, for example, an enzyme, a florophore, a radiostope, a chemiluminescent compound, etc. In the most general case, the probe would be contacted with the sample and the presence of any hybridizable nucleic acid sequence would be detected by developing in the presence of a chromogenic enzyme substrate, detection of the fluorophore by epifluorescence, by autoradiography of the radioisotopically labelled probe or by chemiluminescence. The detection of hybridizable RNA sequences can be accomplished by (1) a dot blot methodology or (2) an in situ hybridization methodology. Methods of these last two techniques are described by D. Gillespie and J. Bresser, "mRNA Immobilization in NaI: Quick Blots", *Biotechniques*, 184–192, November/December 1983 and J. Lawrence and R. Singer, "Intracellular Localization of Messenger RNAs for Cytosketal Proteins", *Cell*, 45, 407–415, May 9, 1986, respectively. The readout systems can be the same as described above, e.g., enzyme labelling, radiolabelling, etc.

As stated above, the invention also relates to the use in medicine of the aforementioned complex of the invention.

The invention further provides a pharmaceutical composition containing as an active ingredient a complex of the invention in the form of a sterile and/or physiologically isotonic aqueous solution.

For parenteral administration, solutions and emulsions containing as an active ingredient the complex of the invention should be sterile and, if appropriate, blood-isotonic.

It is envisaged that the active complex will be administered perorally, parenterally (for example, intramuscularly, intraperitoneally, or intravenously), rectally or locally.

EXAMPLE 1

Preparation of cDNA in pCE22 which codes for TM2-CEA [CEA-(e))

Example 1a

RNA Preparation

Messenger RNA was prepared by the proteinase K extraction method of J. Favolaro, R. Treisman and R. Kamen, *Methods in Enzymology*, 65, 718, Academic Press, Inc. (1980), followed by olido dT cellulose chromatography to yield poly A+ RNA (3'-polyadenylated eukaryotic RNA containing most mRNA sequences that can be translated into polypeptides). To obtain approximately 100 μg of poly A+ RNA, approximately $\times 10^8$ cells of transfectant 23.411 (ATCC No. CRL 9731, deposited with the ATCC on Jun. 1, 1988), that expresses TM-1, TM-2, TM-3 and TM-4, Kamarck et al, *Proc. Natl. Acad. Sci., USA*, 84, 5350–5354, August 1987, were harvested from roller bottles after late logarithmic growth. Cells were lysed by homogenization in an ice-cold solution of 140 mM NaCl, 1.5 mM MgCl$_2$, 10 mM Tris-HCl, pH 8.0, 0.5% NP40, 4 mM dithiothreitol and 20 units of placental ribonuclease inhibitor/ml. sodium deoxycholate was then added to 0.2 %. Cytoplasm and nuclei were separated by centrifugation of the homogenate at 12,000×g for 20 minutes. The cytoplasmic fraction was mixed with an equal volume of 0.2 M Tris-HCl, pH 7.8, 25 mM EDTA, 0.3 M NaCl, 2% sodium dodecyl sulfate and 400 μg/ml of proteinase K, incubated for 1 hour at 37° C., then extracted once with an equal volume of phenol/chloroform (1:1/v:v) solution. Nucleic acids were obtained by ethanol precipitation of the separated aqueous phase. Total RNA was enriched by passage in 0.5 M NaCl, 10 mM Tris-HCl, pH 7.8, 0.1% sarcosyl through an oligo dT(12-18) cellulose column. After washing, bound RNA was eluted in the same solution without sodium chloride.

Example 1b

Reverse Transcription of mRNA

Ten micrograms of poly A+ RNA were primed for reverse transcription with oligo dT(12-18) and pdN$_6$ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids was replaced with the second complementary strand by treatment with RTNase H, *E. coli* DNA polymerase I and *E. coli* DNA ligase at 12° C. and 22° C. for 1.5 hours each. Molecular ends were polished by treatment with T4 DNA polymerase. cDNA was phenol/chloroform extracted and purified over a "SEPHADEX G-50" spun column prepared in 10 mM Tris-HCl, pH 7.8, 1 mM EDTA (TE).

Example 1c

Cloning of pcE22 (plasmid cDNA E22)

Synthetic DNA linkers

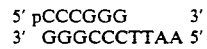

were attached to the ends of cDNA by blunt end ligation with excess T4 DNA ligase. Excess linkers were removed by chromatography through "SEPHADEX G-50" (medium) in TE, and by fractionation of 0.8% low melting agarose gel. Based on Northern blot analysis of poly A+ RNA of the 23.411 cell line, the size of the CEA-related mRNA was estimated at 3.6 kb. Therefore, cDNA fragments between 2 and 4 kb were recovered from gel slices and fragments were ethanol precipitated. After resuspension of cDNA in TE, EcoRI-cleaved lambda gt10 arms were added to cDNA at an estimated molar ratio of 1:1. Ligation proceeded at 7° C. for 2 days in the presence of T4 DNA ligase. Aliquots of the ligation reaction were added to commercially-obtained packaging mix (Stratagene, San Diego, Calif., U.S.A.). Five million phage particles were obtained ofter in vitro packaging and infection of E. coli host NM514.

Example 1d

Screening of Recombinant Library

Five hundred thousand packaged lambda particles were plated on lawns of E. coli NM514 and replicate patterns were lifted onto nitrocellulose sheets as described by W. D. Benton and R. W. Davis, Science 196, 180–182, (1977). Positive phase were selected by hybridization with $^{32}$P-labeled LV7 cDNA insert probe that contained a domain repeated amoung various CEA family members. By multiple rounds of screening. Phage from individual plaques were amplified and titered, and these were used to prepare small quantities of recombinant phage DNA.

Example 1e

DNA Manipulation

Phage DNA was prepared according to T. Maniatis, E. Fritsch and J. Sambrook, *Molecular Cloning, A Laboratory Manual*, Cold Spring Habor, (1982). DNA segments were isolated from low melting agarose gels and inserted for subcloning into Bluescript plasmid vectors (Stratagene, San Diego, Calif., U.S.A.). DNA sequencing was performed by the dideoxy termination method of F. Sanger, S. Nicklen and A. Coulson, *Proc. Natl. Acad. Sci., U.S.A.*, 74, 5463–5467, (1977). The nucleic acid and translated sequence for cDNA in pcE22 is given hereinabove (TM-2(CEA-(e)).

EXAMPLE 2

Preparation of cDNA in pcHT-6 which Partically Codes TM3-CEA [CEA-(f)]

Example 2a

RNA Preparation

Messenger RNA was prepared by the proteinase K extraction method of J. Favolaro, R. Treismand and R. Kamen, *Methods in Enzymology*, 65 718, Academic Press, Inc. (1980), followed by oligo dT cellulose chromatography to yield poly A+ RNA (3'-polyadenylated eukaryotic RNA containing most mRNA sequences that can be translated into polypeptides). To obtain approximately 100 ug of poly A+ RNA, approximately $3 \times 10^8$ cells of HT-29 tumor cells (ATCC HTB38) were harvested form roller bottles after late logarithmic growth. Cells were lysed by homogenization in an ice-cold solution of 140 mM NaCl, 1.5 mM MgCl$_2$, 10 mM Tri-HCl, pH 8.0, 0.5% NP40, 4 mM dithiothreitol and 20 units of placental ribonuclease inhibitor/ml. Sodium deoxycholate was then added to 0.2 %. Cytoplasm and nuclei were separated by centrifugation of the homogenate at 12,000×g for 20 minutes. The cytoplasmic fraction was mixed with an equal volume of 0.2 M Tris-Hcl, pH 7.8, 25 mM EDTA, 0.3 M NaCl, 2% sodium dodecyl sulfate and 400 μg/ml of proteinase K, incubated for 1 hour at 37° C., then extracted once with an equal volume of phenol/chloroform (1:1/v:v) solution. Nucleic acids were obtained by ethanol precipitation of the separated aqueous phase. Total RNA was enriched by passage in 0.5 M NaCl, 10 mM Tris-HCl, pH 7.8, 0.1% sarcosyl through an oligo dT(12-18) cellulose column. After washing, bound RNA was eluted in the same solution without sodium chloride.

Example 2b

Reverse Transcription of mRNA

Ten microgram of HT-29 poly A+ RNA were primed for reverse transcription with olido dT(12-18) and pdN$_6$ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids was replaced with the second complementary strand by treatment with RNase H, E. coli DNA polymerase I and E. coli DNA ligase at 12° C. and 22° C. for 1.5 hours each. Molecular ends were polished by treatment with T4 DNA polymerase. cDNA was phenol/chloroform extracted and purified over a "SEPHADEX G-50" spun column prepared in 10 mM Tris-HCl, pH 7.8, 1 mM EDTA (TE).

Example 2c

Cloning of pcHT-6 (plasmid cDNA HT-6)

Synthetic DNA linkers

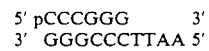

were attached to the ends of cDNA by blunt end ligation with excess T4 DNA ligase. Excess linkers were removed by chromatography through "SEPHADEX G-50" (medium) in TE, and by fractionation on 0.8% low melting agarose gel. Based on Northern blot analysis of poly A+ RNA of the HT-29 cell line, the size of the CEA-related mRNA was estimated at 2.2 kb. Therefore, cDNA fragments between 2 and 3 kb were recovered from gel slices and fragments were ethanol precipitated. After resuspension of cDNA in TE, EcoRI-cleaved lambda gt10 arms were added to cDNA at an estimated molar ratio of 1:1. Ligation proceeded at 7° C. for 2 days in the presence of T4 DNA ligase. Aliquots of the ligation reaction were added to commercially-obtained packaging mix (Stratagene, San Diego, Calif., U.S.A.). Five million phage particles were obtained often in vitro packaging and infection of E. coli host NM514.

Example 2d

Screening of Recombinant Library

Five hundred thousand packaged lambda particles were plated on lawns of E. coli NM514 and replicate patterns were lifted onto nitrocellulose sheets as described by W. D. Benton and R. W. David, Science, 196, 180–182, (1977). Positive phage were selected by hybridization with $^{32}$P-labeled LV7 cDNA insert probe that contained a domain repeated amoung various CEA family members. By multiple rounds of screening. Phage from individual plaques were amplified and titered, and these were used to prepare small quantities of recombinant phage DNA.

Example 2e

DNA Manipulation

Phage DNA was prepared according to T. Maniatis, E. Fritsch and J. Sambrook, *Molecular Cloning, A Laboratory Manual*, Cold Spring Habor, (1982). DNA segments were isolated from low melting agarose gels and inserted for subcloning into Bluescript plasmid vectors (Stratagene, San Diego, Calif., U.S.A.). DNA sequencing was performed by the dideoxy termination method of F. Sanger, S. Nicklen and A. Coulson, *Proc. Natl. Acad. Sci., U.S.A.*, 74, 5463-5467, (1977). The nucleic acid and translated sequence for cDNA in HT-6 not complete at the 5' end of its coding region, but the nucleotide sequence and restriction map of the HT-6 inset indicates that it is related to nucleic acid sequences of cDNA clones coding for CEA-(c) and CEA-(e). The nucleotide sequence of HT-6 insert differs from these clones at only nucleotide position 1463 to 1515 and 1676 to 2429 of the CEA-(c) cDNA. It is inferred from this result that the pcHT-6 insert is a partial coding sequence for CEA-(f) and the presumed nucleic acid and translated sequence of CEA-(f) is given hereinabove (TM-3 (CEA-(f)).

EXAMPLE 3

Preparation of cDNA which codes for TM4-CEA [CEA-(g)]

Example 3a

RNA Preparation

Messenger RNA is prepared by the proteinase K extraction method of J. Favolaro, R. Treisman and R. Kamen, *Methos in Enzymology*, 65, 718, Academic Press, Inc. (1980), followed by oligo dT cellulose chromatography to yield poly A+ RNA (3'-polyadenylated eukaryotic RNA containing most mRNA sequences that can be translated into polypeptides). To obtain approximately 100 ug of poly A+ RNA, approximately $3 \times 10^8$ cells of transfectant 23.411 or tumor cell line HT-29 (ATCC HTB 38) are harvested from roller bottles after late logarithmic growth. Cells are lysed by homogenization in an ice-cold solution of 140 mM NaCl, 1.5 mM $MgCl_2$, 10 mM Tris-Hcl, pH 8.0, 0.5% NP40, 4 mM dithiothreitol and 20 units of placental ribonuclease inhibitor/ml. Sodium deoxycholate was then added to 0.2%. Cytoplasm and nuclei are separated by centrifugation of the homogenate at $12,000 \times g$ for 20 minutes. The cytoplasmic fraction is mixed with an equal volume of 0.2 M Tris-Hcl, pH 7.8, 25 mM EDTA, 0.3 M NaCl, 2% sodium dodecyl sulfate and 400 µg/ml of proteinase K, incubated for 1 hour at 37° C., the extracted once with an equal volume of phenol/-chloroform (1:1/v:v) solution. Nucleic acids are obtained by ethanol precipitation of the separated aqueous phase. Total RNA is enriched by passage in 0.5 M NaCl, 10 mM Tris-HCl, pH 7.8, 0.1% sarcosyl through an oligo dT(12-18) cellulose column. After washing, bound RNA is eluted in the same solution without sodium chloride.

Example 3b

Reverse Transcription of mRNA

Ten micrograms of 23.411 or HT 29 poly A+ RNA are primed for reverse transcription with oligo dT(12-18) and pdN$_6$ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids is replaced with the second complementary strand by treatment with RNase H, *E. coli* DNA polymerase I and *E. coli* DNA ligase at 12° C. and 22° C. for 1.5 hours each. Molecular ends are polished by treatment with T4 DNA polymerase. cDNA is phenol/chloroform extracted and purified over a "SE-PHADEX G-50" spun column prepared in 10 mM Tris-HCl, pH 7.8, 1 mM EDTA (TE).

Example 3c

Cloning of cDNA for CEA-(g)

Synthetic DNA linkers

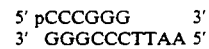

are attached to the ends of cDNA by blunt and ligation with excess T4 DNA ligase. Excess linkers are removed by chromatography through "SEPHADEX G-50" (medium) in TE, and by fractionation on 0.8% low melting agarose gel. Based on Northern blot analysis of poly A+ RNA of the 23.411 and HT-29 cell lines, the size of the CEA-related mRNA is estimated at 1.7 kb. Therefore, cDNA fragments between 1 and 2 kb are recovered from gel slices and fragments are ethanol precipitated. After resuspension of cDNA in TE, EcoRI-cleaved lambda gt10 arms are added to cDNA at an estimated molar ratio of 1:1. Ligation proceeds at 7° C. for 2 days in the presence of T4 DNA ligase. Aliquots of the ligation reaction are added to commercially-obtained packaging mix (Stratagene, San Diego, Calif., U.S.A.). Pharge particles are obtained after in vitro packaging and infection of *E. coli* host NM514.

Example 3d

Screening of Recombinant Library

Five hundred thousand to one million packaged lambda particles are plated on lawns of *E. coli* NM514 and replicate patterns are lifted onto nitrocellulose sheets as described by W. D. Benton and R. W. Davis, *Science*, 196, 180-182, (1977). Positive phage are selected by hybridization with $^{32}$P-labeled LV7 cDNA insert probe that contained a domain repeated amoung various CEA family members. By this selection method, positive phage are obtained after multiple rounds of screening. Phage from individual plaques are amplified and titered, and these are used to prepare small quantities of recombinant phage DNA.

Example 3e

DNA Manipulation

Phage DNA is prepared according to T. Maniatis, E. Fritsch and J. Sambrook, *Molecular Cloning, A Laboratory Manual*, Cold Spring Harbor, (1982). DNA segments are isolated from low melting agarose gels and inserted for subcloning into Bluescript plasmid vectors (Stratagene, San Diego, Calif., U.S.A.). DNA sequencing is performed by the dideoxy termination method of F. Sanger, S. Nicklen and A. Coulson, *Proc. Natl. Acad. Sci., U.S.A.*, 74, 5463-5467, (1977). The nucleotide and translated sequence for a cDNA coding for CEA-(g) is given hereinabove (TM-4 (CEA-(g)).

EXAMPLE 4

Screening of KG-1 cDNA Library with $^{32}$P-labelled CEA Probe, LV7 (CEA-(A))

A segment of cDNA coding for a portion of carcinoembryonic antigen [LV7 or CEA-(a)] was radiolabelled by random priming and used to detect homologous sequences on filter replicas of a commercial cDNA library prepared from KG-1 cells in bacteriophage vector λgt11 (Clontech Laboratories, Inc., Palo Alto, Calif., U.S.A.). Hybridizations were performed at 68° C. in 2×SSSPE (1×SSPE—0.15 M NaCl, 0.01 M sodium phosphate and 1 mM EDTA, pH 7), 5×Denhardt's solution and 100 μg of denatured salmon sperm DNA per ml, and post-hybridization washes were in 0.2×SSC, 0.25% sodium dodecyl sulfate.

Positive phage were picked, rescreened to homogeneity, and amplified for production of DNA. cDNA inserts were excised from phage DNA with EcoRI enconuclease and subcloned into the EcoRI site of the plasmid vector pBluescript KS. DNA sequencing on double-stranded DNA was by the method of Sanger et al, supra. The sequences of two different inserts from the KG-1 cDNA library are shown below:

pcKGCEA1:

```
   1 acagcacagctgacagccgtactcaggaagcttctggatcctaggcttatctccacagag                                60

61 gagaacacacaagcagcagagaccatg gggccc ctc tca gccct ccc tgc aca cacctc                        120
                                MetGlyProLeuSerAlaProProCysThrHisLeu 121 atcact tgg aag gggtc ctg ctc aca gcatca ctt tta aac ttc tgg aat ccgccc aca                 180
      IleThrTrpLysGlyValLeuLeuThrAlaSerLeuLeuAsnPheTrpAsnProProThr 181 act gcccaa gtc acg attgaa gcccag cca ccc aaa gtt tct gag ggg aag gat gtt ctt              240
      ThrAlaGlnValThrIleGluAlaGlnProProLysValSerGluGlyLysAspValLeu 241 cta ctt gtc cacaat ttg ccc cag aat ctt gct ggc tac atttgg tac aaa gggcaa atg              300
      LeuLeuValHisAsnLeuProGlnAsnLeuAlaGlyTyrIleTrpTyrLysGlyGlnMet 301 aca tac gtc tac cat tac attaca tca tat gta gta gac ggt caa aga attatatat ggg              360
      ThrTyrValTyrHisTyrIleThrSerTyrValValAspGlyGlnArgIleIleTyrGly 361 cct gcatac agt gga aga gaa aga gta tat tcc aat gcatcc ctc ctg atccag aat gtc              420
      ProAlaTyrSerGlyArgGluArgValTyrSerAsnAlaSerLeuLeuIleGlnAsnVal 421 acg cag gag gat gcagga tcc tac acc tta cacatcataaag cga cgc gat gggact gga                480
      ThrGlnGluAspAlaGlySerTyrThrLeuHisIleIleLysArgArgAspGlyThrGly 481 gga gta act gga cat ttc acc ttc acc tta cacctg gagact cccaag ccctcc atctcc                540
      GlyValThrGlyHisPheThrPheThrLeuHisLeuGluThrProLysProSerIleSer 541 agcagcaac tta aat ccc agg gag gccatg gag gct gtg atcta acc tgt gat cct gcg                600
      SerSerAsnLeuAsnProArgGluAlaMetGluAlaValIleLeuThrCysAspProAla 601 act cca gccgcaagctac cag tgg tgg atg aat ggt cag agcctc cct atg act cacagg                660
      ThrProAlaAlaSerTyrGlnTrpTrpMetAsnGlyGlnSerLeuProMetThrHisArg 661 ttg cagctg tcc aaa acc aac agg acc ctc ttt atattt ggt gtc aca aag tat attgca              720
      LeuGlnLeuSerLysThrAsnArgThrLeuPheIlePheGlyValThrLysTyrIleAla 721 gga ccc tat gaa tgt gaa atacgg aac cca gtg agt gccagccgc agt gac cca gtc acc              780
      GlyProTyrGluCysGluIleArgAsnProValSerAlaSerArgSerAspProValThr 781 ctg aat ctc ctc cca aag ctg tcc aag ccc tac atcaca atcaac aac tta aac cccaga              840
      LeuAsnLeuLeuProLysLeuSerLysProTyrIleThrIleAsnAsnLeuAsnProArg 841 gag aat aag gat gtc tta acc ttc acc tgt gaa cct aag agt gag aac tac acc tac att          900
      GluAsnLysAspValLeuThrPheThrCysGluProLysSerGluAsnTyrThrTyrIle 901 tgg tgg cta aat ggt cag agcctc cct gtc agt cccagg gta aag cga cccattgaa aac              960
      TrpTrpLeuAsnGlyGlnSerLeuProValSerProArgValLysArgProIleGluAsn 961 agg atcctc attcta ccc aat gtc acg aga aat gaa aca ggacct tat caa tgt gaa ata             1020
      ArgIleLeuIleLeuProAsnValThrArgAsnGluThrGlyProTyrGlnCysGluIle 1021 cgg gac cga tat ggt ggc atccgc agt gac cca gtc acc ctg aat gtc ctc tat ggt cca           1080
      ArgAspArgTyrGlyGlyIleArgSerAspProValThrLeuAsnValLeuTyrGlyPro 1081 gac ctc ccc agcatttac cct tca ttc acc tat tac cgt tca gga gaa aac ctc tac ttt            1140
      AspLeuProSerIleTyrProSerPheThrTyrTyrArgSerGlyGluAsnLeuTyrPhe 1141 tcc tgc ttc ggt gag tct aac cca cgg gcacaa tat tct tgg aca attaat ggg aag ttt            1200
      SerCysPheGlyGluSerAsnProArgAlaGlnTyrSerTrpThrIleAsnGlyLysPhe 1201 cag cta tca gga caa aag ctc tct atccccaa ataact aca aag cat agt gggctc tat               1260
      GlnLeuSerGlyGlnLysLeuSerIleProGlnIleThrThrLysHisSerGlyLeuTyr 1261 gct tgc tct gtt cgt aac tca gccact ggcaag gaa agctcc aaa tcc atcaca gtc aaa              1320
      AlaCysSerValArgAsnSerAlaThrGlyLysGluSerSerLysSerIleThrValLys 1321 gtc tct gac tgg atatta ccctga attctactagttcctccaattccattttctcccatg                       1380
      ValSerAspTrpIleLeuProEnd 1381 gaatcacgaagagcaagacccactctgttccagaagcccataatctggaggtggacaac                              1440
1441 tcgatgtaaatttcatgggaaaacccttgtacctgacatgtgagccactcagaactcacc                             1500
```

-continued

```
1501 aaaatgttcgacaccataacaacagctactcaaactgtaaaccaggataagaagttgatg    1560
1561 acttcacactgtggacagttttcaaagatgtcataacaagactccccatcatgacaagg     1620
1621 ctccaccctctactgtctgctcatgcctgcctctttcacttggcaggataatgcagtcat    1680
1681 tagaatttcacatgtagtagcttctgagggtaacaacagagtgtcagatatgtcatctca   1740
1741 acctcaaacttttacgtaacatctcaggggaaatgtggctctctccatcttgcatacaggg  1800
1801 ctcccaatagaaatgaacacagagatattgcctgtgtgtttgcagagaagatggtttcta   1860
1861 taaagagtaggaaagctgaaattatagtagagtctcctttaaatgcacattgtgtggatg   1920
1921 gctctcaccatttcctaagagatacagtgtaaaaacgtgacagtaatactgattcttagca  1980
1981 gaataaacatgtaccacatttgcaaaaaa                                   2010
``` pcKGCEA2:

```
   1 gggtggatcctaggctcatctccataggggagaacacacatacagcagagaccatggga                59
                                                              MetGly 60 cccctc tca gcccct ccc tgc act cag cacatcacc tgg aag gggctc ctg ctc aca gca   119
       ProLeuSerAlaProProCysThrGlnHisIleThrTrpLysGlyLeuLeuLeuThrAla 120 tca ctt tta aac ttc tgg aac ctg cccacc act gcccaa gta ataattgaa gcccag cca   179
       SerLeuLeuAsnPheTrpAsnLeuProThrThrAlaGlnValIleIleGluAlaGlnPro 180 ccc aaa gtt tct gag gggaag gat gtt ctt cta ctt gtc cacaat ttg ccccag aat ctt  239
       ProLysValSerGluGlyLysAspValLeuLeuLeuValHisAsnLeuProGlnAsnLeu 240 act ggctac atcgg tac aa gggcaa atg acg gac ctc tac cat tac attaca tca tat    299
       ThrGlyTyrIleTrpTyrLysGlyGlnMetThrAspLeuTyrHisTyrIleThrSerTyr 300 gta gta gac ggt caa attataat gggcct gcctac agt gga cga gaa aca gta tat tcc   359
       ValValAspGlyGlnIleIleTyrGlyProAlaTyrSerGlyArgGluThrValTyrSer 360 aat gcatcc ctg ctg atccag aat gtc aca cag gag gat gcaggatcc tac acc tta cac  419
       AsnAlaSerLeuLeuGlnAsnValThrGlnGluAspAlaGlySerTyrThrLeuHis 420 atcataaag cga ggc gat gggact gga gga gta act gga tat ttc act gtc acc tta tac 479
       IleIleLysArgGlyAspGlyThrGlyGlyValThrGlyTyrPheThrValThrLeuTyr 480 tcg gag act ccc aag cgc tcc atctcc agcagcaac tta aac ccc agg gag gtc atg gag 539
       SerGluThrProLysArgSerIleSerSerSerAsnLeuAsnProArgGluValMetGlu
``` which has been designated SEQ ID No:8 and SEQ ID No:16 for the translated polypeptide.

```
 540 gct gtg cgc tta atcgt gat cct gagact ccggat gcaagctac ctg tgg ttg ctg aat    599
       AlaValArgLeuIleCysAspProGluThrProAspAlaSerTyrLeuTrpLeuLeuAsn 600 ggt cag aac ctc cct atg act cacagg ttg cag ctg tccaaa acc aac agg acc ctc tat 659
       GlyGlnAsnLeuProMetThrHisArgLeuGlnLeuSerLysThrAsnARgThrLeuTyr 660 cta ttt ggt gtc aca aag tat attgcagggccc tat gaa tgt gaa atacgg agg gga gtg  719
       LeuPheGlyValThrLysTyrIleAlaGlyProTyrGluCysGluIleArgArgGlyVal 720 agt gccagccgc agt gac cca gtc acc ctg aat ctc ctc ccgaag ctg cccatg cct tac  779
       SerAlaSerArgSerAspProValThrLeuAsnLeuLeuProLysLeuProMetProTyr 780 atcacc atcaac aac tta aac cccagg gag aag aag gat gtg tta gccttc acc tgt gaa  839
       IleThrIleAsnAsnLeuAsnProArgGluLysLysAspValLeuAlaPheThrCysGlu 840 cct aag agt cgg aac tac acc tac atttgg tgg cta aat ggt cag agcctc ccggtc agt 899
       ProLysSerArgAsnTyrThrTyrIleTrpTrpLeuAsnGlyGlnSerLeuProValSer 900 ccgagg gta aag cga cccattgaa aac agg atactc attcta cccagt gtc acg aga aat    959
       ProArgValLysArgProIleGluAsnArgIleLeuIleLeuProSerValThrArgAsn 960 gaa aca gga ccctat caa tgt gaa atacgg gac cga tat ggt ggcatccgc agtac cca    1019
       GluThrGlyProTyrGlnCysGluIleArgAspArgTyrGlyGlyIleArgSerAsnPro 1020 gtc acc ctg aat gtc ctc tat ggt cca gac ctc cccaga atttac cct tac ttc acc tat 1079
       ValThrLeuAsnValLeuTyrGlyProAspLeuProArgIleTyrProTyrPheThrTyr 1080 tac cgt tca gga gaa aac ctc gac ttg tcc tgc ttt gcggac tct aac cca ccggcagag 1139
       TyrArgSerGlyGluAsnLeuAspLeuSerCysPheAlaAspSerAsnProProAlaGlu 1140 tat ttt tgg aca attaat gggaag ttt cag cta tca gga caa aag ctc ttt atccccaa   1199
       TyrPheTrpThrIleAsnGlyLysPheGlnLeuSerGlyGlnLysLeuPheIleProGln 1200 attact aca aat cat agcgggctc tat gct tgc tct gtt cgt aac tca gccact ggcaag   1259
       IleThrThrAsnHisSerGlyLeuTyrAlaCysSerValArgAsnSerAlaThrGlyLys 1260 gaa atctcc aaa tcc atg atagtc aaa gtc tct ccctgc cat ggaaac cag aca gag      1319
       GluIleSerLysSerMetIleValLysValSerGlyProCysHisTlyAsnGlnThrGlu
```

-continued

```
1320 tct cat taa taatggctgccacaatagagacactgagaaaaagaacaggttgataccttcatg     1379
     SerHisEnd 1380 aaattcaagacaaagaagaaaaaggctcaatgttattggactaaataatcaaaaggataa          1439
1440 tgttttcataattttattggaaaatgtgctgattcttggaatgtttattctccagatt            1499
1500 tatgaacttttttcttcagcaattggtaaagtatacttttgtaaacaaaaattgaaaca           1559
1560 tttgctttgctctctatctgagtgccccccc                                       1591
``` which has been designated SEQ ID No:9 and SEQ ID No:17 for the translated polypeptide.

It will be appreciated that the instant specification and claims are set forth by way of illustration and not limitation and that various modifications and changes may be made without departing from the spirit and scope of the present invention.

SEQUENCE LISTING (1) GENERAL INFORMATION:
- (i) APPLICANT:  BARNETT, THOMAS R
  ELTING, JAMES J
  KAMARCK, MICHAEL E
  KRETSCHMER, A W
- (ii) TITLE OF INVENTION: CDNAS CODING FOR MEMBERS OF THE CARCINOEMBRYONIC ANTIGEN FAMILY
- (iii) NUMBER OF SEQUENCES: 1
- (iv) CORRESPONDENCE ADDRESS:
  - (A) ADDRESSEE: SPRUNG HORN KRAMER & WOODS
  - (B) STREET: 1140 AVENUE OF THE AMERICAS
  - (C) CITY: NEW YORK
  - (D) STATE: NEW YORK
  - (E) COUNTRY: U.S.A.
  - (F) ZIP: 10036
- (v) COMPUTER READABLE FORM:
  - (A) MEDIUM TYPE: Floppy disk
  - (B) COMPUTER: IBM PC compatible
  - (C) OPERATING SYSTEM: PC-DOS/MS-DOS
  - (D) SOFTWARE: PatentIn Release #1.0, Version #1.25
- (vi) CURRENT APPLICATION DATA:
  - (A) APPLICATION NUMBER: US 07/760,031
  - (B) FILING DATE: 13-NOV-1991
  - (C) CLASSIFICATION: UNASSIGNED
- (viii) ATTORNEY/AGENT INFORMATION:
  - (A) NAME: VASTA JR, VINCENT J
  - (B) REGISTRATION NUMBER: 26,655
  - (C) REFERENCE/DOCKET NUMBER: MDI 242.5-VJV
- (ix) TELECOMMUNICATION INFORMATION:
  - (A) TELEPHONE: (212) 391-0520
  - (B) TELEFAX: (212) 382-0949
  - (C) TELEX: 423092 NYP UI (2) INFORMATION FOR SEQ ID NO:1:
- (i) SEQUENCE CHARACTERISTICS:
  - (A) LENGTH: 859 base pairs
  - (B) TYPE: nucleic acid
  - (C) STRANDEDNESS: double
  - (D) TOPOLOGY: linear
- (ii) MOLECULE TYPE: cDNA
- (iii) HYPOTHETICAL: NO
- (iv) ANTI-SENSE: NO
- (vi) ORIGINAL SOURCE:
  - (A) ORGANISM: *HOMO SAPIENS*
- (vii) IMMEDIATE SOURCE:
  - (B) CLONE: CEA-(a) [LV7]
- (xi) SEQUENCE DESCRIPTION: SEQ ID NO:1:

```
GGGGTTTACA  CAACCACCAC  CCCATCAAAC  CCTTCATCAC  CAGCAACAAC  TCCAACCCCG   60
TGGAGGATGA  GGATGCTGTA  GCCTTAACCT  GTGAACCTGA  GATTCAGAAC  ACAACCTACC  120
TGTGGTGGGT  AAATAATCAG  AGCCTCDCCG  GTCAGTCCCA  GGCTGCAGCT  GTCCAATGAC  180
AACAGGACCC  TCACTCTACT  CAGTGTCACA  AGGAATGATG  TAGGACCCTA  TGCGTGTGGA  240
ATCCAGAACG  AATTAAGTGT  TGACCACAGC  GACCCAGTCA  CCCAGCGATT  CCTCTATGGC  300
CCAGACGACC  CCACCATTTC  CCCCTCATAC  ACCTATTACC  GTCAGGGGT   GGAACCTCAG  360
CCTCTCTGCC  ATGCAGCCTC  TAACCCACCT  GCACAGTATT  CTTGGCTGAT  TGATGGGACC  420
GTCCAGCAAC  ACACACAAGA  GCTCTTTATC  TCCAACATCA  CTGAGAAGAA  CAGCGGACTC  480
TATACCTGCC  AGGCCAATAA  CTCAGCCAGT  GGCACAGCAG  GACTACAGTC  AAGACAATCA  540
CAGTCTCTGC  GGATGCCCAG  CCCTCCATCT  CCAGCAACAA  CTCCAAACCC  GTGGAGGACA  600
AGGATCGCTG  TGGCCTTCAC  TGTGAACCTG  AGGCTCAGAA  CACAACCTAC  CTGTGGTGGG  660
TAAATGGTCA  GAGCCTCCCA  GTCAGTCCCA  GGCTGCAGCT  GTCCAATGGC  AACAGGACCC  720
TCACTCTGTT  CAATGTCACA  AGAAATGACG  CAAGAGCCTA  TGTATGTGGA  ATCCAGAACT  780
CAGTGAGTGC  AAACCGCAGT  GACCCAGTCA  CCCTGGATGT  CCTCTATGGG  CCGGACACCC  840
CCATCATTTC  CCCCCCCCC                                                    859
```

SEQUENCE LISTING (1) GENERAL INFORMATION:
- (i) APPLICANT: BARNETT, THOMAS R
  ELTING, JAMES J
  KAMARCK, MICHAEL E
  KRETSCHMER, A W
- (ii) TITLE OF INVENTION: CDNAS CODING FOR MEMBERS OF THE CARCINOEMBRYONIC ANTIGEN FAMILY
- (iii) NUMBER OF SEQUENCES: 1
- (iv) CORRESPONDENCE ADDRESS:
  - (A) ADDRESSEE: SPRUNG HORN KRAMER & WOODS
  - (B) STREET: 1140 AVENUE OF THE AMERICAS
  - (C) CITY: NEW YORK
  - (D) STATE: NEW YORK
  - (E) COUNTRY: U.S.A.
  - (F) ZIP: 10036
- (v) COMPUTER READABLE FORM:
  - (A) MEDIUM TYPE: Floppy disk
  - (B) COMPUTER: IBM PC compatible
  - (C) OPERATING SYSTEM: PC-DOS/MS-DOS
  - (D) SOFTWARE: PatentIn Release #1.0, Version #1.25
- (vi) CURRENT APPLICATION DATA:
  - (A) APPLICATION NUMBER: US 07/760,031
  - (B) FILING DATE: 13-NOV-1991
  - (C) CLASSIFICATION: UNASSIGNED
- (viii) ATTORNEY/AGENT INFORMATION:
  - (A) NAME: VASTA JR, VINCENT J
  - (B) REGISTRATION NUMBER: 26,655
  - (C) REFERENCE/DOCKET NUMBER: MDI 242.5-VJV
- (ix) TELECOMMUNICATION INFORMATION:
  - (A) TELEPHONE: (212) 391-0520
  - (B) TELEFAX: (212) 382-0949
  - (C) TELEX: 423092 NYP UI (2) INFORMATION FOR SEQ ID NO:2:
- (i) SEQUENCE CHARACTERISTICS:
  - (A) LENGTH: 2839 base pairs
  - (B) TYPE: nucleic acid
  - (C) STRANDEDNESS: double
  - (D) TOPOLOGY: linear
- (ii) MOLECULE TYPE: cDNA
- (iii) HYPOTHETICAL: NO
- (iv) ANTI-SENSE: NO
- (vi) ORIGINAL SOURCE:
  - (A) ORGANISM: *HOMO SAPIENS*
- (vii) IMMEDIATE SOURCE:
  - (B) CLONE: CEA-(b) [1LV7]
- (xi) SEQUENCE DESCRIPTION: SEQ ID NO:2:

```
CACCATGGAG TCTCCCTCGG CCCCTCCCCA CAGATGGTGC ATCCCCTGGC AGAGGCTCCT   60
GCTCACAGCC TCACTTCTAA CCTTCTGGAA CCCGCCCACC ACTGCCAAGC TCACTATTGA  120
ATCCACGCCG TTCAATGTCG CAGAGGGGAA GGAGGTGCTT CTACTTGTCC ACAATCTGCC  180
CCAGCATCTT TTTGGCTACA GCTGGTACAA AGGTGAAAGA GTGGATGGCA ACCGTCAAAT  240
TATAGGATAT GTAATAGGAA CTCAACAAGC TACCCCAGGG CCCGCATACA GTGGTCGAGA  300
GATAATATAC CCCAATGCAT CCCTGCTGAT CCAGAACATC ATCCAGAATG ACACAGGATT  360
CTACACCCTA CACGTCATAA AGTCAGATCT TGTGAATGAA GAAGCAACTG GCCAGTTCCG  420
GGTATACCCG GAGCTGCCCA AGCCCTCCAT CTCCAGCAAC AACTCCAAAC CCGTGGAGGA  480
CAAGGATGCT GTGGCCTTCA CCTGTGAACC TGAGACTCAG GACGCAACCT ACCTGTGGTG  540
GGTAAACAAT CAGAGCCTCC CGGTCAGTCC CAGGCTGCAG CTGTCCAATG GCAACAGGAC  600
CCTCACTCTA TTCAATGTCA CAAGAAATGA CACAGCAAGC TACAAATGTG AAACCCAGAA  660
CCCAGTGAGT GCCAGGCGCA GTGATTCAGT CATCCTGAAT GTCCTCTATG GCCCGGATGC  720
CCCCACCATT TCCCCTCTAA ACACATCTTA CAGATCAGGG GAAAATCTGA ACCTCTCCTG  780
CCACGCAGCC TCTAACCCAC CTGCACAGTA CTCTTGGTTT GTCAATGGGA CTTTCCAGCA  840
ATCCACCCAA GAGCTCTTTA TCCCCAACAT CACTGTGAAT AATAGTGGAT CCTATACGTG  900
CCAAGCCCAT AACTCAGACA CTGGCCTCAA TAGGACCACA GTCACGACGA TCACAGTCTA  960
TGCAGAGCCA CCCAAACCCT TCATCACCAG CAACAACTCC AACCCCGTGG AGGATGAGGA 1020
TGCTGTAGCC TTAACCTGTG AACCTGAGAT TCAGAACACA ACCTACCTGT GGTGGGTAAA 1080
TAATCAGAGC CTCCCGGTCA GTCCCAGGCT GCAGCTGTCC AATGACAACA GGACCCTCAC 1140
TCTACTCAGT GTCACAAGGA ATGATGTAGG ACCCTATGAG TGTGGAATCC AGAACGAATT 1200
AAGTGTTGAC CACAGCGACC CAGTCATCCT GAATGTCCTC TATGGCCCAG ACGACCCCAC 1260
CATTTCCCCC TCATACACCT ATTACCGTCC AGGGGTGAAC CTCAGCCTCT CCTGCCATGC 1320
AGCCTCTAAC CCACCTGCAC AGTATTCTTG GCTGATTGAT GGGAACATCC AGCAACACAC 1380
ACAAGAGCTC TTTATCTCCA ACATCACTGA GAAGAACAGC GGACTCTATA CCTGCCAGGC 1440
CAATAACTCA GCCAGTGGCC ACAGCAGGAC TACAGTCAAG ACAATCACAG TCTCTGCGGA 1500
GCTGCCCAAG CCCTCCATCT CCAGCAACAA CTCCAAACCC GTGGAGGACA AGGATGCTGT 1560
GGCCTTCACC TGTGAACCTG AGGCTCAGAA CACAACCTAC CTGTGGTGGG TAAATGGTCA 1620
GAGCCTCCCA GTCAGTCCCA GGCTGCAGCT GTCCAATGGC AACAGGACCC TCACTCTATT 1680
CAATGTCACA AGAAATGACG CAAGAGCCTA TGTATGTGGA ATCCAGAACT CAGTGAGTGC 1740
AAACCGCAGT GACCCAGTCA CCCTGGATGT CCTCTATGGG CCGGACACCC CATCATTTC  1800
CCCCCCAGAC TCGTCTTACC TTTCGGGAGC GAACCTCAAC CTCTCCTGCC ACTCGGCCTC 1860
TAACCCATCC CCGCAGTATT CTTGGCGTAT CAATGGGATA CCGCAGCAAC ACACACAAGT 1920
TCTCTTTATC GCCAAAATCA CGCCAAATAA CAACGGGACC TATGCCTGTT TTGTCTCTAA 1980
CTTGGCTACT GGCCGCAATA ATTCCATAGT CAAGAGCATC ACAGTCTCTG CATCTGGAAC 2040
TTCTCCTGGT CTCTCAGCTG GGGCCACTGT CGGCATCATG ATTGGAGTGC TGGTTGGGGT 2100
```

SEQUENCE LISTING -continued

| | | | | | | |
|---|---|---|---|---|---|---|
| TGCTCTGATA | TAGCAGCCCT | GGTGTAGTTT | CTTCATTTCA | GGAAGACTGA | CAGTTGTTTT | 2160 |
| GCTTCTTCCT | TAAAGCATTT | GCAACAGCTA | CAGTCTAAAA | TTGCTTCTTT | ACCAAGGATA | 2220 |
| TTTACAGAAA | AGACTCTGAC | CAGAGATCGA | GACCATCCTA | GCCAACATCG | TGAAACCCCA | 2280 |
| TCTCTACTAA | AAATACAAAA | ATGAGCTGGG | CTTGGTGGCG | CGCACCTGTA | GTCCCAGTTA | 2340 |
| CTCGGGAGGC | TGAGGCAGGA | GAATCGCTTG | AACCCGGGAG | GTGGAGATTG | CAGTGAGCCC | 2400 |
| AGATCGCACC | ACTGCACTCC | AGTCTGGCAA | CAGAGCAAGA | CTCCATCTCA | AAAAGAAAAG | 2460 |
| AAAAGAAGAC | TCTGACCTGT | ACTCTTGAAT | ACAAGTTTCT | GATACCACTG | CACTGTCTGA | 2520 |
| GAATTTCCAA | AACTTTAATG | AACTAACTGA | CAGCTTCATG | AAACTGTCCA | CCAAGATCAA | 2580 |
| GCAGAGAAAA | TAATTAATTT | CATGGGACTA | AATGAACTAA | TGAGGATAAT | ATTTTCATAA | 2640 |
| TTTTTTATTT | GAAATTTTGC | TGATTCTTTA | AATGTCTTGT | TTCCCAGATT | TCAGGAAACT | 2700 |
| TTTTTTCTTT | TAAGCTATCC | ACAGCTTACA | GCAATTTGAT | AAAATATACT | TTTGTGAACA | 2760 |
| AAAATTGAGA | CATTTACATT | TTCTCCCTAT | GTGGTCGCTC | CAGACTTGGG | AAACTATTCA | 2820 |
| TGAATATTTA | TATTGTATG | | | | | 2839 |

SEQUENCE LISTING (1) GENERAL INFORMATION:
    (i) APPLICANT:   BARNETT, THOMAS R
                         ELTING, JAMES J
                         KAMARCK, MICHAEL E
                         KRETSCHMER, A W
    (ii) TITLE OF INVENTION: CDNAS CODING FOR MEMBERS OF THE
         CARCINOEMBRYONIC ANTIGEN FAMILY
    (iii) NUMBER OF SEQUENCES: 1
    (iv) CORRESPONDENCE ADDRESS:
        (A) ADDRESSEE: SPRUNG HORN KRAMER & WOODS
        (B) STREET: 1140 AVENUE OF THE AMERICAS
        (C) CITY: NEW YORK
        (D) STATE: NEW YORK
        (E) COUNTRY: U.S.A.
        (F) ZIP: 10036
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25
    (vi) CURRENT APPLICATION DATA:
        (A) APPLICATION NUMBER: US 07/760,031
        (B) FILING DATE: 13-NOV-1991
        (C) CLASSIFICATION: UNASSIGNED
    (viii) ATTORNEY/AGENT INFORMATION:
        (A) NAME: VASTA JR, VINCENT J
        (B) REGISTRATION NUMBER: 26,655
        (C) REFERENCE/DOCKET NUMBER: MDI 242.5-VJV
    (ix) TELECOMMUNICATION INFORMATION:
        (A) TELEPHONE: (212) 391-0520
        (B) TELEFAX: (212) 382-0949
        (C) TELEX: 423092 NYP UI (2) INFORMATION FOR SEQ ID NO:3:
    (i) SEQUENCE CHARACTERISTICS:
        (A) LENGTH: 3461 base pairs
        (B) TYPE: nucleic acid
        (C) STRANDEDNESS: double
        (D) TOPOLOGY: linear
    (ii) MOLECULE TYPE: cDNA
    (iii) HYPOTHETICAL: NO
    (iv) ANTI-SENSE: NO
    (vi) ORIGINAL SOURCE:
        (A) ORGANISM: *HOMO SAPIENS*
    (vii) IMMEDIATE SOURCE:
        (B) CLONE: CEA-(c) [16-19]
    (xi) SEQUENCE DESCRIPTION: SEQ ID NO:3:

| | | | | | | |
|---|---|---|---|---|---|---|
| CAGCCGTGCT | CGAAGCGTTC | CTGGAGCCCA | AGCTCTCCTC | CACAGGTGAA | GACAGGGCCA | 60 |
| GCAGGAGACA | CCATGGGGCA | CCTCTCAGCC | CCACTTCACA | GAGTGCGTGT | ACCCTGGCAG | 120 |
| GGGCTTCTGC | TCACAGCCTC | ACTTCTAACC | TTCTGGAACC | CGCCCACCAC | TGCCCAGCTC | 180 |
| ACTACTGAAT | CCATGCCATT | CAATGTTGCA | GAGGGGAAGG | AGGTTCTTCT | CCTTGTCCAC | 240 |
| AATCTGCCCC | AGCAACTTTT | TGGCTACAGC | TGGTACAAAG | GGGAAAGAGT | GGATGGCAAC | 300 |
| CGTCAAATTG | TAGGATATGC | AATAGGAACT | CAACAAGCTA | CCCCAGGGCC | CGCAAACAGC | 360 |
| GGTCGAGAGA | CAATATACCC | CAATGCATCC | CTGCTGATCC | AGAACGTCAC | CCAGAATGAC | 420 |
| ACAGGATTCT | ACACCCTACA | AGTCATAAAG | TCAGATCTTG | TGAATGAAGA | AGCAACTGGA | 480 |
| CAGTTCCATG | TATACCCGGA | GCTGCCCAAG | CCCTCCATCT | CCAGCAACAA | CTCCAACCCT | 540 |
| GTGGAGGACA | AGGATGCTGT | GGCCTTCACC | TATGAACCTG | AGACTCAGGA | CACAACCTAC | 600 |
| CTGTGGTGGA | TAAACAATCA | GAGCCTCCCG | GTCAGTCCCA | GGCTGCAGCT | GTCCAATGGC | 660 |
| AACAGGACCC | TCACTCTACT | CAGTGTCACA | AGGAATGACA | CAGGACCCTA | TGAGTGTGAA | 720 |
| ATACAGAACC | CAGTGAGTGC | GAACCGCAGT | GACCCAGTCA | CCTTGAATGT | CACCTATGGC | 780 |
| CCGGACACCC | CCACCATTTC | CCCTTCAGAC | ACCTATTACC | GTCCAGGGGC | AAACCTCAGC | 840 |
| CTCTCCTGCT | ATGCAGCCTC | TAACCCACCT | GCACAGTACT | CCTGGCTTAT | CAATGGAACA | 900 |
| TTCCAGCAAA | GCACACAAGA | GCTCTTTATC | CCTAACATCA | CTGTGAATAA | TAGTGGATCC | 960 |

-continued

SEQUENCE LISTING

| | | | | | | |
|---|---|---|---|---|---|---|
| TATACCTGCC | ACGCCAATAA | CTCAGTCACT | GGCTGCAACA | GGACCACAGT | CAAGACGATC | 1020 |
| ATAGTCACTG | AGCTAAGTCC | AGTAGTAGCA | AAGCCCCAAA | TCAAAGCCAG | CAAGACCACA | 1080 |
| GTCACAGGAG | ATAAGGACTC | TGTGAACCTG | ACCTGCTCCA | CAAATGACAC | TGGAATCTCC | 1140 |
| ATCCGTTGGT | TCTTCAAAAA | CCAGATCTC | CCGTCCTCGG | AGAGGATGAA | GCTGTCCCAG | 1200 |
| GGCAACACCA | CCCTCAGCAT | AAACCCTGTC | AAGAGGGAGG | ATGCTGGGAC | GTATTGGTGT | 1260 |
| GAGGTCTTCA | ACCCAATCAG | TAAGAACCAA | AGCGACCCCA | TCATGCTGAA | CGTAAACTAT | 1320 |
| AATGCTCTAC | CACAAGAAAA | TGGCCTCTCA | CCTGGGGCCA | TTGCTGGCAT | TGTGATTGGA | 1380 |
| GTAGTGGCCC | TGGTTGCTCT | GATAGCAGTA | GCCCTGGCAT | GTTTTCTGCA | TTTCGGGAAG | 1440 |
| ACCGGCAGGG | CAAGCGACCA | GCGTGATCTC | ACAGAGCACA | AACCCTCAGT | CTCCAACCAC | 1500 |
| ACTCAGGACC | ACTCCAATGA | CCCACCTAAC | AAGATGAATG | AAGTTACTTA | TTCTACCCTG | 1560 |
| AACTTTGAAG | CCCAGCAACC | CACACAACCA | ACTTCAGCCT | CCCCATCCCT | AACAGCCACA | 1620 |
| GAAATAATTT | ATTCAGAAGT | AAAAAAGCAG | TAATGAAACC | TGTCCTGCTC | ACTGCAGTGC | 1680 |
| TGATGTATTT | CAAGTCTCTC | ACCCTCATCA | CTAGGAGATT | CCTTTCCCCT | GTAGGGTAGA | 1740 |
| GGGGTGGGGA | CAGAAACAAC | TTTCTCCTAC | TCTTCCTTCC | TAATAGGCAT | CTCCAGGCTG | 1800 |
| CCTGGTCACT | GCCCCTCTCT | CAGTGTCAAT | AGATGAAAGT | ACATTGGGAG | TCTGTAGGAA | 1860 |
| ACCCAACCTT | CTTGTCATTG | AAATTTGGCA | AAGCTGACTT | TGGGAAAGAG | GGACCAGAAC | 1920 |
| TTCCCCTCCC | TTCCCCTTTT | CCCAACCTGG | ACTTGTTTTA | AACTTGCCTG | TTCAGAGCAC | 1980 |
| TCATTCCTTC | CCACCCCCAG | TCCTGTCCTA | TCACTCTAAT | TCGGATTTGC | CATAGCCTTG | 2040 |
| AGGTTATGTC | CTTTTCCATT | AAGTACATGT | GCCAGGAAAC | AGCGAGAGAG | AGAAAGTAAA | 2100 |
| CGGCAGTAAT | GCTTCTCCTA | TTTCTCCAAA | GCCTTGTGTG | AACTAGCAAA | GAGAAGAAAA | 2160 |
| TCAAATATAT | AACCAATAGT | GAAATGCCAC | AGGTTTGTCC | ACTGTCAGGG | TTGTCTACCT | 2220 |
| GTAGGATCAG | GGTCTAAGCA | CCTTGGTGCT | TAGCTAGAAT | ACCACCTAAT | CCTTCTGGCA | 2280 |
| AGCCTGTCTT | CAGAGAACCC | ACTAGAAGCA | ACTAGGAAAA | ATCACTTGCC | AAAATCCAAG | 2340 |
| GCAATTCCTG | ATGGAAAATG | CAAAAGCACA | TATATGTTTT | AATATCTTTA | TGGGCTCTGT | 2400 |
| TCAAGGCAGT | GCTGAGAGGG | AGGGGTTATA | GCTTCAGGAG | GGAACCAGCT | TCTGATAAAC | 2460 |
| ACAATCTGCT | AGGAACTTGG | GAAAGGAATC | AGAGAGCTGC | CCTTCAGCGA | TTATTTAAAT | 2520 |
| TGTTAAAGAA | TACACAATTT | GGGGTATTGG | GATTTTTCTC | CTTTTCTCTG | AGACATTCCA | 2580 |
| CCATTTTAAT | TTTTGTAACT | GCTTATTTAT | GTGAAAAGGG | TTATTTTTAC | TTAGCTTAGC | 2640 |
| TATGTCAGCC | AATCCGATTG | CCTTAGGTGA | AAGAAACCAC | CGAAATCCCT | CAGGTCCCTT | 2700 |
| GGTCAGGAGC | CTCTCAAGAT | TTTTTTTGTC | AGAGGCTCCA | AATAGAAAAT | AAGAAAAGGT | 2760 |
| TTTCTTCATT | CATGGCTAGA | GCTAGATTTA | ACTCAGTTTC | TAGGCACCTC | AGACCAATCA | 2820 |
| TCAACTACCA | TTCTATTCCA | TGTTTGCACC | TGTGCATTTT | CTGTTTGCCC | CCATTCACTT | 2880 |
| TGTCAGGAAA | CCTTGGCCTC | TGCTAAGGTG | TATTTGGTCC | TTGAGGACATG | GGAGCACCCT | 2940 |
| ACAGGGACAC | TATCACTCAT | GCTGGTGGCA | TTGTTTACAG | CTAGAAAGCT | GCACTGGTGC | 3000 |
| TAATGCCCCT | TGGGAAATGG | GGCTGTGAGG | AGGAGGATTA | TAACTTAGGC | CTAGCCTCTT | 3060 |
| TTAACAGCCT | CTGAAATTTA | TCTTTTCTTC | TATGGGGTCT | ATAAATGTAT | CTTATAATAA | 3120 |
| AAAGGAAGGA | CAGGAGGAAA | ACAGGCAAAT | GTACTTCTCA | CCCAGTCTTC | TACACAGATG | 3180 |
| GAATCTCTTT | GGGGCTAAGA | GAAAGGTTTT | ATTCTATATT | GCTTACCTGA | TCTCATGTTA | 3240 |
| GGCCTAAGAG | GCTTTCTCCA | GGAGGATTAG | CTTGGAGTTC | TCTATACTCA | GGTACCTCTT | 3300 |
| TCAGGGTTTT | CTAACCCTGA | CACGGACTGT | GCATACTTTC | CCTCATCCAT | GCTGTGCTGT | 3360 |
| GTTATTTAAT | TTTTCCTGGC | TAAGATCATG | TCTGAATTAT | GTATGAAAAT | TATTCTATGT | 3420 |
| TTTTATAATA | AAAATAATAT | ATCAGACATC | GAAAAAAAAA | A | | 3461 |

SEQUENCE LISTING (1) GENERAL INFORMATION:
    (i) APPLICANT:    BARNETT, THOMAS R
                      ELTING, JAMES J
                      KAMARCK, MICHAEL E
                      KRETSCHMER, A W
    (ii) TITLE OF INVENTION: CDNAS CODING FOR MEMBERS OF THE
         CARCINOEMBRYONIC ANTIGEN FAMILY
    (iii) NUMBER OF SEQUENCES: 1
    (iv) CORRESPONDENCE ADDRESS:
        (A) ADDRESSEE: SPRUNG HORN KRAMER & WOODS
        (B) STREET: 1140 AVENUE OF THE AMERICAS
        (C) CITY: NEW YORK
        (D) STATE: NEW YORK
        (E) COUNTRY: U.S.A.
        (F) ZIP: 10036
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25
    (vi) CURRENT APPLICATION DATA:
        (A) APPLICATION NUMBER: US 07/760,031
        (B) FILING DATE: 13-NOV-1991
        (C) CLASSIFICATION: UNASSIGNED
    (viii) ATTORNEY/AGENT INFORMATION:
        (A) NAME: VASTA JR, VINCENT J
        (B) REGISTRATION NUMBER: 26,655
        (C) REFERENCE/DOCKET NUMBER: MDI 242.5-VJV
    (ix) TELECOMMUNICATION INFORMATION:
        (A) TELEPHONE: (212) 391-0520
        (B) TELEFAX: (212) 382-0949
        (C) TELEX: 423092 NYP UI
(2) INFORMATION FOR SEQ ID NO:4:

-continued

SEQUENCE LISTING (i) SEQUENCE CHARACTERISTICS:
    (A) LENGTH: 1964 base pairs
    (B) TYPE: nucleic acid
    (C) STRANDEDNESS: double
    (D) TOPOLOGY: linear
(ii) MOLECULE TYPE: cDNA
(iii) HYPOTHETICAL: NO
(iv) ANTI-SENSE: NO
(vi) ORIGINAL SOURCE:
    (A) ORGANISM: *HOMO SAPIENS*
(vii) IMMEDIATE SOURCE:
    (B) CLONE: CEA-(d) [BT-20]
(xi) SEQUENCE DESCRIPTION: SEQ ID NO:4:

| | | | | | | |
|---|---|---|---|---|---|---|
| CCGGGGACA | CGCAGGGCCA | ACAGTCACAG | CAGCCCTGAC | CAGAGCATTC | CTGGAGCTCA | 60 |
| AGCTCTCTAC | AAAGAGGTGG | ACAGAGAAGA | CAGCAGAGAC | CATGGGACCC | CCCTCAGCCC | 120 |
| CTCCCTGCAG | ATTGCATGTC | CCCTGGAAGG | AGGTCCTGCT | CACAGCCTCA | CTTCTAACCT | 180 |
| TCTGGAACCC | ACCCACCACT | GCCAAGCTCA | CTATTGAATC | CACGCCATTC | AATGTCGCAG | 240 |
| AGGGGAAGGA | GGTTCTTCTA | CTCGCCACA | ACCTGCCCCA | GAATCGTATT | GGTTACAGCT | 300 |
| GGTACAAAGG | CGAAAGAGTG | GATGGCAACA | GTCTAATTGT | AGGATATGTA | ATAGGAACTC | 360 |
| AACAAGCTAC | CCCAGGGCCC | GCATACAGTG | GTCGAGAGAC | AATATACCCC | AATGCATCCC | 420 |
| TGCTGATCCA | GAACGTCACC | CAGAATGACA | CAGGATTCTA | CACCCTACAA | GTCATAAAGT | 480 |
| CAGATCTTGT | GAATGAAGAA | GCAACCGGAC | AGTTCCATGT | ATACCCGGAG | CTGCCCAAGC | 540 |
| CCTCCATCTC | CAGCAACAAC | TCCAACCCCG | TGGAGGACAA | GGATGCTGTG | GCCTTCACCT | 600 |
| GTGAACCTGA | GGTTCAGAAC | ACAACCTACC | TGTGGTGGGT | AAATGGTCAG | AGCCTCCCGG | 660 |
| TCAGTCCCAG | GCTGCAGCTG | TCCAATGGCA | ACAGGACCCT | CACTCTACTC | AGCGTCAAAA | 720 |
| GGAACGATGC | AGGATCGTAT | GAATGTGAAA | TACAGAACCC | AGCGAGTGCC | AACCGCAGTG | 780 |
| ACCCAGTCAC | CCTGAATGTC | CTCTATGGCC | CAGATGGCCC | CACCATTTCC | CCCTCAAAGG | 840 |
| CCAATTACCG | TCCAGGGGAA | AATCTGAACC | TCTCCTGCCA | CGCAGCCTCT | AACCCACCTG | 900 |
| CACAGTACTC | TTGGTTTATC | AATGGGACGT | TCCAGCAATC | CACACAAGAG | CTCTTTATCC | 960 |
| CCAACATCAC | TGTGAATAAT | AGCGGATCCT | ATATGTGCCA | AGCCCATAAC | TCAGCCACTG | 1020 |
| GCCTCAATAG | GACCACAGTC | ACGATGATCA | CAGTCTCTGG | AAGTGCTCCT | GTCCTCTCAG | 1080 |
| CTGTGGCCAC | CGTCGGCATC | ACGATTGGAG | TGCTGGCCAG | GGTGGCTCTG | ATATAGCAGC | 1140 |
| CCTGGTGTAT | TTTCGATATT | TCAGGAAGAC | TGGCAGATTG | GACCAGACCC | TGAATTCTTC | 1200 |
| TAGCTCCTCC | AATCCCATTT | TATCCCATGG | AACCACTAAA | AACAAGGTCT | GCTCTGCTCC | 1260 |
| TGAAGCCCTA | TATGCTGGAG | ATGGACAACT | CAATGAAAAT | TTAAAGGGAA | AACCCTCAGG | 1320 |
| CCTGAGGTGT | GTGCCACTCA | GAGACTTCAC | CTAACTAGAG | ACAGGCAAAC | TGCNNNCCAN | 1380 |
| NCCTCTTTCG | CTTGGCAGGN | TGATGCTGTC | ATTAGTATTT | CACAAGAAGT | AGCTTCAGAG | 1440 |
| GGTAACTTAA | CAGAGTATCA | GATCTATCTT | GTCAATCCCA | ACGTTTTACA | TAAAATAAGA | 1500 |
| GATCCTTTAG | TGCACCCAGT | GACTGACATT | AGCAGCATCT | TTAACACAGC | CGTGTGTTCA | 1560 |
| AATGTACAGT | GGTCCTTTTC | AGAGTTGGNN | NTACTCCAAC | TGAAATGTTA | AGGAAGAAGA | 1620 |
| TAGATCCAAT | TAAAAAAAAT | TAAAACCAAT | TTAAAAAAAA | AAAAGAACAC | AGGAGATTCC | 1680 |
| AGTCTACTTG | AGTTAGCATA | ATACAGAAGT | CCCCTCTACT | TTAACTTTTA | CAAAAAAGTA | 1740 |
| ACCTGAACTA | ATCTGATTGT | AACCAATGTA | TTTATTTCTG | TGGTTCTGTT | TCCTTGTTCC | 1800 |
| AATTTGACAA | AACCCACTGT | TCTTGTATTG | TATTGCCAGG | GGGGAGCTAT | CACTGTACTT | 1860 |
| GTAGAGTGGT | GCTGCTTTAA | GTTCATAAAT | CACAAATAAA | AGCCAATTAG | CTCTATAACT | 1920 |
| AAAAAAAAAA | AAAAAAAAAA | AAAAAAAAAA | AAAAAAAAAA | AAAA | | 1964 |

SEQUENCE LISTING (1) GENERAL INFORMATION:
    (i) APPLICANT:   BARNETT, THOMAS R
                       ELTING, JAMES J
                       KAMARCK, MICHAEL E
                       KRETSCHMER, A W
    (ii) TITLE OF INVENTION: CDNAS CODING FOR MEMBERS OF THE CARCINOEMBRYONIC ANTIGEN FAMILY
    (iii) NUMBER OF SEQUENCES: 1
    (iv) CORRESPONDENCE ADDRESS:
        (A) ADDRESSEE: SPRUNG HORN KRAMER & WOODS
        (B) STREET: 1140 AVENUE OF THE AMERICAS
        (C) CITY: NEW YORK
        (D) STATE: NEW YORK
        (E) COUNTRY: U.S.A.
        (F) ZIP: 10036
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25
    (vi) CURRENT APPLICATION DATA:
        (A) APPLICATION NUMBER: US 07/760,031
        (B) FILING DATE: 13-NOV-1991
        (C) CLASSIFICATION: UNASSIGNED
    (viii) ATTORNEY/AGENT INFORMATION:
        (A) NAME: VASTA JR, VINCENT J
        (B) REGISTRATION NUMBER: 26,655
        (C) REFERENCE/DOCKET NUMBER: MDI 242.5-VJV
    (ix) TELECOMMUNICATION INFORMATION:

SEQUENCE LISTING (A) TELEPHONE: (212) 391-0520
(B) TELEFAX: (212) 382-0949
(C) TELEX: 423092 NYP UI (2) INFORMATION FOR SEQ ID NO:5:
   (i) SEQUENCE CHARACTERISTICS:
      (A) LENGTH: 3173 base pairs
      (B) TYPE: nucleic acid
      (C) STRANDEDNESS: double
      (D) TOPOLOGY: linear
   (ii) MOLECULE TYPE: cDNA
   (iii) HYPOTHETICAL: NO
   (iv) ANTI-SENSE: NO
   (vi) ORIGINAL SOURCE:
      (A) ORGANISM: *HOMO SAPIENS*
   (vii) IMMEDIATE SOURCE:
      (B) CLONE: CEA-(e) [E22]
   (xi) SEQUENCE DESCRIPTION: SEQ ID NO:5:

```
CAGCCGTGCT  CGAAGCGTTC  CTGGAGCCCA  AGCTCTCCTC  CACAGGTGAA  GACAGGGCCA    60
GCAGGAGACA  CCATGGGGCA  CCTCTCAGCC  CCACTTCACA  GAGTGCGTGT  ACCCTGGCAG   120
GGGCTTCTGC  TCACAGCCTC  ACTTCTAACC  TTCTGGAACC  CGCCCACCAC  TGCCCAGCTC   180
ACTACTGAAT  CCATGCCATT  CAATGTTGCA  GAGGGGAAGG  AGGTTCTTCT  CCTTGTCCAC   240
AATCTGCCCC  AGCAACTTTT  TGGCTACAGC  TGGTACAAAG  GGGAAAGAGT  GGATGGCAAC   300
CGTCAAATTG  TAGGATATGC  AATAGGAACT  CAACAAGCTA  CCCCAGGGCC  CGCAAACAGC   360
GGTCGAGAGA  CAATATACCC  CAATGCATCC  CTGCTGATCC  AGAACGTCAC  CCAGAATGAC   420
ACAGGATTCT  ACACCCTACA  AGTCATAAAG  TCAGATCTTG  TGAATGAAGA  AGCAACTGGA   480
CAGTTCCATG  TATACCCGGA  GCTGCCCAAG  CCCTCCATCT  CCAGCAACAA  CTCCAACCCT   540
GTGGAGGACA  AGGATGCTGT  GGCCTTCACC  TGTGAACCTG  AGACTCAGGA  CACAACCTAC   600
CTGTGGTGGA  TAAACAATCA  GAGCCTCCCG  GTCAGTCCCA  GGCTGCAGCT  GTCCAATGGC   660
AACAGGACCC  TCACTCTACT  CAGTGTCACA  AGGAATGACA  CAGGACCCTA  TGAGTGTGAA   720
ATACAGAACC  CAGTGAGTGC  GAACCGCAGT  GACCCAGTCA  CCTTGAATGT  CACCTATGGC   780
CCGGACACCC  CCACCATTTC  CCCTTCAGAC  ACCTATTACC  GTCCAGGGGC  AAACCTCAGC   840
CTCTCCTGCT  ATGCAGCCTC  TAACCCACCT  GCACAGTACT  CCTGGCTTAT  CAATGGAACA   900
TTCCAGCAAA  GCACACAAGA  GCTCTTTATC  CCTAACATCA  CTGTGAATAA  TAGTGGATCC   960
TATACCTGCC  ACGCCAATAA  CTCAGTCACT  GGCTGCAACA  GGACCACAGT  CAAGACGATC  1020
ATAGTCACTG  ATAATGCTCT  ACCACAAGAA  AATGGCCTCT  CACCTGGGGC  CATTGCTGGC  1080
ATTGTGATTG  GAGTAGTGGC  CCTGGTTGCT  CTGATAGCAG  TAGCCCTGGC  ATGTTTTCTG  1140
CATTTCGGGA  AGACCGGCAG  GGCAAGCGAC  CAGCGTGATC  TCACAGAGCA  CAAACCCTCA  1200
GTCTCCAACC  ACACTCAGGA  CCACTCCAAT  GACCCACCTA  ACAAGATGAA  TGAAGTTACT  1260
TATTCTACCC  TGAACTTTGA  AGCCCAGCAA  CCCACACAAC  CAACTTCAGC  CTCCCCATCC  1320
CTAACAGCCA  CAGAAATAAT  TTATTCAGAA  GTAAAAAAGC  AGTAATGAAA  CCTGTCCTGC  1380
TCACTGCAGT  GCTGATGTAT  TTCAAGTCTC  TCACCCTCAT  CACTAGGAGA  TTCCTTTCCC  1440
CTGTAGGGTA  GAGGGGTGGG  GACAGAAACA  ACTTTCTCCT  ACTCTTCCTT  CCTAATAGGC  1500
ATCTCCAGGC  TGCCTGGTCA  CTGCCCCTCT  CTCAGTGTCA  ATAGATGAAA  GTACATTGGG  1560
AGTCTGTAGG  AAACCCAACC  TTCTTGTCAT  TGAAATTTGG  CAAAGCTGAC  TTTGGGAAAG  1620
AGGGACCAGA  ACTTCCCCTC  CCTTCCCCTT  TTCCCAACCT  GGACTTGTTT  TAAACTTGCC  1680
TGTTCAGAGC  ACTCATTCCT  TCCCACCCCC  AGTCCTGTCC  TATCACTCTA  ATTCGGATTT  1740
GCCATAGCCT  TGAGGTTATG  TCCTTTTCCA  TTAAGTACAT  GTGCCAGGAA  ACAGCGAGAG  1800
AGAGAAAGTA  AACGGCAGTA  ATGCTTCTCC  TATTTCTCCA  AAGCCTTGTG  TGAACTAGCA  1860
AAGAGAAGAA  AATCAAATAT  ATAACCAATA  GTGAAATGCC  ACAGGTTTGT  CCACTGTCAG  1920
GGTTGTCTAC  CTGTAGGATC  AGGGTCTAAG  CACCTTGGTG  CTTAGCTAGA  ATACCACCTA  1980
ATCCTTCTGG  CAAGCCTGTC  TTCAGAGAAC  CCACTAGAAG  CAACTAGGAA  AAATCACTTG  2040
CCAAAATCCA  AGGCAATTCC  TGATGGAAAA  TGCAAAAGCA  CATATATGTT  TTAATATCTT  2100
TATGGGCTCT  GTTCAAGGCA  GTGCTGAGAG  GGAGGGGTTA  TAGCTTCAGG  AGGGAACCAG  2160
CTTCTGATAA  ACACAATCTG  CTAGGAACTT  GGGAAAGGAA  TCAGAGAGCT  GCCCTTCAGC  2220
GATTATTTAA  ATTATTGTTA  AAGAATACAC  AATTTGGGGT  ATTGGGATTT  TTCTCCTTTT  2280
CTCTGAGACA  TTCCACCATT  TTAATTTTTG  TAACTGCTTA  TTTATGTGAA  AAGGGTTATT  2340
TTTACTTAGC  TTAGCTATGT  CAGCCAATCC  GATTGCCTTA  GGTGAAAGAA  ACCACCGAAA  2400
TCCCTCAGGT  CCCTTGGTCA  GGAGCCTCTC  AAGATTTTTT  TTGTCAGAGG  CTCCAAATAG  2460
AAAATAAGAA  AAGGTTTTCT  TCATTCATGG  CTAGAGCTAG  ATTTAACTCA  GTTTCTAGGC  2520
ACCTCAGACC  AATCATCAAC  TACCATTCTA  TTCCATGTTT  GCACCTGTGC  ATTTTCTGTT  2580
TGCCCCCATT  CACTTTGTCA  GGAAACCTTG  GCCTCTGCTA  AGGTGTATTT  GGTCCTTGAG  2640
AAGTGGGAGC  ACCCTACAGG  GACACTATCA  CTCATGCTGG  TGGCATTGTT  TACAGCTAGA  2700
AAGCTGCACT  GGTGCTAATG  CCCCTTGGGA  AATGGGGCTG  TGAGGAGGAG  GATTATAACT  2760
TAGGCCTAGC  CTCTTTTAAC  AGCCTCTGAA  ATTTATCTTT  TCTTCTATGG  GGTCTATAAA  2820
TGTATCTTAT  AATAAAAAGG  AAGGACAGGA  GGAAGACAGG  CAAATGTACT  TCTCACCCAG  2880
TCTTCTACAC  AGATGGAATC  TCTTTGGGGC  TAAGAGAAAG  GTTTTATTCT  ATATTGCTTA  2940
CCTGATCTCA  TGTTAGGCCT  AAGAGGCTTT  CTCCAGGAGG  ATTAGCTTGG  AGTTCTCTAT  3000
ACTCAGGTAC  CTCTTTCAGG  GTTTTCTAAC  CCTGACACGG  ACTGTGCATA  CTTTCCCTCA  3060
TCCATGCTGT  GCTGTGTTAT  TTAATTTTTC  CTGGCTAAGA  TCATGTCTGA  ATTATGTATG  3120
AAAATTATTC  TATGTTTTTA  TAATAAAAAT  AATATATCAG  ACATCGAAAA  AAA         3173
```

SEQUENCE LISTING (1) GENERAL INFORMATION:
   (i) APPLICANT:    BARNETT, THOMAS R
                           ELTING, JAMES J
                           KAMARCK, MICHAEL E
                           KRETSCHMER, A W

SEQUENCE LISTING (ii) TITLE OF INVENTION: CDNAS CODING FOR MEMBERS OF THE CARCINOEMBRYONIC ANTIGEN FAMILY
(iii) NUMBER OF SEQUENCES: 1
(iv) CORRESPONDENCE ADDRESS:
   (A) ADDRESSEE: SPRUNG HORN KRAMER & WOODS
   (B) STREET: 1140 AVENUE OF THE AMERICAS
   (C) CITY: NEW YORK
   (D) STATE: NEW YORK
   (E) COUNTRY: U.S.A.
   (F) ZIP: 10036
(v) COMPUTER READABLE FORM:
   (A) MEDIUM TYPE: Floppy disk
   (B) COMPUTER: IBM PC compatible
   (C) OPERATING SYSTEM: PC-DOS/MS-DOS
   (D) SOFTWARE: PatentIn Release #1.0, Version #1.25
(vi) CURRENT APPLICATION DATA:
   (A) APPLICATION NUMBER: US 07/760,031
   (B) FILING DATE: 13-NOV-1991
   (C) CLASSIFICATION: UNASSIGNED
(viii) ATTORNEY/AGENT INFORMATION:
   (A) NAME: VASTA JR, VINCENT J
   (B) REGISTRATION NUMBER: 26,655
   (C) REFERENCE/DOCKET NUMBER: MDI 242.5-VJV
(ix) TELECOMMUNICATION INFORMATION:
   (A) TELEPHONE: (212) 391-0520
   (B) TELEFAX: (212) 382-0949
   (C) TELEX: 423092 NYP UI (2) INFORMATION FOR SEQ ID NO:6:
   (i) SEQUENCE CHARACTERISTICS:
      (A) LENGTH: 1630 base pairs
      (B) TYPE: nucleic acid
      (C) STRANDEDNESS: double
      (D) TOPOLOGY: linear
   (ii) MOLECULE TYPE: cDNA
   (iii) HYPOTHETICAL: NO
   (iv) ANTI-SENSE: NO
   (vi) ORIGINAL SOURCE:
      (A) ORGANISM: *HOMO SAPIENS*
   (vii) IMMEDIATE SOURCE:
      (B) CLONE: CEA-(f) [HT-6]
   (xi) SEQUENCE DESCRIPTION: SEQ ID NO:6:

| | | | | | | |
|---|---|---|---|---|---|---|
| CAGCCGTGCT | CGAAGCGTTC | CTGGAGCCCA | AGCTCTCCTC | CACAGGTGAA | GACAGGGCCA | 60 |
| GCAGGAGACA | CCATGGGGCA | CCTCTCAGCC | CCACTTCACA | GAGTGCGTGT | ACCCTGGCAG | 120 |
| GGGCTTCTGC | TCACAGCCTC | ACTTCTAACC | TTCTGGAACC | CGCCCACCAC | TGCCCAGCTC | 180 |
| ACTACTGAAT | CCATGCCATT | CAATGTTGCA | GAGGGGAAGG | AGGTTCTTCT | CCTTGTCCAC | 240 |
| AATCTGCCCC | AGCAACTTTT | TGGCTACAGC | TGGTACAAAG | GGGAAGAGT | GGATGGCAAC | 300 |
| CGTCAAATTG | TAGGATATGC | AATAGGAACT | CAACAAGCTA | CCCCAGGGCC | CGCAAACAGC | 360 |
| GGTCGAGAGA | CAATATACCC | CAATGCATCC | CTGCTGATCC | AGAACGTCAC | CCAGAATGAC | 420 |
| ACAGGATTCT | ACACCCTACA | AGTCATAAAG | TCAGATCTTG | TGAATGAAGA | AGCAACTGGA | 480 |
| CAGTTCCATG | TATACCCGGA | GCTGCCCAAG | CCCTCCATCT | CCAGCAACAA | CTCCAACCCT | 540 |
| GTGGAGGACA | AGGATGCTGT | GGCCTTCACC | TGTGAACCTG | AGACTCAGGA | CACAACCTAC | 600 |
| CTGTGGTGGA | TAAACAATCA | GAGCCTCCCG | GTCAGTCCA | GGCTGCAGCT | GTCCAATGGC | 660 |
| AACAGGACCC | TCACTCTACT | CAGTGTCACA | AGGAATGACA | CAGGACCCTA | TGAGTGTGAA | 720 |
| ATACAGAACC | CAGTGAGTGC | GAACCGCAGT | GACCCAGTCA | CCTTGAATGT | CACCTATGGC | 780 |
| CCGGACACCC | CCACCATTTC | CCCTTCAGAC | ACCTATTACC | GTCCAGGGGC | AAACCTCAGC | 840 |
| CTCTCCTGCT | ATGCAGCCTC | TAACCCACCT | GCACAGTACT | CCTGGCTTAT | CAATGGAACA | 900 |
| TTCCAGCAAA | GCACACAAGA | GCTCTTTATC | CCTAACATCA | CTGTGAATAA | TAGTGGATCC | 960 |
| TATACCTGCC | ACGCCAATAA | CTCAGTCACT | GGCTGCAACA | GGACCACAGT | CAAGACGATC | 1020 |
| ATAGTCACTG | AGCTAAGTCC | AGTAGTAGCA | AAGCCCCAAA | TCAAAGCCAG | CAAGACCACA | 1080 |
| GTCACAGGAG | ATAAGGACTC | TGTGAACCTG | ACCTGCTCCA | CAAATGACAC | TGGAATCTCC | 1140 |
| ATCCGTTGGT | TCTTCAAAAA | CCAGAGTCTC | CCGTCCTCGG | AGAGGATGAA | GCTGTCCCAG | 1200 |
| GGCAACACCA | CCCTCAGCAT | AAACCCTGTC | AAGAGGGAGG | ATGCTGGGAC | GTATTGGTGT | 1260 |
| GAGGTCTTCA | ACCCAATCAG | TAAGAACCAA | AGCGACCCCA | TCATGCTGAA | CGTAAACTAT | 1320 |
| AATGCTCTAC | CACAAGAAAA | TGGCCTCTCA | CCTGGGGCCA | TTGCTGGCAT | TGTGATTGGA | 1380 |
| GTAGTGGCCC | TGGTTGCTCT | GATAGCAGTA | GCCCTGGCAT | GTTTTCTGCA | TTTCGGGAAG | 1440 |
| ACCGGCAGCT | CAGGACCACT | CCAATGACCC | ACCTAACAAG | ATGAATGAAG | TTACTTATTC | 1500 |
| TACCCTGAAC | TTTGAAGCCC | AGCAACCCAC | ACAACCAACT | TCAGCCTCCC | CATCCCTAAC | 1560 |
| AGCCACAGAA | ATAATTTATT | CAGAAGTAAA | AAAGCAGTAA | TGAAACCTGA | AAAAAAAAAA | 1620 |
| AAAAAAAAAA | | | | | | 1630 |

SEQUENCE LISTING (1) GENERAL INFORMATION:
   (i) APPLICANT: BARNETT, THOMAS R
      ELTING, JAMES J
      KAMARCK, MICHAEL E
      KRETSCHMER, A W
   (ii) TITLE OF INVENTION: CDNAS CODING FOR MEMBERS OF THE

SEQUENCE LISTING

CARCINOEMBRYONIC ANTIGEN FAMILY
  (iii) NUMBER OF SEQUENCES: 1
  (iv) CORRESPONDENCE ADDRESS:
      (A) ADDRESSEE: SPRUNG HORN KRAMER & WOODS
      (B) STREET: 1140 AVENUE OF THE AMERICAS
      (C) CITY: NEW YORK
      (D) STATE: NEW YORK
      (E) COUNTRY: U.S.A.
      (F) ZIP: 10036
  (v) COMPUTER READABLE FORM:
      (A) MEDIUM TYPE: Floppy disk
      (B) COMPUTER: IBM PC compatible
      (C) OPERATING SYSTEM: PC-DOS/MS-DOS
      (D) SOFTWARE: PatentIn Release #1.0, Version #1.25
  (vi) CURRENT APPLICATION DATA:
      (A) APPLICATION NUMBER: US 07/760,031
      (B) FILING DATE: 13-NOV-1991
      (C) CLASSIFICATION: UNASSIGNED
  (viii) ATTORNEY/AGENT INFORMATION:
      (A) NAME: VASTA JR, VINCENT J
      (B) REGISTRATION NUMBER: 26,655
      (C) REFERENCE/DOCKET NUMBER: MDI 242.5-VJV
  (ix) TELECOMMUNICATION INFORMATION:
      (A) TELEPHONE: (212) 391-0520
      (B) TELEFAX: (212) 382-0949
      (C) TELEX: 423092 NYP UI
(2) INFORMATION FOR SEQ ID NO:7:
  (i) SEQUENCE CHARACTERISTICS:
      (A) LENGTH: 1339 base pairs
      (B) TYPE: nucleic acid
      (C) STRANDEDNESS: double
      (D) TOPOLOGY: linear
  (ii) MOLECULE TYPE: cDNA
  (iii) HYPOTHETICAL: YES
  (iv) ANTI-SENSE: NO
  (vii) IMMEDIATE SOURCE:
      (B) CLONE: CEA-(g)
  (xi) SEQUENCE DESCRIPTION: SEQ ID NO:7:

| | | | | | | |
|---|---|---|---|---|---|---|
| CAGCCGTGCT | CGAAGCGTTC | CTGGAGCCCA | AGCTCTCCTC | CACAGGTGAA | GACAGGGCCA | 60 |
| GCAGGAGACA | CCATGGGGCA | CCTCTCAGCC | CCACTTCACA | GAGTGCGTGT | ACCCTGGCAG | 120 |
| GGGCTTCTGC | TCACAGCCTC | ACTTCTAACC | TTCTGGAACC | CGCCCACCAC | TGCCCAGCTC | 180 |
| ACTACTGAAT | CCATGCCATT | CAATGTTGCA | GAGGGGAAGG | AGGTTCTTCT | CCTTGTCCAC | 240 |
| AATCTGCCCC | AGCAACTTTT | TGGCTACAGC | TGGTACAAAG | GGGAAAGAGT | GGATGGCAAC | 300 |
| CGTCAAATTG | TAGGATATGC | AATAGGAACT | CAACAAGCTA | CCCCAGGGCC | CGCAAACAGC | 360 |
| GGTCGAGAGA | CAATATACCC | CAATGCATCC | CTGCTGATCC | AGAACGTCAC | CCAGAATGAC | 420 |
| ACAGGATTCT | ACACCCTACA | AGTCATAAAG | TCAGATCTTG | TGAATGAAGA | AGCAACTGGA | 480 |
| CAGTTCCATG | TATACCCGGA | GCTGCCCAAG | CCCTCCATCT | CCAGCAACAA | CTCCAACCCT | 540 |
| GTGGAGGACA | AGGATGCTGT | GGCCTTCACC | TGTGAACCTG | AGACTCAGGA | CACAACCTAC | 600 |
| CTGTGGTGGA | TAAACAATCA | GAGCCTCCCG | GTCAGTCCCA | GGCTGCAGCT | GTCCAATGGC | 660 |
| AACAGGACCC | TCACTCTACT | CAGTGTCACA | AGGAATGACA | CAGGACCCTA | TGAGTGTGAA | 720 |
| ATACAGAACC | CAGTGAGTGC | GAACCGCAGT | GACCCAGTCA | CCTTGAATGT | CACCTATGGC | 780 |
| CCGGACACCC | CCACCATTTC | CCCCTTCAGAC | ACCTATTACC | GTCCAGGGGC | AAACCTCAGC | 840 |
| CTCTCCTGCT | ATGCAGCCTC | TAACCCACCT | GCACAGTACT | CCTGGCTTAT | CAATGGAACA | 900 |
| TTCCAGCAAA | GCACACAAGA | GCTCTTTATC | CCTAACATCA | CTGTGAATAA | TAGTGGATCC | 960 |
| TATACCTGCC | ACGCCAATAA | CTCAGTCACT | GGCTGCAACA | GGACCACAGT | CAAGACGATC | 1020 |
| ATAGTCACTG | ATAATGCTCT | ACCACAAGAA | AATGGCCTCT | CACCTGGGCC | CATTGCTGGC | 1080 |
| ATTGTGATTG | GAGTAGTGGC | CCTGGTTGCT | CTGATAGCAG | TAGCCCTGGC | ATGTTTTCTG | 1140 |
| CATTTCGGGA | AGACCGGCAG | CTCAGGACCA | CTCCAATGAC | CCACCTAACA | AGATGAATGA | 1200 |
| AGTTACTTAT | TCTACCCTGA | ACTTTGAAGC | CCAGCAACCC | ACACAACCAA | CTTCAGCCTC | 1260 |
| CCCATCCCTA | ACAGCCACAG | AAATAATTTA | TTCAGAAGTA | AAAAAGCAGT | AATGAAACCT | 1320 |
| GAAAAAAAAA | AAAAAAAAA | | | | | 1339 |

SEQUENCE LISTING (1) GENERAL INFORMATION:
  (i) APPLICANT:   BARNETT, THOMAS R
                   ELTING, JAMES J
                   KAMARCK, MICHAEL E
                   KRETSCHMER, A W
  (ii) TITLE OF INVENTION: CDNAS CODING FOR MEMBERS OF THE
       CARCINOEMBRYONIC ANTIGEN FAMILY
  (iii) NUMBER OF SEQUENCES: 1
  (iv) CORRESPONDENCE ADDRESS:
      (A) ADDRESSEE: SPRUNG HORN KRAMER & WOODS
      (B) STREET: 1140 AVENUE OF THE AMERICAS
      (C) CITY: NEW YORK
      (D) STATE: NEW YORK
      (E) COUNTRY: U.S.A.

SEQUENCE LISTING (F) ZIP: 10036

(v) COMPUTER READABLE FORM:
    (A) MEDIUM TYPE: Floppy disk
    (B) COMPUTER: IBM PC compatible
    (C) OPERATING SYSTEM: PC-DOS/MS-DOS
    (D) SOFTWARE: PatentIn Release #1.0, Version #1.25

(vi) CURRENT APPLICATION DATA:
    (A) APPLICATION NUMBER: US 07/760,031
    (B) FILING DATE: 13-NOV-1991
    (C) CLASSIFICATION: UNASSIGNED (viii) ATTORNEY/AGENT INFORMATION:
    (A) NAME: VASTA JR, VINCENT J
    (B) REGISTRATION NUMBER: 26,655
    (C) REFERENCE/DOCKET NUMBER: MDI 242.5-VJV (ix) TELECOMMUNICATION INFORMATION:
    (A) TELEPHONE: (212) 391-0520
    (B) TELEFAX: (212) 382-0949
    (C) TELEX: 423092 NYP UI (2) INFORMATION FOR SEQ ID NO:8:
    (i) SEQUENCE CHARACTERISTICS:
        (A) LENGTH: 2010 base pairs
        (B) TYPE: nucleic acid
        (C) STRANDEDNESS: double
        (D) TOPOLOGY: linear
    (ii) MOLECULE TYPE: cDNA
    (iii) HYPOTHETICAL: NO
    (iv) ANTI-SENSE: NO
    (vi) ORIGINAL SOURCE:
        (A) ORGANISM: *HOMO SAPIENS*
    (vii) IMMEDIATE SOURCE:
        (B) CLONE: KGCEA1

(xi) SEQUENCE DESCRIPTION: SEQ ID NO:8:

```
ACAGCACAGC  TGACAGCCGT  ACTCAGGAAG  CTTCTGGATC  CTAGGCTTAT  CTCCACAGAG    60
GAGAACACAC  AAGCAGCAGA  GACCATGGGG  CCCCTCTCAG  CCCCTCCCTG  CACACACCTC   120
ATCACTTGGA  AGGGGGTCCT  GCTCACAGCA  TCACTTTTAA  ACTTCTGGAA  TCCGCCCACA   180
ACTGCCCAAG  TCACGATTGA  AGCCCAGCCA  CCCAAAGTTT  CTGAGGGGAA  GGATGTTCTT   240
CTACTTGTCC  ACAATTTGCC  CCAGAATCTT  GCTGGCTACA  TTTGGTACAA  AGGGCAAATG   300
ACATACGTCT  ACCATTACAT  TACATCATAT  GTAGTAGACG  GTCAAAGAAT  TATATATGGG   360
CCTGCATACA  GTGGAAGAGA  AAGAGTATAT  TCCAATGCAT  CCCTGCTGAT  CCAGAATGTC   420
ACGCAGGAGG  ATGCAGGATC  CTACACCTTA  CACATCATAA  AGCGACGCGA  TGGGACTGGA   480
GGAGTAACTG  GACATTTCAC  CTTCACCTTA  CACCTGGAGA  CTCCCAAGCC  CTCCATCTCC   540
AGCAGCAACT  TAAATCCCAG  GGAGGCCATG  GAGGCTGTGA  TCTTAACCTG  TGATCCTGCG   600
ACTCCAGCCG  CAAGCTACCA  GTGGTGGATG  AATGGTCAGA  GCCTCCCTAT  GACTCACAGG   660
TTGCAGCTGT  CCAAAACCAA  CAGGACCCTC  TTTATATTTG  GTGTCACAAA  GTATATTGCA   720
GGACCCTATG  AATCTGAAAT  ACGGAACCCA  GTGAGTGCCA  GCCGCAGTGA  CCCAGTCACC   780
CTGAATCTCC  TCCCAAAGCT  GTCCAAGCCC  TACATCACAA  TCAACAACTT  AAACCCCAGA   840
GAGAATAAGG  ATGTCTTAAC  CTTCACCTGT  GAACCTAAGA  GTGAGAACTA  CACCTACATT   900
TGGTGGCTAA  ATGGTCAGAG  CCTCCCTGTC  AGTCCAGGG  TAAAGCGACC  CATTGAAAAC   960
AGGATCCTCA  TTCTACCCAA  TGTCACGAGA  AATGAAACAG  GACCTTATCA  ATGTGAAATA  1020
CGGGACCGAT  ATGGTGGCAT  CCCGCAGTGAC  CCAGTCACCC  TGAATGTCCT  CTATGGTCCA  1080
GACCTCCCCA  GCATTTACCC  TTCATTCACC  TATTACCGTT  CAGGAGAAAA  CCTCTACTTT  1140
TCCTGCTTCG  GTGAGTCTAA  CCCACGGGCA  CAATATTCTT  GGACAATTAA  TGGGAAGTTT  1200
CAGCTATCAG  GACAAAAGCT  CTCTATCCCC  CAAATAACTA  CAAAGCATAG  TGGGCTCTAT  1260
GCTTGCTCTG  TTCGTAACTC  AGCCACTGGC  AAGGAAAGCT  CCAAATCCAT  CACAGTCAAA  1320
GTCTCTGACT  GGATATTACC  CTGAATTCTA  CTAGTTCCTC  CAATTCCATT  TTCTCCCATG  1380
GAATCACGAA  GAGCAAGACC  CACTCTGTTC  CAGAAGCCCT  ATAATCTGGA  GGTGGACAAC  1440
TCGATGTAAA  TTTCATGGGA  AAACCCTTGT  ACCTGACATG  TGAGCCACTC  AGAACTCACC  1500
AAAATGTTCG  ACACCATAAC  AACAGCTACT  CAAACTGTAA  ACCAGGATAA  GAAGTTGATG  1560
ACTTCACACT  GTGGACAGTT  TTTCAAAGAT  GTCATAACAA  GACTCCCCAT  CATGACAAGG  1620
CTCCACCCTC  TACTGTCTGC  TCATGCCTGC  CTCTTTCACT  TGGCAGGATA  ATGCAGTCAT  1680
TAGAATTTCA  CATGTAGTAG  CTTCTGAGGG  TAACAACACA  CTGTCAGATA  TGTCATCTCA  1740
ACCTCAAACT  TTTACGTAAC  ATCTCAGGGA  AATGTGGCTC  TCTCCATCTT  GCATACAGGG  1800
CTCCCAATAG  AAATGAACAC  AGAGATATTG  CCTGTGTGTT  TGCAGAGAAG  ATGGTTTCTA  1860
TAAAGAGTAG  GAAAGCTGAA  ATTATAGTAG  AGTCTCCTTT  AAATGCACAT  TGTGTGGATG  1920
GCTCTCACCA  TTTCCTAAGA  GATACAGTGT  AAAAACGTGA  CAGTAATACT  GATTCTAGCA  1980
GAATAAACAT  GTACCACATT  TGCAAAAAAA                                      2010
```

SEQUENCE LISTING (1) GENERAL INFORMATION:
    (i) APPLICANT:    BARNETT, THOMAS R
                          ELTING, JAMES J
                          KAMARCK, MICHAEL E
                          KRETSCHMER, A W
    (ii) TITLE OF INVENTION: CDNAS CODING FOR MEMBERS OF THE
        CARCINOEMBRYONIC ANTIGEN FAMILY
    (iii) NUMBER OF SEQUENCES: 1
    (iv) CORRESPONDENCE ADDRESS:

SEQUENCE LISTING (A) ADDRESSEE: SPRUNG HORN KRAMER & WOODS
(B) STREET: 1140 AVENUE OF THE AMERICAS
(C) CITY: NEW YORK
(D) STATE: NEW YORK
(E) COUNTRY: U.S.A.
(F) ZIP: 10036

(v) COMPUTER READABLE FORM:
   (A) MEDIUM TYPE: Floppy disk
   (B) COMPUTER: IBM PC compatible
   (C) OPERATING SYSTEM: PC-DOS/MS-DOS
   (D) SOFTWARE: PatentIn Release #1.0, Version #1.25

(vi) CURRENT APPLICATION DATA:
   (A) APPLICATION NUMBER: US 07/760,031
   (B) FILING DATE: 13-NOV-1991
   (C) CLASSIFICATION: UNASSIGNED (viii) ATTORNEY/AGENT INFORMATION:
   (A) NAME: VASTA JR, VINCENT J
   (B) REGISTRATION NUMBER: 26,655
   (C) REFERENCE/DOCKET NUMBER: MDI 242.5-VJV (ix) TELECOMMUNICATION INFORMATION:
   (A) TELEPHONE: (212) 391-0520
   (B) TELEFAX: (212) 382-0949
   (C) TELEX: 423092 NYP UI (2) INFORMATION FOR SEQ ID NO:9:
   (i) SEQUENCE CHARACTERISTICS:
     (A) LENGTH: 1591 base pairs
     (B) TYPE: nucleic acid
     (C) STRANDEDNESS: double
     (D) TOPOLOGY: linear
   (ii) MOLECULE TYPE: cDNA
   (iii) HYPOTHETICAL: NO
   (iv) ANTI-SENSE: NO
   (vi) ORIGINAL SOURCE:
     (A) ORGANISM: *homo sapiens*
   (vii) IMMEDIATE SOURCE:
     (B) CLONE: KGCEA2

(xi) SEQUENCE DESCRIPTION: SEQ ID NO:9:

| | | | | | | |
|---|---|---|---|---|---|---|
| GGGTGGATCC | TAGGCTCATC | TCCATAGGGG | AGAACACACA | TACAGCAGAG | ACCATGGGAC | 60 |
| CCCTCTCAGC | CCCTCCCTGC | ACTCAGCACA | TCACCTGGAA | GGGGCTCCTG | CTCACAGCAT | 120 |
| CACTTTTAAA | CTTCTGGAAC | CTGCCCACCA | CTGCCCAAGT | AATAATTGAA | GCCCAGCCAC | 180 |
| CCAAAGTTTC | TGAGGGGAAG | GATGTTCTTC | TACTTGTCCA | CAATTTGCCC | CAGAATCTTA | 240 |
| CTGGCTACAT | CTGGTACAAA | GGGCAAATGA | CGGACCTCTA | CCATTACATT | ACATCATATG | 300 |
| TAGTAGACGG | TCAAATTATA | TATGGGCCTG | CCTACAGTGG | ACGAGAAACA | GTATATTCCA | 360 |
| ATGCATCCCT | GCTGATCCAG | AATGTCACAC | AGGAGGATGC | AGGATCCTAC | ACCTTACACA | 420 |
| TCATAAAGCG | AGGCGATGGG | ACTGGAGGAG | TAACTGGATA | TTTCACTGTC | ACCTTATACT | 480 |
| CGGAGACTCC | CAAGCGCTCC | ATCTCCAGCA | GCAACTTAAA | CCCCAGGGAG | GTCATGGAGG | 540 |
| CTGTGCGCTT | AATCTGTGAT | CCTGAGACTC | CGGATGCAAG | CTACCTGTGG | TTGCTGAATG | 600 |
| GTCAGAACCT | CCCTATGACT | CACAGGTTGC | AGCTGTCCAA | AACCAACAGG | ACCCTCTATC | 660 |
| TATTTGGTGT | CACAAAGTAT | ATTGCAGGGC | CCTATGAATG | TGAAATACGG | AGGGGAGTGA | 720 |
| GTGCCAGCCG | CAGTGACCCA | GTCACCCTGA | ATCTCCTCCC | GAAGCTGCCC | ATGCCTTACA | 780 |
| TCACCATCAA | CAACTTAAAC | CCCAGGGAGA | AGAAGGATGT | GTTAGCCTTC | ACCTGTGAAC | 840 |
| CTAAGAGTCG | GAACTACACC | TACATTTGGT | GGCTAAATGG | TCAGAGCCTC | CCGGTCAGTC | 900 |
| CGAGGGTAAA | GCGACCCATT | GAAAACAGGA | TACTCATTCT | ACCCAGTGTC | ACGAGAAATG | 960 |
| AAACAGGACC | CTATCAATGT | GAAATACGGG | ACCGATATGG | TGGCATCCGC | AGTAACCCAG | 1020 |
| TCACCCTGAA | TGTCCTCTAT | GGTCCAGACC | TCCCCAGAAT | TTACCCTTAC | TTCACCTATT | 1080 |
| ACCGTTCAGG | AGAAAACCTC | GACTTGTCCT | GCTTTGCGGA | CTCTAACCCA | CCGGCAGAGT | 1140 |
| ATTTTTGGAC | AATTAATGGG | AAGTTTCAGC | TATCAGGACA | AAAGCTCTTT | ATCCCCCAAA | 1200 |
| TTACTACAAA | TCATAGCGGG | CTCTATGCTT | GCTCTGTTCG | TAACTCAGCC | ACTGGCAAGG | 1260 |
| AAATCTCCAA | ATCCATGATA | GTCAAAGTCT | CTGGTCCCTG | CCATGGAAAC | CAGACAGAGT | 1320 |
| CTCATTAATG | GCTGCCACAA | TAGAGACACT | GAGAAAAAGA | ACAGGTTGAT | ACCTTCATGA | 1380 |
| AATTCAAGAC | AAAGAAGAAA | AAGGCTCAAT | GTTATTGGAC | TAAATAATCA | AAAGGATAAT | 1440 |
| GTTTTCATAA | TTTTTATTGG | AAAATGTGCT | GATTCTTGGA | ATGTTTTATT | CTCCAGATTT | 1500 |
| ATGAACTTTT | TTTCTTCAGC | AATTGGTAAA | GTATACTTTT | GTAAACAAAA | ATTGAAACAT | 1560 |
| TTGCTTTTGC | TCTCTATCTG | AGTGCCCCCC | C | | | 1591 |

SEQUENCE LISTING (1) GENERAL INFORMATION:
   (i) APPLICANT:   BARNETT, THOMAS R
                       ELTING, JAMES J
                       KAMARCK, MICHAEL E
                       KRETSCHMER, A W
   (ii) TITLE OF INVENTION: CDNAS CODING FOR MEMBERS OF THE CARCINOEMBRYONIC ANTIGEN FAMILY
   (iii) NUMBER OF SEQUENCES: 1
   (iv) CORRESPONDENCE ADDRESS:
     (A) ADDRESSEE: SPRUNG HORN KRAMER & WOODS
     (B) STREET: 1140 AVENUE OF THE AMERICAS

SEQUENCE LISTING

-continued (C) CITY: NEW YORK
      (D) STATE: NEW YORK
      (E) COUNTRY: U.S.A.
      (F) ZIP: 10036
  (v) COMPUTER READABLE FORM:
      (A) MEDIUM TYPE: Floppy disk
      (B) COMPUTER: IBM PC compatible
      (C) OPERATING SYSTEM: PC-DOS/MS-DOS
      (D) SOFTWARE: PatentIn Release #1.0, Version #1.25
  (vi) CURRENT APPLICATION DATA:
      (A) APPLICATION NUMBER: US 07/760,031
      (B) FILING DATE: 13-NOV-1991
      (C) CLASSIFICATION: UNASSIGNED
  (viii) ATTORNEY/AGENT INFORMATION:
      (A) NAME: VASTA JR, VINCENT J
      (B) REGISTRATION NUMBER: 26,655
      (C) REFERENCE/DOCKET NUMBER: MDI 242.5-VJV
  (ix) TELECOMMUNICATION INFORMATION:
      (A) TELEPHONE: (212) 391-0520
      (B) TELEFAX: (212) 382-0949
      (C) TELEX: 423092 NYP UI
(2) INFORMATION FOR SEQ ID NO:10:
  (i) SEQUENCE CHARACTERISTICS:
      (A) LENGTH: 702 amino acids
      (B) TYPE: amino acid
      (D) TOPOLOGY: linear
  (ii) MOLECULE TYPE: peptide
  (iii) HYPOTHETICAL: YES
  (iv) ANTI-SENSE: NO
  (vii) IMMEDIATE SOURCE:
      (B) CLONE: TRANSLATED POLYPEPTIDE FROM CEA-(b) cDNA
  (xi) SEQUENCE DESCRIPTION: SEQ ID NO:10:

| | | | | | | | | | | | | | | |
|---|---|---|---|---|---|---|---|---|---|---|---|---|---|---|
| Met 1 | Glu | Ser | Pro | Ser 5 | Ala | Pro | Pro | His | Arg 10 | Trp | Cys | Ile | Pro | Trp 15 | Gln |
| Arg | Leu | Leu | Leu 20 | Thr | Ala | Ser | Leu | Leu 25 | Thr | Phe | Trp | Asn | Pro 30 | Pro | Thr |
| Thr | Ala | Lys 35 | Leu | Thr | Ile | Glu | Ser 40 | Thr | Pro | Phe | Asn | Val 45 | Ala | Glu | Gly |
| Lys | Glu 50 | Val | Leu | Leu | Leu | Val 55 | His | Asn | Leu | Pro | Gln 60 | His | Leu | Phe | Gly |
| Tyr 65 | Ser | Trp | Tyr | Lys | Gly 70 | Glu | Arg | Val | Asp | Gly 75 | Asn | Arg | Gln | Ile | Ile 80 |
| Gly | Tyr | Val | Ile | Gly 85 | Thr | Gln | Gln | Ala | Thr | Pro 90 | Gly | Pro | Ala | Tyr 95 | Ser |
| Gly | Arg | Glu | Ile 100 | Ile | Tyr | Pro | Asn | Ala 105 | Ser | Leu | Leu | Ile | Gln 110 | Asn | Ile |
| Ile | Gln | Asn 115 | Asp | Thr | Gly | Phe | Tyr 120 | Thr | Leu | His | Val | Ile 125 | Lys | Ser | Asp |
| Leu | Val 130 | Asn | Glu | Glu | Ala | Thr 135 | Gly | Gln | Phe | Arg | Val 140 | Tyr | Pro | Glu | Leu |
| Pro 145 | Lys | Pro | Ser | Ile | Ser 150 | Ser | Asn | Asn | Ser | Lys 155 | Pro | Val | Glu | Asp | Lys 160 |
| Asp | Ala | Val | Ala | Phe 165 | Thr | Cys | Glu | Pro | Glu 170 | Thr | Gln | Asp | Ala | Thr 175 | Tyr |
| Leu | Trp | Trp | Val 180 | Asn | Asn | Gln | Ser | Leu 185 | Pro | Val | Ser | Pro | Arg 190 | Leu | Gln |
| Leu | Ser | Asn 195 | Gly | Asn | Arg | Thr | Leu 200 | Thr | Leu | Phe | Asn | Val 205 | Thr | Arg | Asn |
| Asp | Thr 210 | Ala | Ser | Tyr | Lys | Cys 215 | Glu | Thr | Gln | Asn | Pro 220 | Val | Ser | Ala | Arg |
| Arg 225 | Ser | Asp | Ser | Val | Ile 230 | Leu | Asn | Val | Leu | Tyr 235 | Gly | Pro | Asp | Ala | Pro 240 |
| Thr | Ile | Ser | Pro | Leu 245 | Asn | Thr | Ser | Tyr | Arg 250 | Ser | Gly | Glu | Asn | Leu 255 | Asn |
| Leu | Ser | Cys | His | Ala | Ala | Ser | Asn | Pro | Pro | Ala | Gln | Tyr | Ser | Trp | Phe |

SEQUENCE LISTING

|   |   |   | 260 |   |   |   | 265 |   |   |   | 270 |   |   |   |
|---|---|---|---|---|---|---|---|---|---|---|---|---|---|---|
| Val | Asn | Gly 275 | Thr | Phe | Gln | Gln | Ser 280 | Thr | Gln | Glu | Leu | Phe 285 | Ile | Pro | Asn |
| Ile | Thr 290 | Val | Asn | Asn | Ser | Gly 295 | Ser | Tyr | Thr | Cys | Gln 300 | Ala | His | Asn | Ser |
| Asp 305 | Thr | Gly | Leu | Asn | Arg 310 | Thr | Thr | Val | Thr | Thr 315 | Ile | Thr | Val | Tyr | Ala 320 |
| Glu | Pro | Pro | Lys | Pro 325 | Phe | Ile | Thr | Ser | Asn 330 | Asn | Ser | Asn | Pro | Val 335 | Glu |
| Asp | Glu | Asp | Ala 340 | Val | Ala | Leu | Thr | Cys 345 | Glu | Pro | Glu | Ile | Gln 350 | Asn | Thr |
| Thr | Tyr | Leu 355 | Trp | Trp | Val | Asn | Asn 360 | Gln | Ser | Leu | Pro | Val 365 | Ser | Pro | Arg |
| Leu | Gln 370 | Leu | Ser | Asn | Asp | Asn 375 | Arg | Thr | Leu | Thr | Leu 380 | Leu | Ser | Val | Thr |
| Arg 385 | Asn | Asp | Val | Gly | Pro 390 | Tyr | Glu | Cys | Gly | Ile 395 | Gln | Asn | Glu | Leu | Ser 400 |
| Val | Asp | His | Ser | Asp 405 | Pro | Val | Ile | Leu | Asn 410 | Val | Leu | Tyr | Gly | Pro 415 | Asp |
| Asp | Pro | Thr | Ile 420 | Ser | Pro | Ser | Tyr | Thr 425 | Tyr | Tyr | Arg | Pro | Gly 430 | Val | Asn |
| Leu | Ser | Leu 435 | Ser | Cys | His | Ala | Ala 440 | Ser | Asn | Pro | Pro | Ala 445 | Gln | Tyr | Ser |
| Trp | Leu 450 | Ile | Asp | Gly | Asn | Ile 455 | Gln | Gln | His | Thr | Gln 460 | Glu | Leu | Phe | Ile |
| Ser 465 | Asn | Ile | Thr | Glu | Lys 470 | Asn | Ser | Gly | Leu | Tyr 475 | Thr | Cys | Gln | Ala | Asn 480 |
| Asn | Ser | Ala | Ser | Gly 485 | His | Ser | Arg | Thr | Thr 490 | Val | Lys | Thr | Ile | Thr 495 | Val |
| Ser | Ala | Glu | Leu 500 | Pro | Lys | Pro | Ser | Ile 505 | Ser | Ser | Asn | Asn | Ser 510 | Lys | Pro |
| Val | Glu | Asp 515 | Lys | Asp | Ala | Val | Ala 520 | Phe | Thr | Cys | Glu | Pro 525 | Glu | Ala | Gln |
| Asn | Thr 530 | Thr | Tyr | Leu | Trp | Trp 535 | Val | Asn | Gly | Gln | Ser 540 | Leu | Pro | Val | Ser |
| Pro 545 | Arg | Leu | Gln | Leu | Ser 550 | Asn | Gly | Asn | Arg | Thr 555 | Leu | Thr | Leu | Phe | Asn 560 |
| Val | Thr | Arg | Asn | Asp 565 | Ala | Arg | Ala | Tyr | Val 570 | Cys | Gly | Ile | Gln | Asn 575 | Ser |
| Val | Ser | Ala | Asn 580 | Arg | Ser | Asp | Pro | Val 585 | Thr | Leu | Asp | Val | Leu 590 | Tyr | Gly |
| Pro | Asp | Thr 595 | Pro | Ile | Ile | Ser | Pro 600 | Pro | Asp | Ser | Ser | Tyr 605 | Leu | Ser | Gly |
| Ala | Asn 610 | Leu | Asn | Leu | Ser | Cys 615 | His | Ser | Ala | Ser | Asn 620 | Pro | Ser | Pro | Gln |
| Tyr 625 | Ser | Trp | Arg | Ile | Asn 630 | Gly | Ile | Pro | Gln | Gln 635 | His | Thr | Gln | Val | Leu 640 |
| Phe | Ile | Ala | Lys | Ile 645 | Thr | Pro | Asn | Asn | Asn 650 | Gly | Thr | Tyr | Ala | Cys 655 | Phe |
| Val | Ser | Asn | Leu 660 | Ala | Thr | Gly | Arg | Asn 665 | Asn | Ser | Ile | Val | Lys 670 | Ser | Ile |
| Thr | Val | Ser 675 | Ala | Ser | Gly | Thr | Ser 680 | Pro | Gly | Leu | Ser | Ala 685 | Gly | Ala | Thr |
| Val | Gly | Ile | Met | Ile | Gly | Val | Leu | Val | Gly | Val | Ala | Leu | Ile |

SEQUENCE LISTING

| 690 | 695 | 700 |
|---|---|---|

SEQUENCE LISTING (1) GENERAL INFORMATION
    (i) APPLICANT: BARNETT, THOMAS R
                            ELTING, JAMES J
                            KAMARCK, MICHAEL E
                            KRETSCHMER, A W
    (ii) TITLE OF INVENTION: CDNAS CODING FOR MEMBERS OF THE
         CARCINOEMBRYONIC ANTIGEN FAMILY
    (iii) NUMBER OF SEQUENCES: 1
    (iv) CORRESPONDENCE ADDRESS:
        (A) ADDRESSEE: SPRUNG HORN KRAMER & WOODS
        (B) STREET: 1140 AVENUE OF THE AMERICAS
        (C) CITY: NEW YORK
        (D) STATE: NEW YORK
        (E) COUNTRY: U.S.A.
        (F) ZIP: 10036
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25
    (vi) CURRENT APPLICATION DATA:
        (A) APPLICATION NUMBER: US 07/760,031
        (B) FILING DATE: 13-NOV-1991
        (C) CLASSIFICATION: UNASSIGNED
    (viii) ATTORNEY/AGENT INFORMATION:
        (A) NAME: VASTA JR, VINCENT J
        (B) REGISTRATION NUMBER: 26,655
        (C) REFERENCE/DOCKET NUMBER: MDI 242.5-VJV
    (ix) TELECOMMUNICATION INFORMATION:
        (A) TELEPHONE: (212) 391-0520
        (B) TELEFAX: (212) 382-0949
        (C) TELEX: 423092 NYP UI
(2) INFORMATION FOR SEQ ID NO:11:
    (i) SEQUENCE CHARACTERISTICS:
        (A) LENGTH: 526 amino acids
        (B) TYPE: amino acid
        (D) TOPOLOGY: linear
    (ii) MOLECULE TYPE: peptide
    (iii) HYPOTHETICAL: YES
    (iv) ORIGINAL SOURCE:
        (A) ORGANISM: *HOMO SAPIENS*
    (vii) IMMEDIATE SOURCE:
        (B) CLONE: TRANSLATED POLYPEPTIDE FROM CEA-(c) cDNA
    (xi) SEQUENCE DESCRIPTION: SEQ ID NO:11:

| Met 1 | Gly | His | Leu | Ser 5 | Ala | Pro | Leu | His | Arg 10 | Val | Arg | Val | Pro | Trp 15 | Gln |
|---|---|---|---|---|---|---|---|---|---|---|---|---|---|---|---|
| Gly | Leu | Leu | Leu 20 | Thr | Ala | Ser | Leu | Leu 25 | Thr | Phe | Trp | Asn | Pro 30 | Pro | Thr |
| Thr | Ala | Gln 35 | Leu | Thr | Thr | Glu | Ser 40 | Met | Pro | Phe | Asn | Val 45 | Ala | Glu | Gly |
| Lys | Glu 50 | Val | Leu | Leu | Leu | Val 55 | His | Asn | Leu | Pro | Gln 50 | Gln | Leu | Phe | Gly |
| Tyr 65 | Ser | Trp | Tyr | Lys | Gly 70 | Glu | Arg | Val | Asp | Gly 75 | Asn | Arg | Gln | Ile | Val 80 |
| Gly | Tyr | Ala | Ile | Gly 85 | Thr | Gln | Gln | Ala | Thr 90 | Pro | Gly | Pro | Ala | Asn 95 | Ser |
| Gly | Arg | Glu | Thr 100 | Ile | Tyr | Pro | Asn | Ala 105 | Ser | Leu | Leu | Ile | Gln 110 | Asn | Val |
| Thr | Gln | Asn 115 | Asp | Thr | Gly | Phe | Tyr 120 | Thr | Leu | Gln | Val | Ile 125 | Lys | Ser | Asp |
| Leu | Val 130 | Asn | Glu | Glu | Ala | Thr 135 | Gly | Gln | Phe | His | Val 140 | Tyr | Pro | Glu | Leu |
| Pro 145 | Lys | Pro | Ser | Ile | Ser 150 | Ser | Asn | Asn | Ser | Asn 155 | Pro | Val | Glu | Asp | Lys 160 |

-continued

SEQUENCE LISTING

| Asp | Ala | Val | Ala | Phe 165 | Thr | Cys | Glu | Pro 170 | Glu | Thr | Gln | Asp | Thr 175 | Thr | Tyr |
| Leu | Trp | Trp | Ile 180 | Asn | Asn | Gln | Ser | Leu 185 | Pro | Val | Ser | Pro | Arg 190 | Leu | Gln |
| Leu | Ser | Asn 195 | Gly | Asn | Arg | Thr | Leu 200 | Thr | Leu | Leu | Ser | Val 205 | Thr | Arg | Asn |
| Asp | Thr 210 | Gly | Pro | Tyr | Glu | Cys 215 | Glu | Ile | Gln | Asn | Pro 220 | Val | Ser | Ala | Asn |
| Arg 225 | Ser | Asp | Pro | Val | Thr 230 | Leu | Asn | Val | Thr | Tyr 235 | Gly | Pro | Asp | Thr | Pro 240 |
| Thr | Ile | Ser | Pro | Ser 245 | Asp | Thr | Tyr | Tyr | Arg 250 | Pro | Gly | Ala | Asn | Leu 255 | Ser |
| Leu | Ser | Cys | Tyr 260 | Ala | Ala | Ser | Asn | Pro 265 | Pro | Ala | Gln | Tyr | Ser 270 | Trp | Leu |
| Ile | Asn | Gly 275 | Thr | Phe | Gln | Gln | Ser 280 | Thr | Gln | Glu | Leu | Phe 285 | Ile | Pro | Asn |
| Ile | Thr 290 | Val | Asn | Asn | Ser | Gly 295 | Ser | Tyr | Thr | Cys | His 300 | Ala | Asn | Asn | Ser |
| Val 305 | Thr | Gly | Cys | Asn | Arg 310 | Thr | Thr | Val | Lys | Thr 315 | Ile | Ile | Val | Thr | Glu 320 |
| Leu | Ser | Pro | Val | Val 325 | Ala | Lys | Pro | Gln | Ile 330 | Lys | Ala | Ser | Lys | Thr 335 | Thr |
| Val | Thr | Gly | Asp 340 | Lys | Asp | Ser | Val | Asn 345 | Leu | Thr | Cys | Ser | Thr 350 | Asn | Asp |
| Thr | Gly | Ile 355 | Ser | Ile | Arg | Trp | Phe 360 | Phe | Lys | Asn | Gln | Ser 365 | Leu | Pro | Ser |
| Ser | Glu 370 | Arg | Met | Lys | Leu | Ser 375 | Gln | Gly | Asn | Thr | Thr 380 | Leu | Ser | Ile | Asn |
| Pro 385 | Val | Lys | Arg | Glu | Asp 390 | Ala | Gly | Thr | Tyr | Trp 395 | Cys | Glu | Val | Phe | Asn 400 |
| Pro | Ile | Ser | Lys | Asn 405 | Gln | Ser | Asp | Pro | Ile 410 | Met | Leu | Asn | Val | Asn 415 | Tyr |
| Asn | Ala | Leu | Pro 420 | Gln | Glu | Asn | Gly | Leu 425 | Ser | Pro | Gly | Ala | Ile 430 | Ala | Gly |
| Ile | Val | Ile 435 | Gly | Val | Val | Ala | Leu 440 | Val | Ala | Leu | Ile | Ala 445 | Val | Ala | Leu |
| Ala | Cys 450 | Phe | Leu | His | Phe | Gly 455 | Lys | Thr | Gly | Arg | Ala 460 | Ser | Asp | Gln | Arg |
| Asp 465 | Leu | Thr | Glu | His | Lys 470 | Pro | Ser | Val | Ser | Asn 475 | His | Thr | Gln | Asp | His 480 |
| Ser | Asn | Asp | Pro | Pro 485 | Asn | Lys | Met | Asn | Glu 490 | Val | Thr | Tyr | Ser | Thr 495 | Leu |
| Asn | Phe | Glu | Ala 500 | Gln | Gln | Pro | Thr | Gln 505 | Pro | Thr | Ser | Ala | Ser 510 | Pro | Ser |
| Leu | Thr | Ala 515 | Thr | Glu | Ile | Ile | Tyr 520 | Ser | Glu | Val | Lys | Lys 525 | Gln | | |

SEQUENCE LISTING (1) GENERAL INFORMATION:
    (i) APPLICANT: BARNETT, THOMAS R
                              ELTING, JAMES J
                              KAMARCK, MICHAEL E
                              KRETSCHMER, A W
    (ii) TITLE OF INVENTION: CDNAS CODING FOR MEMBERS OF THE CARCINOEMBRYONIC ANTIGEN FAMILY

SEQUENCE LISTING (iii) NUMBER OF SEQUENCES: 1
(iv) CORRESPONDENCE ADDRESS:
    (A) ADDRESSEE: SPRUNG HORN KRAMER & WOODS
    (B) STREET: 1140 AVENUE OF THE AMERICAS
    (C) CITY: NEW YORK
    (D) STATE: NEW YORK
    (E) COUNTRY: U.S.A.
    (F) ZIP: 10036
(v) COMPUTER READABLE FORM:
    (A) MEDIUM TYPE: Floppy disk
    (B) COMPUTER: IBM PC compatible
    (C) OPERATING SYSTEM: PC-DOS/MS-DOS
    (D) SOFTWARE: PatentIn Release #1.0, Version #1.25
(vi) CURRENT APPLICATION DATA:
    (A) APPLICATION NUMBER: US 07/760,031
    (B) FILING DATE: 13-NOV-1991
    (C) CLASSIFICATION: UNASSIGNED
(viii) ATTORNEY/AGENT INFORMATION:
    (A) NAME: VASTA JR, VINCENT J
    (B) REGISTRATION NUMBER: 26,655
    (C) REFERENCE/DOCKET NUMBER: MDI 242.5-VJV
(ix) TELECOMMUNICATION INFORMATION:
    (A) TELEPHONE: (212) 391-0520
    (B) TELEFAX: (212) 382-0949
    (C) TELEX: 423092 NYP UI (2) INFORMATION FOR SEQ ID NO:12:
    (i) SEQUENCE CHARACTERISTICS:
        (A) LENGTH: 344 amino acids
        (B) TYPE: amino acid
        (D) TOPOLOGY: linear
    (ii) MOLECULE TYPE: peptide
    (iii) HYPOTHETICAL: YES
    (vi) ORIGINAL SOURCE:
        (A) ORGANISM: *HOMO SAPIENS*
    (vii) IMMEDIATE SOURCE:
        (B) CLONE: TRANSLATED POLYPEPTIDE FROM CEA-(d) cDNA
    (xi) SEQUENCE DESCRIPTION: SEQ ID NO:12:

| Met 1 | Gly | Pro | Pro | Ser 5 | Ala | Pro | Pro | Cys | Arg 10 | Leu | His | Val | Pro | Trp 15 | Lys |
|---|---|---|---|---|---|---|---|---|---|---|---|---|---|---|---|
| Glu | Val | Leu | Leu 20 | Thr | Ala | Ser | Leu | Leu 25 | Thr | Phe | Trp | Asn | Pro 30 | Pro | Thr |
| Thr | Ala | Lys 35 | Leu | Thr | Ile | Glu | Ser 40 | Thr | Pro | Phe | Asn | Val 45 | Ala | Glu | Gly |
| Lys | Glu 50 | Val | Leu | Leu | Leu | Ala 55 | His | Asn | Leu | Pro | Gln 60 | Asn | Arg | Ile | Gly |
| Tyr 65 | Ser | Trp | Tyr | Lys | Gly 70 | Glu | Arg | Val | Asp | Gly 75 | Asn | Ser | Leu | Ile | Val 80 |
| Gly | Tyr | Val | Ile | Gly 85 | Thr | Gln | Gln | Ala | Thr 90 | Pro | Gly | Pro | Ala | Tyr 95 | Ser |
| Gly | Arg | Glu | Thr 100 | Ile | Tyr | Pro | Asn | Ala 105 | Ser | Leu | Leu | Ile | Gln 110 | Asn | Val |
| Thr | Gln | Asn 115 | Asp | Thr | Gly | Phe | Tyr 120 | Thr | Leu | Gln | Val | Ile 125 | Lys | Ser | Asp |
| Leu | Val 130 | Asn | Glu | Glu | Ala | Thr 135 | Gly | Gln | Phe | His | Val 140 | Tyr | Pro | Glu | Leu |
| Pro 145 | Lys | Pro | Ser | Ile | Ser 150 | Ser | Asn | Asn | Ser | Asn 155 | Pro | Val | Glu | Asp | Lys 160 |
| Asp | Ala | Val | Ala | Phe 165 | Thr | Cys | Glu | Pro | Glu 170 | Val | Gln | Asn | Thr | Thr 175 | Tyr |
| Leu | Trp | Trp | Val 180 | Asn | Gly | Gln | Ser | Leu 185 | Pro | Val | Ser | Pro | Arg 190 | Leu | Gln |
| Leu | Ser | Asn 195 | Gly | Asn | Arg | Thr | Leu 200 | Thr | Leu | Leu | Ser | Val 205 | Lys | Arg | Asn |
| Asp | Ala 210 | Gly | Ser | Tyr | Glu | Cys 215 | Glu | Ile | Gln | Asn | Pro 220 | Ala | Ser | Ala | Asn |
| Arg 225 | Ser | Asp | Pro | Val | Thr 230 | Leu | Asn | Val | Leu | Tyr 235 | Gly | Pro | Asp | Gly | Pro 240 |

SEQUENCE LISTING

| Thr | Ile | Ser | Pro | Ser 245 | Lys | Ala | Asn | Tyr | Arg 250 | Pro | Gly | Glu | Asn | Leu 255 | Asn |
|---|---|---|---|---|---|---|---|---|---|---|---|---|---|---|---|
| Leu | Ser | Cys | His 260 | Ala | Ala | Ser | Asn | Pro 265 | Pro | Ala | Gln | Tyr | Ser 270 | Trp | Phe |
| Ile | Asn | Gly 275 | Thr | Phe | Gln | Gln | Ser 280 | Thr | Gln | Glu | Leu | Phe 285 | Ile | Pro | Asn |
| Ile | Thr 290 | Val | Asn | Asn | Ser | Gly 295 | Ser | Tyr | Met | Cys | Gln 300 | Ala | His | Asn | Ser |
| Ala 305 | Thr | Gly | Leu | Asn | Arg 310 | Thr | Thr | Val | Thr | Met 315 | Ile | Thr | Val | Ser | Gly 320 |
| Ser | Ala | Pro | Val | Leu 325 | Ser | Ala | Val | Ala | Thr 330 | Val | Gly | Ile | Thr | Ile 335 | Gly |
| Val | Leu | Ala | Arg 340 | Val | Ala | Leu | Ile | | | | | | | | |

SEQUENCE LISTING (1) GENERAL INFORMATION:
    (i) APPLICANT:    BARNETT, THOMAS R
                            ELTING, JAMES J
                            KAMARCK, MICHAEL E
                            KRETSCHMER, A W
    (ii) TITLE OF INVENTION: CDNAS CODING FOR MEMBERS OF THE
         CARCINOEMBRYONIC ANTIGEN FAMILY
    (iii) NUMBER OF SEQUENCES: 1
    (iv) CORRESPONDENCE ADDRESS:
         (A) ADDRESSEE: SPRUNG HORN KRAMER & WOODS
         (B) STREET: 1140 AVENUE OF THE AMERICAS
         (C) CITY: NEW YORK
         (D) STATE: NEW YORK
         (E) COUNTRY: U.S.A.
         (F) ZIP: 10036
    (v) COMPUTER READABLE FORM:
         (A) MEDIUM TYPE: Floppy disk
         (B) COMPUTER: IBM PC compatible
         (C) OPERATING SYSTEM: PC-DOS/MS-DOS
         (D) SOFTWARE: PatentIn Release #1.0, Version #1.25
    (vi) CURRENT APPLICATION DATA:
         (A) APPLICATION NUMBER: US 07/760,031
         (B) FILING DATE: 13-NOV-1991
         (C) CLASSIFICATION: UNASSIGNED
    (viii) ATTORNEY/AGENT INFORMATION:
         (A) NAME: VASTA JR. VINCENT J
         (B) REGISTRATION NUMBER: 26,655
         (C) REFERENCE/DOCKET NUMBER: MDI 242.5-VJV
    (ix) TELECOMMUNICATION INFORMATION:
         (A) TELEPHONE: (212) 391-0520
         (B) TELEFAX: (212) 382-0949
         (C) TELEX: 423092 NYP UI
(2) INFORMATION FOR SEQ ID NO:13:
    (i) SEQUENCE CHARACTERISTICS:
         (A) LENGTH: 430 amino acids
         (B) TYPE: amino acid
         (D) TOPOLOGY: linear
    (ii) MOLECULE TYPE: peptide
    (iii) HYPOTHETICAL: YES
    (vi) ORIGINAL SOURCE:
         (A) ORGANISM: *HOMO SAPIENS*
    (vii) IMMEDIATE SOURCE:
         (B) CLONE: TRANSLATED POLYPEPTIDE FROM CEA-(e) cDNA
    (xi) SEQUENCE DESCRIPTION: SEQ ID NO:13:

| Met 1 | Gly | His | Leu | Ser 5 | Ala | Pro | Leu | His | Arg 10 | Val | Arg | Val | Pro | Trp 15 | Gln |
|---|---|---|---|---|---|---|---|---|---|---|---|---|---|---|---|
| Gly | Leu | Leu | Leu 20 | Thr | Ala | Ser | Leu | Leu 25 | Thr | Phe | Trp | Asn | Pro 30 | Pro | Thr |
| Thr | Ala | Gln 35 | Leu | Thr | Thr | Glu | Ser 40 | Met | Pro | Phe | Asn | Val 45 | Ala | Glu | Gly |
| Lys | Glu 50 | Val | Leu | Leu | Leu | Val 55 | His | Asn | Leu | Pro | Gln 60 | Gln | Leu | Phe | Gly |

-continued

| | | | | | | | | | | | | | | | |
|---|---|---|---|---|---|---|---|---|---|---|---|---|---|---|---|
| Tyr 65 | Ser | Trp | Tyr | Lys | Gly 70 | Glu | Arg | Val | Asp | Gly 75 | Asn | Arg | Gln | Ile | Val 80 |
| Gly | Tyr | Ala | Ile | Gly 85 | Thr | Gln | Gln | Ala | Thr 90 | Pro | Gly | Pro | Ala | Asn 95 | Ser |
| Gly | Arg | Glu | Thr 100 | Ile | Tyr | Pro | Asn | Ala 105 | Ser | Leu | Leu | Ile | Gln 110 | Asn | Val |
| Thr | Gln | Asn 115 | Asp | Thr | Gly | Phe | Tyr 120 | Thr | Leu | Gln | Val | Ile 125 | Lys | Ser | Asp |
| Leu | Val 130 | Asn | Glu | Glu | Ala | Thr 135 | Gly | Gln | Phe | His | Val 140 | Tyr | Pro | Glu | Leu |
| Pro 145 | Lys | Pro | Ser | Ile | Ser 150 | Ser | Asn | Asn | Ser | Asn 155 | Pro | Val | Gly | Asp | Lys 160 |
| Asp | Ala | Val | Ala | Phe 165 | Thr | Cys | Glu | Pro | Glu 170 | Thr | Gln | Asp | Thr | Thr 175 | Tyr |
| Leu | Trp | Trp | Ile 180 | Asn | Asn | Gln | Ser | Leu 185 | Pro | Val | Ser | Pro | Arg 190 | Leu | Gln |
| Leu | Ser | Asn 195 | Gly | Asn | Arg | Thr | Leu 200 | Thr | Leu | Leu | Ser | Val 205 | Thr | Arg | Asn |
| Asp | Thr 210 | Gly | Pro | Tyr | Glu | Cys 215 | Glu | Ile | Gln | Asn | Pro 220 | Val | Ser | Ala | Asn |
| Arg 225 | Ser | Asp | Pro | Val | Thr 230 | Leu | Asn | Val | Thr | Tyr 235 | Gly | Pro | Asp | Thr | Pro 240 |
| Thr | Ile | Ser | Pro | Ser 245 | Asp | Thr | Tyr | Tyr | Arg 250 | Pro | Gly | Ala | Asn | Leu 255 | Ser |
| Leu | Ser | Cys | Tyr 260 | Ala | Ala | Ser | Asn | Pro 265 | Pro | Ala | Gln | Tyr | Ser 270 | Trp | Leu |
| Ile | Asn | Gly 275 | Thr | Phe | Gln | Gln | Ser 280 | Thr | Gln | Glu | Leu | Phe 285 | Ile | Pro | Asn |
| Ile | Thr 290 | Val | Asn | Asn | Ser | Gly 295 | Ser | Tyr | Thr | Cys | His 300 | Ala | Asn | Asn | Ser |
| Val 305 | Thr | Gly | Cys | Asn | Arg 310 | Thr | Thr | Val | Lys | Thr 315 | Ile | Ile | Val | Thr | Asp 320 |
| Asn | Ala | Leu | Pro | Gln 325 | Glu | Asn | Gly | Leu | Ser 330 | Pro | Gly | Ala | Ile | Ala 335 | Gly |
| Ile | Val | Ile | Gly 340 | Val | Val | Ala | Leu | Val 345 | Ala | Leu | Ile | Ala | Val 350 | Ala | Leu |
| Ala | Cys | Phe 355 | Leu | His | Phe | Gly | Lys 360 | Thr | Gly | Arg | Ala | Ser 365 | Asp | Gln | Arg |
| Asp | Leu 370 | Thr | Glu | His | Lys | Pro 375 | Ser | Val | Ser | Asn | His 380 | Thr | Gln | Asp | His |
| Ser 385 | Asn | Asp | Pro | Pro | Asn 390 | Lys | Met | Asn | Glu | Val 395 | Thr | Tyr | Ser | Thr | Leu 400 |
| Asn | Phe | Glu | Ala | Gln 405 | Gln | Pro | Thr | Gln | Pro 410 | Thr | Ser | Ala | Ser | Pro 415 | Ser |
| Leu | Thr | Ala | Thr 420 | Glu | Ile | Ile | Tyr | Ser 425 | Glu | Val | Lys | Lys | Gln 430 | | |

SEQUENCE LISTING (1) GENERAL INFORMATION:
    (i) APPLICANT:    BARNETT, THOMAS R
                          ELTING, JAMES J
                          KAMARCK, MICHAEL E
                          KRETSCHMER, A W
    (ii) TITLE OF INVENTION: CDNAS CODING FOR MEMBERS OF THE

-continued

SEQUENCE LISTING

CARCINOEMBRYONIC ANTIGEN FAMILY
  (iii) NUMBER OF SEQUENCES: 1
  (iv) CORRESPONDENCE ADDRESS:
    (A) ADDRESSEE: SPRUNG HORN KRAMER & WOODS
    (B) STREET: 1140 AVENUE OF THE AMERICAS
    (C) CITY: NEW YORK
    (D) STATE: NEW YORK
    (E) COUNTRY: U.S.A.
    (F) ZIP: 10036
  (v) COMPUTER READABLE FORM:
    (A) MEDIUM TYPE: Floppy disk
    (B) COMPUTER: IBM PC compatible
    (C) OPERATING SYSTEM: PC-DOS/MS-DOS
    (D) SOFTWARE: PatentIn Release #1.0, Version #1.25
  (vi) CURRENT APPLICATION DATA:
    (A) APPLICATION NUMBER: US 07/760,031
    (B) FILING DATE: 13-NOV-1991
    (C) CLASSIFICATION: UNASSIGNED
  (viii) ATTORNEY/AGENT INFORMATION:
    (A) NAME: VASTA JR, VINCENT J
    (B) REGISTRATION NUMBER: 26,655
    (C) REFERENCE/DOCKET NUMBER: MDI 242.5-VJV
  (ix) TELECOMMUNICATION INFORMATION:
    (A) TELEPHONE: (212) 391-0520
    (B) TELEFAX: (212) 382-0949
    (C) TELEX: 423092 NYP UI
(2) INFORMATION FOR SEQ ID NO:14:
  (i) SEQUENCE CHARACTERISTICS:
    (A) LENGTH: 464 amino acids
    (B) TYPE: amino acid
    (D) TOPOLOGY: linear
  (ii) MOLECULE TYPE: peptide
  (iii) HYPOTHETICAL: YES
  (vi) ORIGINAL SOURCE:
    (A) ORGANISM: *HOMO SAPIENS*
  (vii) IMMEDIATE SOURCE:
    (B) CLONE: TRANSLATED POLYPEPTIDE FROM CEA-(f) cDNA
  (xi) SEQUENCE DESCRIPTION: SEQ ID NO:14:

| Met 1 | Gly | His | Leu | Ser 5 | Ala | Pro | Leu | His | Arg 10 | Val | Arg | Val | Pro | Trp 15 | Gln |
|---|---|---|---|---|---|---|---|---|---|---|---|---|---|---|---|
| Gly | Leu | Leu | Leu 20 | Thr | Ala | Ser | Leu | Leu 25 | Thr | Phe | Trp | Asn | Pro 30 | Pro | Thr |
| Thr | Ala | Gln 35 | Leu | Thr | Thr | Glu | Ser 40 | Met | Pro | Phe | Asn | Val 45 | Ala | Glu | Gly |
| Lys | Glu 50 | Val | Leu | Leu | Leu | Val 55 | His | Asn | Leu | Pro | Gln 60 | Gln | Leu | Phe | Gly |
| Tyr 65 | Ser | Trp | Tyr | Lys | Gly 70 | Glu | Arg | Val | Asp | Gly 75 | Asn | Arg | Gln | Ile | Val 80 |
| Gly | Tyr | Ala | Ile | Gly 85 | Thr | Gln | Gln | Ala | Thr 90 | Pro | Gly | Pro | Ala | Asn 95 | Ser |
| Gly | Arg | Glu | Thr 100 | Ile | Tyr | Pro | Asn | Ala 105 | Ser | Leu | Leu | Ile | Gln 110 | Asn | Val |
| Thr | Gln | Asn 115 | Asp | Thr | Gly | Phe | Tyr 120 | Thr | Leu | Gln | Val | Ile 125 | Lys | Ser | Asp |
| Leu | Val 130 | Asn | Glu | Glu | Ala | Thr 135 | Gly | Gln | Phe | His | Val 140 | Tyr | Pro | Glu | Leu |
| Pro 145 | Lys | Pro | Ser | Ile | Ser 150 | Ser | Asn | Asn | Ser | Asn 155 | Pro | Val | Glu | Asp | Lys 160 |
| Asp | Ala | Val | Ala | Phe 165 | Thr | Cys | Glu | Pro | Glu 170 | Thr | Gln | Asp | Thr | Thr 175 | Tyr |
| Leu | Trp | Trp | Ile 180 | Asn | Asn | Gln | Ser | Leu 185 | Pro | Val | Ser | Pro | Arg 190 | Leu | Gln |
| Leu | Ser | Asn 195 | Gly | Asn | Arg | Thr | Leu 200 | Thr | Leu | Leu | Ser | Val 205 | Thr | Arg | Asn |
| Asp | Thr 210 | Gly | Pro | Tyr | Glu | Cys 215 | Glu | Ile | Gln | Asn | Pro 220 | Val | Ser | Ala | Asn |
| Arg | Ser | Asp | Pro | Val | Thr | Leu | Asn | Val | Thr | Tyr | Gly | Pro | Asp | Thr | Pro |

-continued

SEQUENCE LISTING

|  |  |  |  | 225 |  |  |  |  | 230 |  |  |  |  | 235 |  |  |  |  | 240 |
|---|---|---|---|---|---|---|---|---|---|---|---|---|---|---|---|---|---|---|---|
| Thr | Ile | Ser | Pro | Ser 245 | Asp | Thr | Tyr | Tyr | Arg 250 | Pro | Gly | Ala | Asn | Leu 255 | Ser |
| Leu | Ser | Cys | Tyr 260 | Ala | Ala | Ser | Asn | Pro 265 | Pro | Ala | Gln | Tyr | Ser 270 | Trp | Leu |
| Ile | Asn | Gly 275 | Thr | Phe | Gln | Gln | Ser 280 | Thr | Gln | Glu | Leu | Phe 285 | Ile | Pro | Asn |
| Ile | Thr 290 | Val | Asn | Asn | Ser | Gly 295 | Ser | Tyr | Thr | Cys | His 300 | Ala | Asn | Asn | Ser |
| Val 305 | Thr | Gly | Cys | Asn | Arg 310 | Thr | Thr | Val | Lys | Thr 315 | Ile | Ile | Val | Thr | Glu 320 |
| Leu | Ser | Pro | Val | Val 325 | Ala | Lys | Pro | Gln | Ile 330 | Lys | Ala | Ser | Lys | Thr 335 | Thr |
| Val | Thr | Gly | Asp 340 | Lys | Asp | Ser | Val | Asn 345 | Leu | Thr | Cys | Ser | Thr 350 | Asn | Asp |
| Thr | Gly | Ile 355 | Ser | Ile | Arg | Trp | Phe 360 | Phe | Lys | Asn | Gln | Ser 365 | Leu | Pro | Ser |
| Ser | Glu 370 | Arg | Met | Lys | Leu | Ser 375 | Gln | Gly | Asn | Thr | Thr 380 | Leu | Ser | Ile | Asn |
| Pro 385 | Val | Lys | Arg | Glu | Asp 390 | Ala | Gly | Thr | Tyr | Trp 395 | Cys | Glu | Val | Phe | Asn 400 |
| Pro | Ile | Ser | Lys | Asn 405 | Gln | Ser | Asp | Pro | Ile 410 | Met | Leu | Asn | Val | Asn 415 | Tyr |
| Asn | Ala | Leu | Pro 420 | Gln | Glu | Asn | Gly | Leu 425 | Ser | Pro | Gly | Ala | Ile 430 | Ala | Gly |
| Ile | Val | Ile 435 | Gly | Val | Val | Ala | Leu 440 | Val | Ala | Leu | Ile | Ala 445 | Val | Ala | Leu |
| Ala | Cys 450 | Phe | Leu | His | Phe | Gly 455 | Lys | Thr | Gly | Ser | Ser 460 | Gly | Pro | Leu | Gln |

SEQUENCE LISTING (1) GENERAL INFORMATION:
    (i) APPLICANT:    BARNETT, THOMAS R
                            ELTING, JAMES J
                            KAMARCK, MICHAEL E
                            KRETSCHMER, A W
    (ii) TITLE OF INVENTION: CDNAS CODING FOR MEMBERS OF THE
         CARCINOEMBRYONIC ANTIGEN FAMILY
    (iii) NUMBER OF SEQUENCES: 1
    (iv) CORRESPONDENCE ADDRESS:
        (A) ADDRESSEE: SPRUNG HORN KRAMER & WOODS
        (B) STREET: 1140 AVENUE OF THE AMERICAS
        (C) CITY: NEW YORK
        (D) STATE: NEW YORK
        (E) COUNTRY: U.S.A.
        (F) ZIP: 10036
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25
    (vi) CURRENT APPLICATION DATA:
        (A) APPLICATION NUMBER: US 07/760,031
        (B) FILING DATE: 13-NOV-1991
        (C) CLASSIFICATION: UNASSIGNED
    (viii) ATTORNEY/AGENT INFORMATION:
        (A) NAME: VASTA JR, VINCENT J
        (B) REGISTRATION NUMBER: 26,655
        (C) REFERENCE/DOCKET NUMBER: MDI 242.5-VJV
    (ix) TELECOMMUNICATION INFORMATION:
        (A) TELEPHONE: (212) 391-0520
        (B) TELEFAX: (212) 382-0949
        (C) TELEX: 423092 NYP UI

SEQUENCE LISTING (2) INFORMATION FOR SEQ ID NO:15:
   (i) SEQUENCE CHARACTERISTICS:
      (A) LENGTH: 368 amino acids
      (B) TYPE: amino acid
      (D) TOPOLOGY: linear
   (ii) MOLECULE TYPE: peptide
   (iii) HYPOTHETICAL: YES
   (vii) IMMEDIATE SOURCE:
      (B) CLONE: TRANSLATED POLYPEPTIDE FROM CEA-(g) cDNA
   (xi) SEQUENCE DESCRIPTION: SEQ ID NO:15:

| Met 1 | Gly | His | Leu | Ser 5 | Ala | Pro | Leu | His | Arg 10 | Val | Arg | Val | Pro | Trp 15 | Gln |
|---|---|---|---|---|---|---|---|---|---|---|---|---|---|---|---|
| Gly | Leu | Leu | Leu 20 | Thr | Ala | Ser | Leu | Leu 25 | Thr | Phe | Trp | Asn | Pro 30 | Pro | Thr |
| Thr | Ala | Gln 35 | Leu | Thr | Thr | Glu | Ser 40 | Met | Pro | Phe | Asn | Val 45 | Ala | Glu | Gly |
| Lys | Glu 50 | Val | Leu | Leu | Leu | Val 55 | His | Asn | Leu | Pro | Gln 60 | Gln | Leu | Phe | Gly |
| Tyr 65 | Ser | Trp | Tyr | Lys | Gly 70 | Glu | Arg | Val | Asp | Gly 75 | Asn | Arg | Gln | Ile | Val 80 |
| Gly | Tyr | Ala | Ile | Gly 85 | Thr | Gln | Gln | Ala | Thr 90 | Pro | Gly | Pro | Ala | Asn 95 | Ser |
| Gly | Arg | Glu | Thr 100 | Ile | Tyr | Pro | Asn | Ala 105 | Ser | Leu | Leu | Ile | Gln 110 | Asn | Val |
| Thr | Gln | Asn 115 | Asp | Thr | Gly | Phe | Tyr 120 | Thr | Leu | Gln | Val | Ile 125 | Lys | Ser | Asp |
| Leu | Val 130 | Asn | Glu | Glu | Ala | Thr 135 | Gly | Gln | Phe | His | Val 140 | Tyr | Pro | Glu | Leu |
| Pro 145 | Lys | Pro | Ser | Ile | Ser 150 | Ser | Asn | Asn | Ser | Asn 155 | Pro | Val | Glu | Asp | Lys 160 |
| Asp | Ala | Val | Ala | Phe 165 | Thr | Cys | Glu | Pro | Glu 170 | Thr | Gln | Asp | Thr 175 | Thr | Thr |
| Leu | Trp | Trp | Ile 180 | Asn | Asn | Gln | Ser | Leu 185 | Pro | Val | Ser | Pro | Arg 190 | Leu | Gln |
| Leu | Ser | Asn 195 | Gly | Asn | Arg | Thr | Leu 200 | Thr | Leu | Leu | Ser | Val 205 | Thr | Arg | Asn |
| Asp | Thr 210 | Gly | Pro | Tyr | Glu | Cys 215 | Glu | Ile | Gln | Asn | Pro 220 | Val | Ser | Ala | Asn |
| Arg 225 | Ser | Asp | Pro | Val | Thr 230 | Leu | Asn | Val | Thr | Tyr 235 | Gly | Pro | Asp | Thr | Pro 240 |
| Thr | Ile | Ser | Pro | Ser 245 | Asp | Thr | Tyr | Tyr | Arg 250 | Pro | Gly | Ala | Asn | Leu 255 | Ser |
| Leu | Ser | Cys | Tyr 260 | Ala | Ala | Ser | Asn | Pro 265 | Pro | Ala | Gln | Tyr | Ser 270 | Trp | Leu |
| Ile | Asn | Gly 275 | Thr | Phe | Gln | Gln | Ser 280 | Thr | Gln | Glu | Leu | Phe 285 | Ile | Pro | Asn |
| Ile | Thr 290 | Val | Asn | Asn | Ser | Gly 295 | Ser | Tyr | Thr | Cys | His 300 | Ala | Asn | Asn | Ser |
| Val 305 | Thr | Gly | Cys | Asn | Arg 310 | Thr | Thr | Val | Lys | Thr 315 | Ile | Ile | Val | Thr | Asp 320 |
| Asn | Ala | Leu | Pro | Gln 325 | Glu | Asn | Gly | Leu | Ser 330 | Pro | Gly | Ala | Ile | Ala 335 | Gly |
| Ile | Val | Ile | Gly 340 | Val | Val | Ala | Leu | Val 345 | Ala | Leu | Ile | Ala | Val 350 | Ala | Leu |
| Ala | Cys | Phe 355 | Leu | His | Phe | Gly | Lys 360 | Thr | Gly | Ser | Ser | Gly 365 | Pro | Leu | Gln |

SEQUENCE LISTING (1) GENERAL INFORMATION:
    (i) APPLICANT: BARNETT, THOMAS R
                          ELTING, JAMES J
                          KAMARCK, MICHAEL E
                          KRETSCHMER, A W
    (ii) TITLE OF INVENTION: CDNAS CODING FOR MEMBERS OF THE
         CARCINOEMBRYONIC ANTIGEN FAMILY
    (iii) NUMBER OF SEQUENCES: 1
    (iv) CORRESPONDENCE ADDRESS:
        (A) ADDRESSEE: SPRUNG HORN KRAMER & WOODS
        (B) STREET: 1140 AVENUE OF THE AMERICAS
        (C) CITY: NEW YORK
        (D) STATE: NEW YORK
        (E) COUNTRY: U.S.A.
        (F) ZIP: 10036
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25
    (vi) CURRENT APPLICATION DATA:
        (A) APPLICATION NUMBER: US 07/760,031
        (B) FILING DATE: 13-NOV-1991
        (C) CLASSIFICATION: UNASSIGNED
    (viii) ATTORNEY/AGENT INFORMATION:
        (A) NAME: VASTA JR, VINCENT J
        (B) REGISTRATION NUMBER: 26,655
        (C) REFERENCE/DOCKET NUMBER: MDI 242.5-VJV
    (ix) TELECOMMUNICATION INFORMATION:
        (A) TELEPHONE: (212) 391-0520
        (B) TELEFAX: (212) 382-0949
        (C) TELEX: 423092 NYP UI (2) INFORMATION FOR SEQ ID NO:16:
    (i) SEQUENCE CHARACTERISTICS:
        (A) LENGTH: 419 amino acids
        (B) TYPE: amino acid
        (D) TOPOLOGY: linear
    (ii) MOLECULE TYPE: peptide
    (iii) HYPOTHETICAL: YES
    (iv) ANTI-SENSE: NO
    (vi) ORIGINAL SOURCE:
        (A) ORGANISM: *HOMO SAPIENS*
    (vii) IMMEDIATE SOURCE:
        (B) CLONE: TRANSLATED POLYPEPTIDE FROM KGCEA1 cDNA
    (xi) SEQUENCE DESCRIPTION: SEQ ID NO:16:

| Met 1 | Gly | Pro | Leu | Ser 5 | Ala | Pro | Pro | Cys | Thr 10 | His | Leu | Ile | Thr | Trp 15 | Lys |
|---|---|---|---|---|---|---|---|---|---|---|---|---|---|---|---|
| Gly | Val | Leu | Leu 20 | Thr | Ala | Ser | Leu | Leu 25 | Asn | Phe | Trp | Asn | Pro 30 | Pro | Thr |
| Thr | Ala | Gln 35 | Val | Thr | Ile | Glu | Ala 40 | Gln | Pro | Pro | Lys | Val 45 | Ser | Glu | Gly |
| Lys | Asp 50 | Val | Leu | Leu | Leu | Val 55 | His | Asn | Leu | Pro | Gln 60 | Asn | Leu | Ala | Gly |
| Tyr 65 | Ile | Trp | Tyr | Lys | Gly 70 | Gln | Met | Thr | Tyr | Val 75 | Tyr | His | Tyr | Ile | Thr 80 |
| Ser | Tyr | Val | Val | Asp 85 | Gly | Gln | Arg | Ile | Ile 90 | Tyr | Gly | Pro | Ala | Tyr 95 | Ser |
| Gly | Arg | Glu | Arg 100 | Val | Tyr | Ser | Asn | Ala 105 | Ser | Leu | Leu | Ile | Gln 110 | Asn | Val |
| Thr | Gln | Glu 115 | Asp | Ala | Gly | Ser | Tyr 120 | Thr | Leu | His | Ile | Ile 125 | Lys | Arg | Arg |
| Asp | Gly 130 | Thr | Gly | Gly | Val | Thr 135 | Gly | His | Phe | Thr | Phe 140 | Thr | Leu | His | Leu |
| Glu 145 | Thr | Pro | Lys | Pro | Ser 150 | Ile | Ser | Ser | Ser | Asn 155 | Leu | Asn | Pro | Arg | Glu 160 |
| Ala | Met | Glu | Ala | Val 165 | Ile | Leu | Thr | Cys | Asp 170 | Pro | Ala | Thr | Pro | Ala 175 | Ala |
| Ser | Tyr | Gln | Trp 180 | Trp | Met | Asn | Gly | Gln 185 | Ser | Leu | Pro | Met | Thr 190 | His | Arg |

SEQUENCE LISTING

| | | | | | | | | | | | | | | | |
|---|---|---|---|---|---|---|---|---|---|---|---|---|---|---|---|
| Leu | Gln | Leu 195 | Ser | Lys | Thr | Asn | Arg 200 | Thr | Leu | Phe | Ile | Phe 205 | Gly | Val | Thr |
| Lys | Tyr 210 | Ile | Ala | Gly | Pro | Tyr 215 | Glu | Cys | Glu | Ile | Arg 220 | Asn | Pro | Val | Ser |
| Ala 225 | Ser | Arg | Ser | Asp | Pro 230 | Val | Thr | Leu | Asn | Leu 235 | Leu | Pro | Lys | Leu | Ser 240 |
| Lys | Pro | Tyr | Ile | Thr 245 | Ile | Asn | Asn | Leu | Asn 250 | Pro | Arg | Glu | Asn | Lys 255 | Asp |
| Val | Leu | Thr | Phe 260 | Thr | Cys | Glu | Pro | Lys 265 | Ser | Glu | Asn | Tyr | Thr 270 | Tyr | Ile |
| Trp | Trp | Leu 275 | Asn | Gly | Gln | Ser | Leu 280 | Pro | Val | Ser | Pro | Arg 285 | Val | Lys | Arg |
| Pro | Ile 290 | Glu | Asn | Arg | Ile | Leu 295 | Ile | Leu | Pro | Asn | Val 300 | Thr | Arg | Asn | Glu |
| Thr 305 | Gly | Pro | Tyr | Gln | Cys 310 | Glu | Ile | Arg | Asp | Arg 315 | Tyr | Gly | Gly | Ile | Arg 320 |
| Ser | Asp | Pro | Val | Thr 325 | Leu | Asn | Val | Leu | Tyr 330 | Gly | Pro | Asp | Leu | Pro 335 | Ser |
| Ile | Tyr | Pro | Ser 340 | Phe | Thr | Tyr | Tyr | Arg 345 | Ser | Gly | Glu | Asn | Leu 350 | Tyr | Phe |
| Ser | Cys | Phe 355 | Gly | Glu | Ser | Asn | Pro 360 | Arg | Ala | Gln | Tyr | Ser 365 | Trp | Thr | Ile |
| Asn | Gly 370 | Lys | Phe | Gln | Leu | Ser 375 | Gly | Gln | Lys | Leu | Ser 380 | Ile | Pro | Gln | Ile |
| Thr 385 | Thr | Lys | His | Ser | Gly 390 | Leu | Tyr | Ala | Cys | Ser 395 | Val | Arg | Asn | Ser | Ala 400 |
| Thr | Gly | Lys | Glu | Ser 405 | Ser | Lys | Ser | Ile | Thr 410 | Val | Lys | Val | Ser | Asp 415 | Trp |
| Ile | Leu | Pro | | | | | | | | | | | | | |

SEQUENCE LISTING (1) GENERAL INFORMATION:
    (i) APPLICANT:    BARNETT, THOMAS R
                            ELTING, JAMES J
                            KAMARCK, MICHAEL E
                            KRETSCHMER, A W
    (ii) TITLE OF INVENTION: CDNAS CODING FOR MEMBERS OF THE CARCINOEMBRYONIC ANTIGEN FAMILY
    (iii) NUMBER OF SEQUENCES: 1
    (iv) CORRESPONDENCE ADDRESS:
        (A) ADDRESSEE: SPRUNG HORN KRAMER & WOODS
        (B) STREET: 1140 AVENUE OF THE AMERICAS
        (C) CITY: NEW YORK
        (D) STATE: NEW YORK
        (E) COUNTRY: U.S.A.
        (F) ZIP: 10036
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25
    (vi) CURRENT APPLICATION DATA:
        (A) APPLICATION NUMBER: US 07/760,031
        (B) FILING DATE: 13-NOV-1991
        (C) CLASSIFICATION: UNASSIGNED
    (viii) ATTORNEY/AGENT INFORMATION:
        (A) NAME: VASTA JR, VINCENT J
        (B) REGISTRATION NUMBER: 26,655
        (C) REFERENCE/DOCKET NUMBER: MDI 242.5-VJV
    (ix) TELECOMMUNICATION INFORMATION:
        (A) TELEPHONE: (212) 391-0520
        (B) TELEFAX: (212) 382-0949
        (C) TELEX: 423092 NYP UI

5,231,009

-continued

SEQUENCE LISTING (2) INFORMATION FOR SEQ ID NO:17:
  (i) SEQUENCE CHARACTERISTICS:
    (A) LENGTH: 424 amino acids
    (B) TYPE: amino acid
    (D) TOPOLOGY: linear
  (ii) MOLECULE TYPE: peptide
  (iii) HYPOTHETICAL: YES
  (vii) IMMEDIATE SOURCE:
    (B) CLONE: TRANSLATED POLYPEPTIDE FROM KGCEA2 cDNA
  (xi) SEQUENCE DESCRIPTION: SEQ ID NO:17:

| Met 1 | Gly | Pro | Leu | Ser 5 | Ala | Pro | Pro | Cys | Thr 10 | Gln | His | Ile | Thr | Trp 15 | Lys |
|---|---|---|---|---|---|---|---|---|---|---|---|---|---|---|---|
| Gly | Leu | Leu | Leu 20 | Thr | Ala | Ser | Leu | Leu 25 | Asn | Phe | Trp | Asn | Leu 30 | Pro | Thr |
| Thr | Ala | Gln 35 | Val | Ile | Ile | Glu | Ala 40 | Gln | Pro | Pro | Lys | Val 45 | Ser | Glu | Gly |
| Lys | Asp 50 | Val | Leu | Leu | Leu | Val 55 | His | Asn | Leu | Pro | Gln 60 | Asn | Leu | Thr | Gly |
| Tyr 65 | Ile | Trp | Tyr | Lys | Gly 70 | Gln | Met | Thr | Asp | Leu 75 | Tyr | His | Tyr | Ile | Thr 80 |
| Ser | Tyr | Val | Val | Asp 85 | Gly | Gln | Ile | Ile | Tyr 90 | Gly | Pro | Ala | Tyr | Ser 95 | Gly |
| Arg | Glu | Thr | Val 100 | Tyr | Ser | Asn | Ala | Ser 105 | Leu | Leu | Ile | Gln | Asn 110 | Val | Thr |
| Gln | Glu | Asp 115 | Ala | Gly | Ser | Tyr | Thr 120 | Leu | His | Ile | Ile | Lys 125 | Arg | Gly | Asp |
| Gly | Thr 130 | Gly | Gly | Val | Thr | Gly 135 | Tyr | Phe | Thr | Val | Thr 140 | Leu | Tyr | Ser | Glu |
| Thr 145 | Pro | Lys | Arg | Ser | Ile 150 | Ser | Ser | Ser | Asn | Leu 155 | Asn | Pro | Arg | Glu | Val 160 |
| Met | Glu | Ala | Val | Arg 165 | Leu | Ile | Cys | Asp | Pro 170 | Glu | Thr | Pro | Asp | Ala 175 | Ser |
| Tyr | Leu | Trp | Leu 180 | Leu | Asn | Gly | Gln | Asn 185 | Leu | Pro | Met | Thr | His 190 | Arg | Leu |
| Gln | Leu | Ser 195 | Lys | Thr | Asn | Arg | Thr 200 | Leu | Tyr | Leu | Phe | Gly 205 | Val | Thr | Lys |
| Tyr | Ile 210 | Ala | Gly | Pro | Tyr | Glu 215 | Cys | Glu | Ile | Arg | Arg 220 | Gly | Val | Ser | Ala |
| Ser 225 | Arg | Ser | Asp | Pro | Val 230 | Thr | Leu | Asn | Leu | Leu 235 | Pro | Lys | Leu | Pro | Met 240 |
| Pro | Tyr | Ile | Thr | Ile 245 | Asn | Asn | Leu | Asn | Pro 250 | Arg | Glu | Lys | Lys | Asp 255 | Val |
| Leu | Ala | Phe | Thr 260 | Cys | Glu | Pro | Lys | Ser 265 | Arg | Asn | Tyr | Thr | Tyr 270 | Ile | Trp |
| Trp | Leu | Asn 275 | Gly | Gln | Ser | Leu | Pro 280 | Val | Ser | P o | Arg | Val 285 | Lys | Arg | Pro |
| Ile | Glu 290 | Asn | Arg | Ile | Leu | Ile 295 | Leu | Pro | Ser | Val | Thr 300 | Arg | Asn | Glu | Thr |
| Gly 305 | Pro | Tyr | Gln | Cys | Glu 310 | Ile | Arg | Asp | Arg | Tyr 315 | Gly | Gly | Ile | Arg | Ser 320 |
| Asn | Pro | Val | Thr | Leu 325 | Asn | Val | Leu | Tyr | Gly 330 | Pro | Asp | Leu | Pro | Arg 335 | Ile |
| Tyr | Pro | Tyr | Phe 340 | Thr | Tyr | Tyr | Arg | Ser 345 | Gly | Glu | Asn | Leu | Asp 350 | Leu | Ser |
| Cys | Phe | Ala 355 | Asp | Ser | Asn | Pro | Pro 360 | Ala | Glu | Tyr | Phe | Trp 365 | Thr | Ile | Asn |
| Gly | Lys 370 | Phe | Gln | Leu | Ser | Gly 375 | Gln | Lys | Leu | Phe | Ile 380 | Pro | Gln | Ile | Thr |

SEQUENCE LISTING -continued

| Thr 385 | Asn | His | Ser | Gly | Leu 390 | Tyr | Ala | Cys | Ser | Val 395 | Arg | Asn | Ser | Ala | Thr 400 |
|---|---|---|---|---|---|---|---|---|---|---|---|---|---|---|---|
| Gly | Lys | Glu | Ile | Ser 405 | Lys | Ser | Met | Ile | Val 410 | Lys | Val | Ser | Gly | Pro 415 | Cys |
| His | Gly | Asn | Gln 420 | Thr | Glu | Ser | His | | | | | | | | |

What is claimed is:

1. A cell that is transfected, infected or injected with a recombinant cloning vehicle having an insert comprising a nucleic acid sequence which codes for a polypeptide belonging to the CEA family selected from the sequences listed below:
TM-2
TM-3
KGCEA1 or
KGCEA2.

2. A cell that is transfected with free nucleic acid, said free nucleic acid having a sequence which codes for a polypeptide belonging to the CEA family selected from the sequences noted below:
TM-2
TM-3
KGCEA1, or
KGCEA2.

* * * * *

UNITED STATES PATENT AND TRADEMARK OFFICE
CERTIFICATE OF CORRECTION

PATENT NO. : 5,231,009
DATED : July 27, 1993
INVENTOR(S) : Barnett, et al.

It is certified that error appears in the above-indentified patent and that said Letters Patent is hereby corrected as shown below:

Col. 97, lines 19-20    After " TM2 " and " TM3 " insert --,--

Col. 98, lines 18-19    After " TM2 " and " TM3 " insert -- , --

Signed and Sealed this

Second Day of May, 1995

Attest:

BRUCE LEHMAN

Attesting Officer    Commissioner of Patents and Trademarks